(12) United States Patent
Stein et al.

(10) Patent No.: US 10,143,493 B2
(45) Date of Patent: Dec. 4, 2018

(54) DEVICES, COMPOSITIONS AND METHODS FOR BONE AND TISSUE AUGMENTATION

(71) Applicant: REVA Medical, Inc., San Diego, CA (US)

(72) Inventors: Moni Stein, Dublin, OH (US); Donald K. Brandom, La Mesa, CA (US); Lioubov Kabalnova, San Diego, CA (US); Steve Howard, San Diego, CA (US); Robert F. Dennis, San Diego, CA (US)

(73) Assignee: Reva Medical, Inc., San Diego, CA (US)

( * ) Notice: Subject to any disclaimer, the term of this patent is extended or adjusted under 35 U.S.C. 154(b) by 0 days.

(21) Appl. No.: 15/194,396

(22) Filed: Jun. 27, 2016

(65) Prior Publication Data

US 2016/0303278 A1    Oct. 20, 2016

Related U.S. Application Data

(62) Division of application No. 14/172,376, filed on Feb. 4, 2014, now Pat. No. 9,402,859, which is a division
(Continued)

(51) Int. Cl.
*A61B 17/58* (2006.01)
*A61B 17/60* (2006.01)
(Continued)

(52) U.S. Cl.
CPC .......... *A61B 17/58* (2013.01); *A61B 17/8836* (2013.01); *A61F 2/28* (2013.01); *A61F 2/44* (2013.01); *A61F 2/4455* (2013.01); *A61F 2/4611* (2013.01); *A61K 31/78* (2013.01); *A61L 24/001* (2013.01); *A61L 24/06* (2013.01); *C08F 220/18* (2013.01); *A61F 2002/2835* (2013.01);
(Continued)

(58) Field of Classification Search
None
See application file for complete search history.

(56) References Cited

U.S. PATENT DOCUMENTS

| 4,638,045 A | 1/1987 | Kohn et al. |
| 4,863,735 A | 9/1989 | Kohn et al. |

(Continued)

FOREIGN PATENT DOCUMENTS

| WO | WO 2004/014449 | 2/2004 |
| WO | WO 2010/033640 | 3/2010 |

(Continued)

OTHER PUBLICATIONS

Aharoni, et al., "Rigid Backbone Polymers. 2. Polyisocyanates and Their Liquid-Crystal Behavior," Macromolecules, 12(1):94-103 (1979).
(Continued)

*Primary Examiner* — Sameh Boles
(74) *Attorney, Agent, or Firm* — Knobbe, Martens, Olson & Bear, LLP

(57) ABSTRACT

Various polymeric materials and delivery systems are described, along with systems and methods for using them for bone and tissue augmentation, such as for the stabilization and/or correction of spinal compression fractures.

10 Claims, 29 Drawing Sheets

Related U.S. Application Data of application No. 12/886,465, filed on Sep. 20, 2010, now Pat. No. 8,702,716.

(60) Provisional application No. 61/244,240, filed on Sep. 21, 2009.

(51) Int. Cl.
| | |
|---|---|
| *A61F 2/00* | (2006.01) |
| *A61F 2/44* | (2006.01) |
| *A61F 2/46* | (2006.01) |
| *A61B 17/88* | (2006.01) |
| *A61K 31/78* | (2006.01) |
| *A61L 24/06* | (2006.01) |
| *A61F 2/28* | (2006.01) |
| *A61L 24/00* | (2006.01) |
| *C08F 220/18* | (2006.01) |
| *A61F 2/30* | (2006.01) |

(52) U.S. Cl.
CPC ............... *A61F 2002/30677* (2013.01); *A61F 2002/4495* (2013.01); *A61F 2002/4631* (2013.01); *A61F 2210/0085* (2013.01); *A61F 2310/00353* (2013.01); *A61L 2430/38* (2013.01); *C08F 2220/1891* (2013.01)

(56) References Cited

U.S. PATENT DOCUMENTS

| | | | |
|---|---|---|---|
| 5,198,507 A | 3/1993 | Kohn et al. | |
| 5,469,867 A | 11/1995 | Schmitt | |
| 5,912,225 A | 6/1999 | Mao et al. | |
| 6,238,687 B1 | 5/2001 | Mao et al. | |
| 8,702,716 B1 | 4/2014 | Stein et al. | |
| 2004/0230309 A1 | 11/2004 | DiMauro et al. | |
| 2006/0024266 A1 | 2/2006 | Brandom et al. | |
| 2006/0036316 A1 | 2/2006 | Zeltinger et al. | |
| 2006/0142779 A1 | 6/2006 | Arramon et al. | |
| 2006/0182779 A1* | 8/2006 | Brandom ................ A61L 31/06 424/423 |
| 2008/0154304 A1 | 6/2008 | Crawford et al. | |
| 2009/0012525 A1 | 1/2009 | Buehlmann et al. | |
| 2011/0212050 A1 | 9/2011 | Brandom et al. | |
| 2011/0213090 A1 | 9/2011 | Brandom et al. | |
| 2011/0213456 A1 | 9/2011 | Brandom et al. | |

FOREIGN PATENT DOCUMENTS

| | | |
|---|---|---|
| WO | WO 2010/042917 | 4/2010 |
| WO | WO 2010/042918 | 4/2010 |

OTHER PUBLICATIONS

Andruzzi, et al., "Studies on Comb-like Polymers. 2. Poly(octadecylethylene oxide)," Macromolecules, 13: 15-18(1980).

Banse, et al., Failure Strains Properties of the Whole Human Vertebral Body, Poster Session—The Spine—46th Annual Meeting, Orthopaedic Research Society, Mar. 12-15, 2000 Orlando, Florida.

Chupov, et al., "Structure and Physico-Chemical Properties of Comb-Like Polypeptides Based on Poly-L-Lysine" Polymer Science U.S.S.R. 21:241-252 (1979).

Dublin, et al., "The Vertebral Body Fracture in Osteoporosis: Restoration of Height Using Percutanous Vertebroplasty," AJNR Am J Neuroradiol 26:489-492 (2005).

Gonzalez, et al. Side-Chain Crystallinity, Heat of Melting, and Thermal Transitions in poly[N- (10-n-Alkyloxycarbonyl-n-Decyl) Maleimides] (PEMI), Journal of Polymer Science: Polymer Physics Edition. 11:2197-2207 (1980).

Greenberg et al., "Side Chain Crystallization of n-Alkyl Polymethacrylates and Polyacrylates," J.A.C.S. 76:6280 (1954).

Jayakrishnan, et al., "Synthesis and Polymerization of Some Iodine-Containing Monomers for Biomedical Applications," Journal of Applied Polymer Science 44:743-748 (1992).

Jordan, et al.,"Side-Chain Crystallinity. III. Influence of Side-Chain Crystallinity on the Glass Transition Temperatures of Selected Copolymers Incorporating n-Octadecyl Acrylate or Vinyl Stearate," Journal of Polymer Science: Part A-1 9:3367-3378(1971).

Jordan, et al.,"Side-Chain Crystallinity. II. Heats of Fusion and Melting Transitions on Selected Copolymers Incorporating n-Octadecyl Acrylate or Vinyl Stearate" Journal of Polymer Science: Part A-1, 9:3349-3365 (1971).

Jordan, et al.,"Side-Chain Crystallinity. I. Heats of Fusion and Melting Transitions on Selected Homopolymers Having Long Side Chains," Journal of Polymer Science: Part A-1, 9:1835-1852 (1971).

Jordan, et al., "Side-Chain Crystallinity. V. Heats of Fusion and Melting Temperatures on Monomers Whose Homopolymers Have Long Side Chains," Journal of Polymer Science, 10:3347-3366 (1972).

Kruft, et al., "Studies on radio-opaque polymeric biomaterials with potential applications to endovascular prostheses," Biomaterials, 17: 1803-1812 (1996).

Magagnini, et al., "Studies on Comb-like Polymers. 1. Poly(octadecylethylene)," Macromolecules, 13: 12-15(1980).

O'Driscoll, et al., "Kinetics of Anionic Copolymerization of Monomers of Similar Polarities," Journal of Polymer Science, 61: 19-24 (1962).

Overberger, et al., "The Preparation and Polymerization of p-Alkylstyrenes. Effect of Structure on the Transition Temperatures of the Polymers," 75:3326-3330 (1953).

Paderni, et al., "Major bone defect treatment with an osteoconductive bone substitute," Chir. Organi Mov. 93(2):89-96 (2009).

Plate, et al., "Comb-Like Polymers. Structure and Properties," J. Polymer Sci.:Macromolecular Reviews, 8: 117-253 (1974).

Pittman, et al., "Effect of Polymer Crystallinity on the Wetting Properties of Certain Fluroalkyl Acrylates," Journal of Polymer Science Part A-1, 7:3053-3066 (1969).

Rabolt, et al., "Studies of Chain Conformational Kinetics in Poly(di-n-alkylsilanes) by Spectroscopic Methods. 1. Poly(di-n-hexylsilane), Poly(di-n-heptylsilane), and Poly(di-n-octylsilane)," Macromolecules, 19:611-616 (1986).

Reddi, et al., "Bone morphogenetic proteins (BMPs): from morphogens to metabologens," Cytokine Growth Factor Reviews 20(5-6):341-342 (2009).

Wada, et al., "Effect of Amount of Medium on the Radiation-Induced Polymerization of Ethylene in tert-Butvl Alcohol," Journal of Polymer Science: Part A-1, 10: 1655-1667 (1972).

Watanabe, et al., "Thermotropic Polypeptides. 2. Molecular Packing and Thermotropic Behavior of Poly (L-glutamates) with Long n-Alkyl Side Chains," Macromolecules 18:2141-2148 (1985).

Yokota, et al., "Widely-Spaced Comb-Like Polymers Having Fluoroalkyl Side Chains," Polymer Journal 17:991-996 (1985).

* cited by examiner (polymer delivery system)

(delivery needle)

130 polymer line cross-sections 131 lead portion (properties 1)

132 trailing portion (properties 2)

138 polymer line cross-sections 133 shell (properties 1)

134 core (properties 2)

139 polymer line cross-sections 135 matrix (properties 1)

136 suspended threads (properties 2)

137 suspended beads (properties 2)

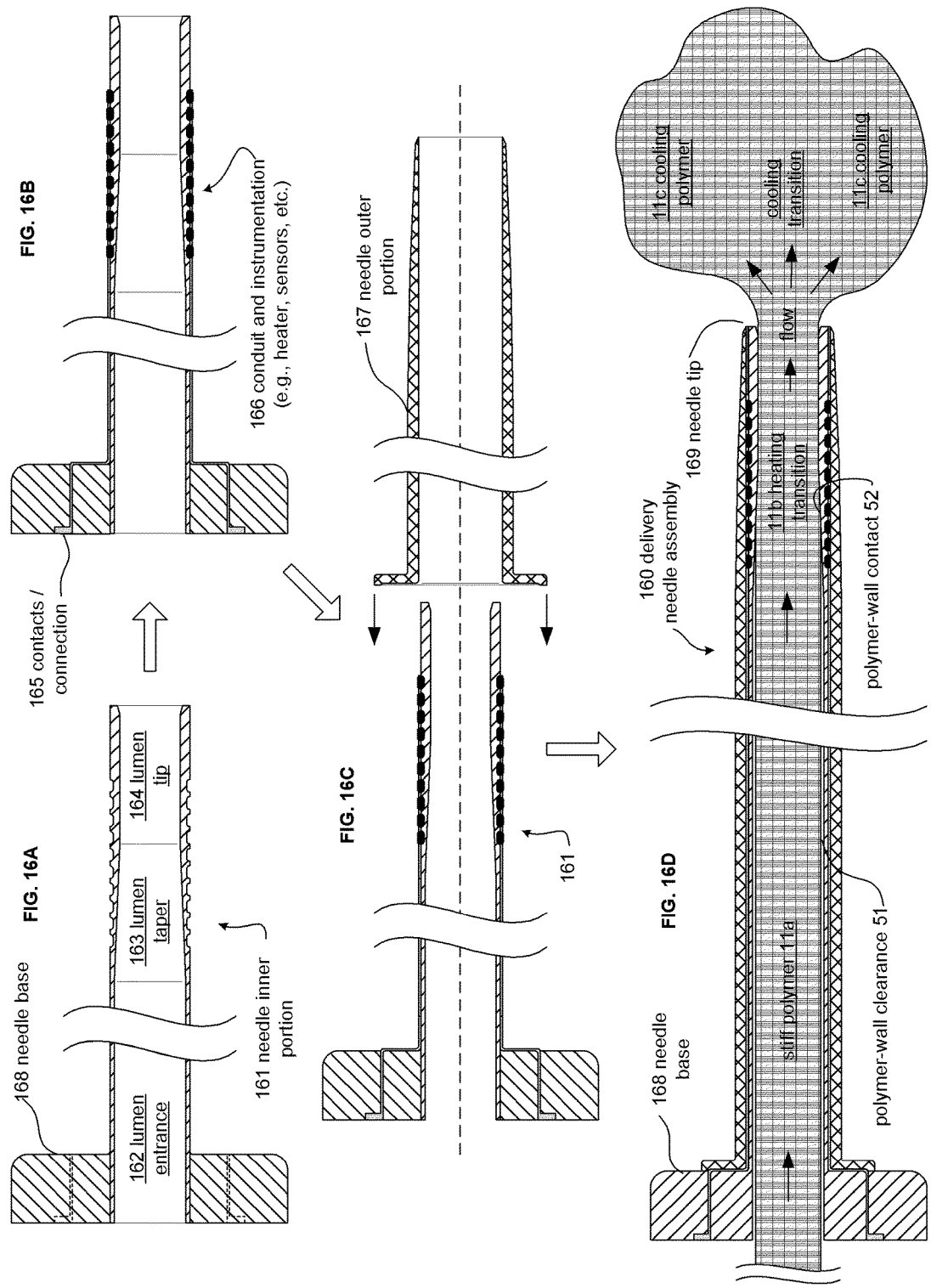

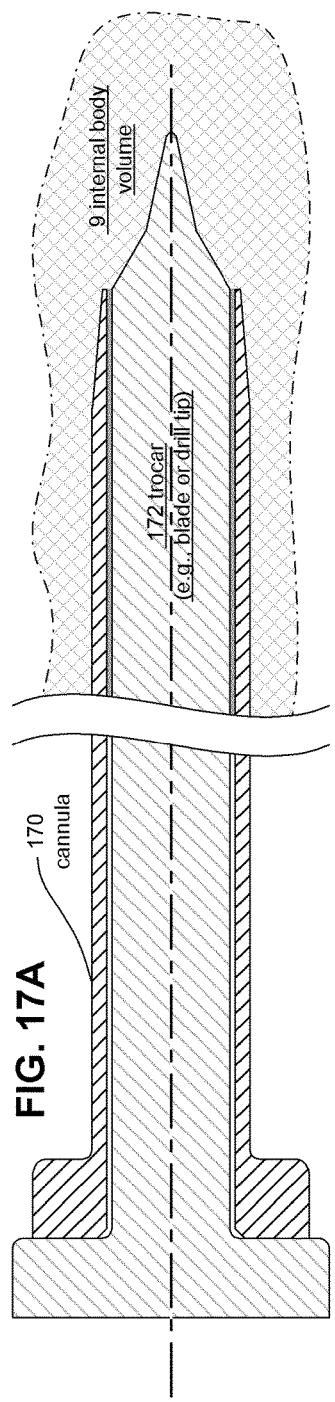
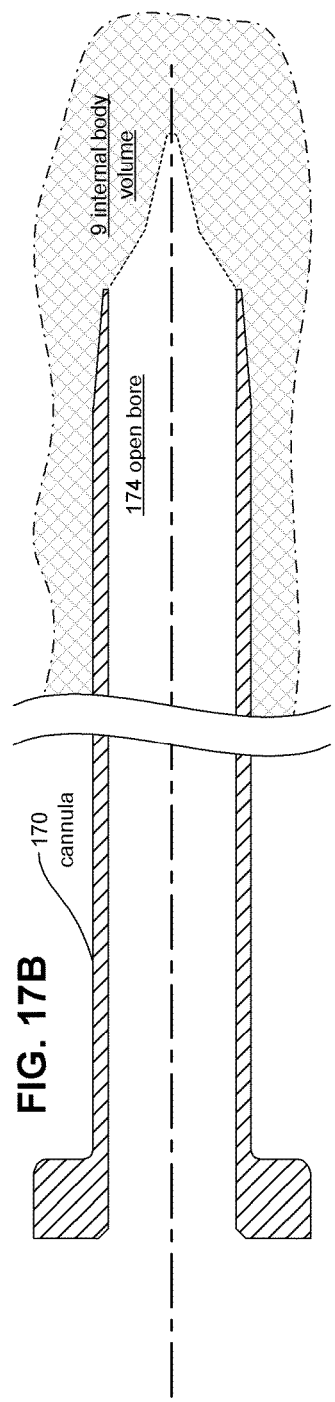
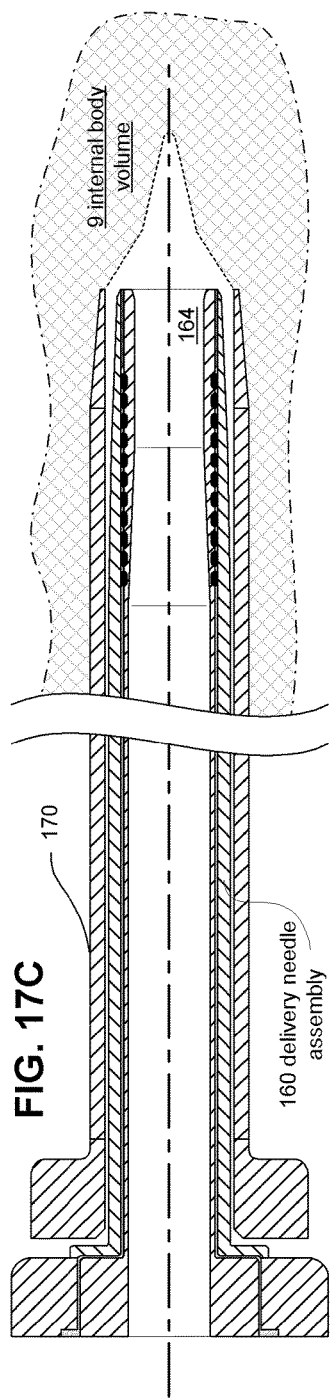

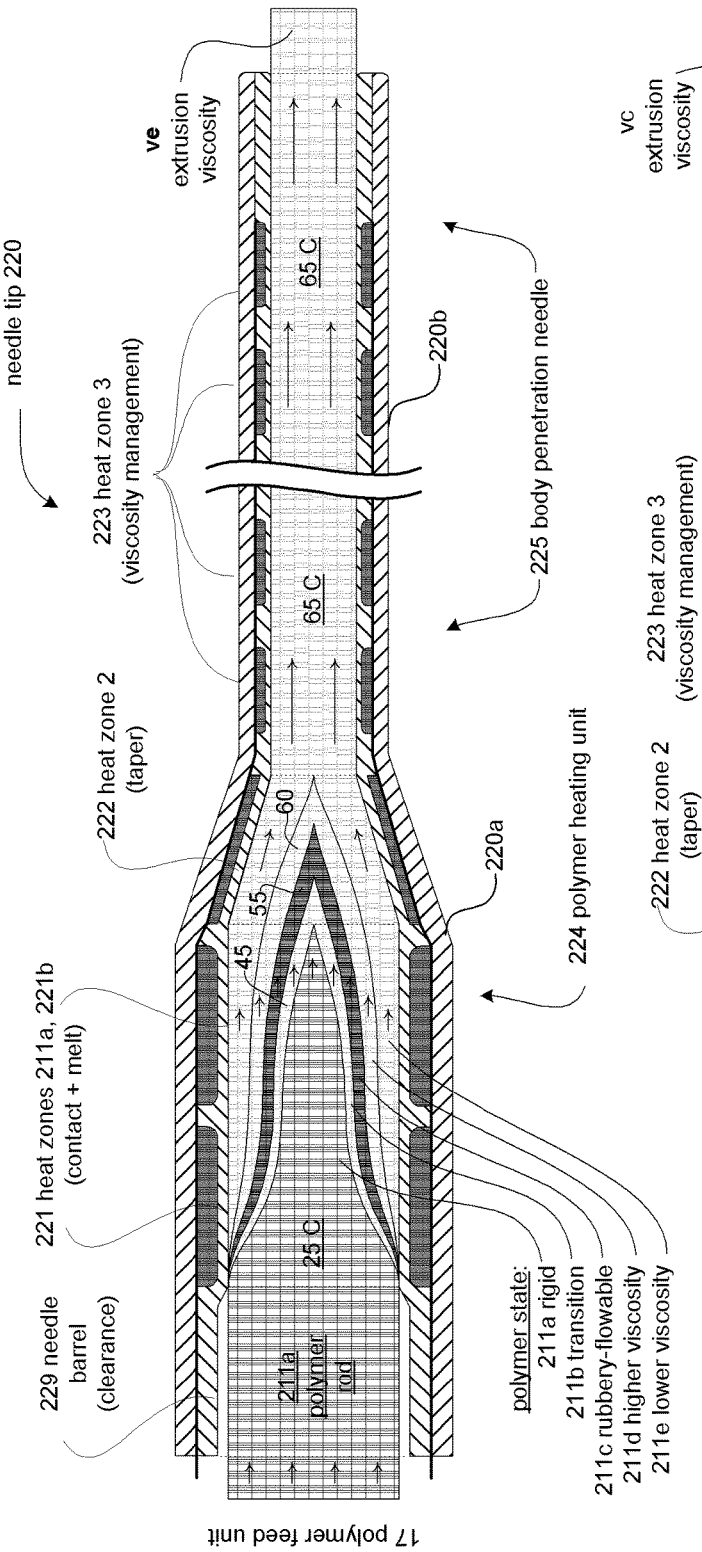
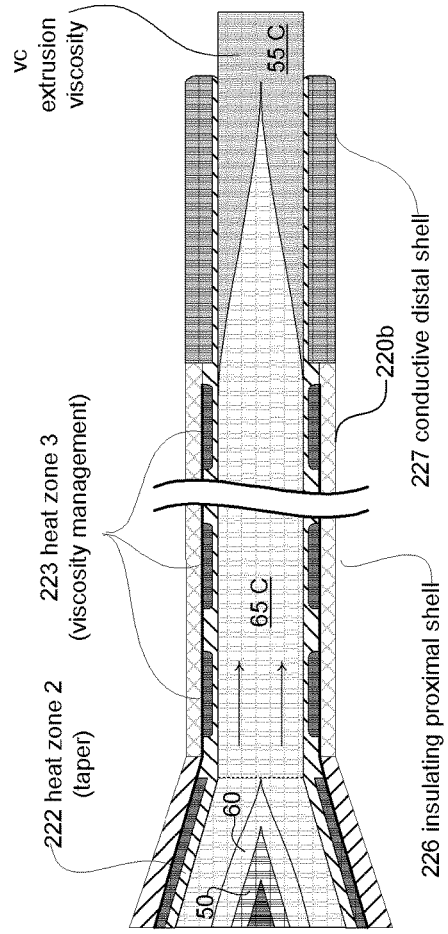
FIG. 22A
FIG. 22B

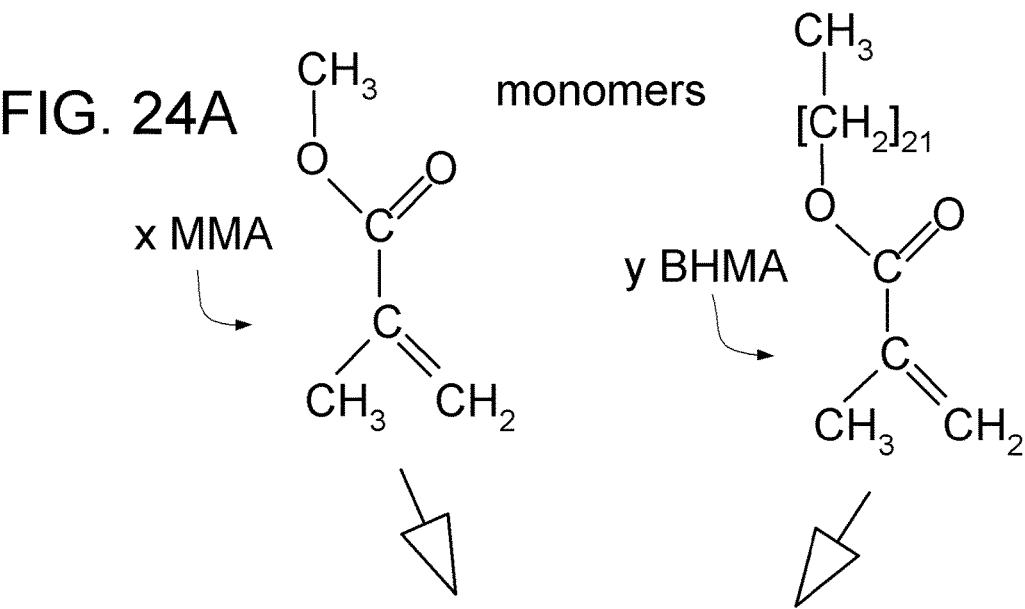
FIG. 24A monomers
x MMA  y BHMA
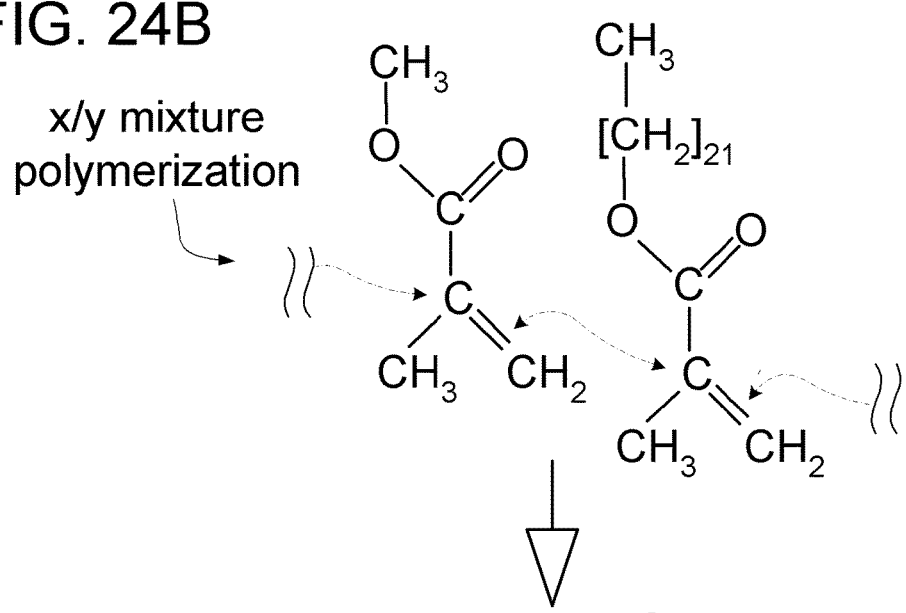
FIG. 24B
x/y mixture polymerization
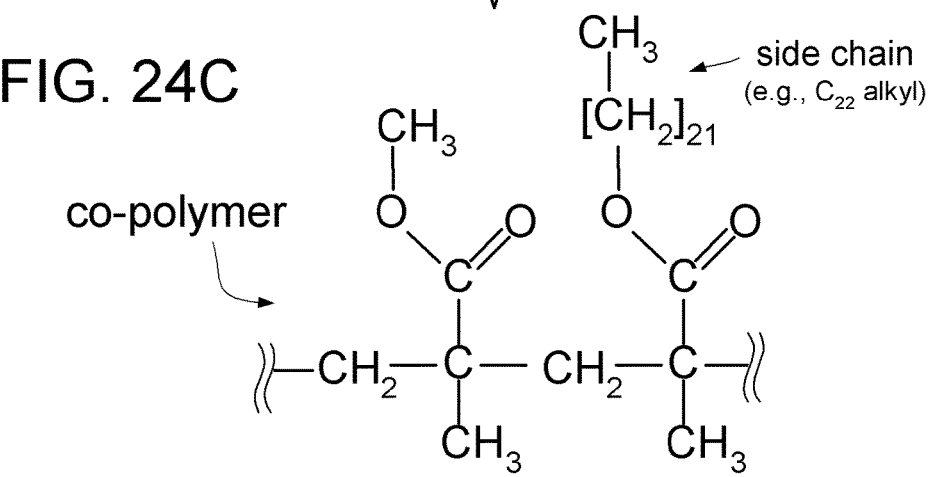
FIG. 24C
co-polymer
side chain (e.g., $C_{22}$ alkyl)

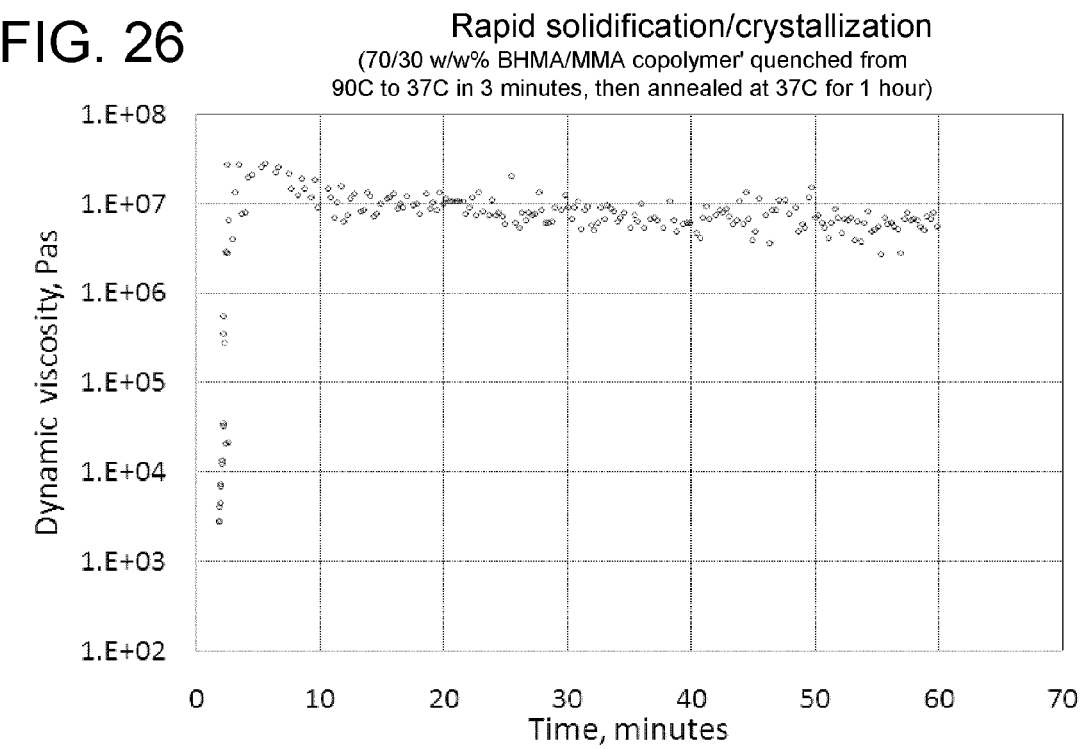
FIG. 26 Rapid solidification/crystallization
(70/30 w/w% BHMA/MMA copolymer' quenched from
90C to 37C in 3 minutes, then annealed at 37C for 1 hour)
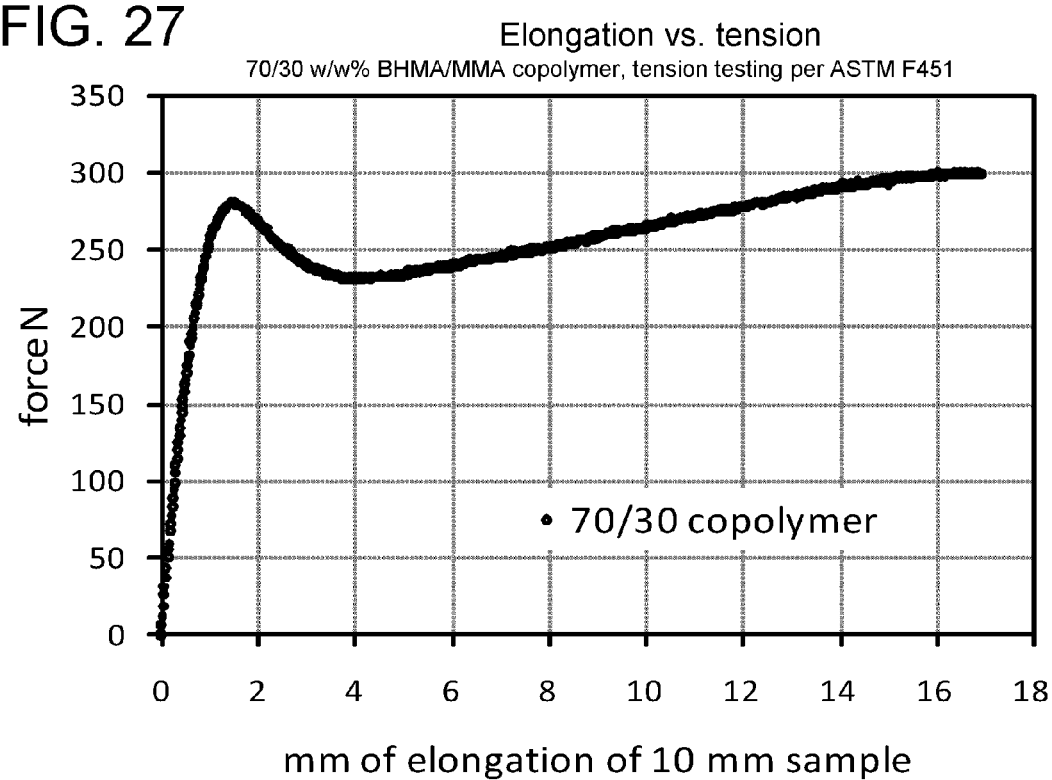
FIG. 27 Elongation vs. tension
70/30 w/w% BHMA/MMA copolymer, tension testing per ASTM F451

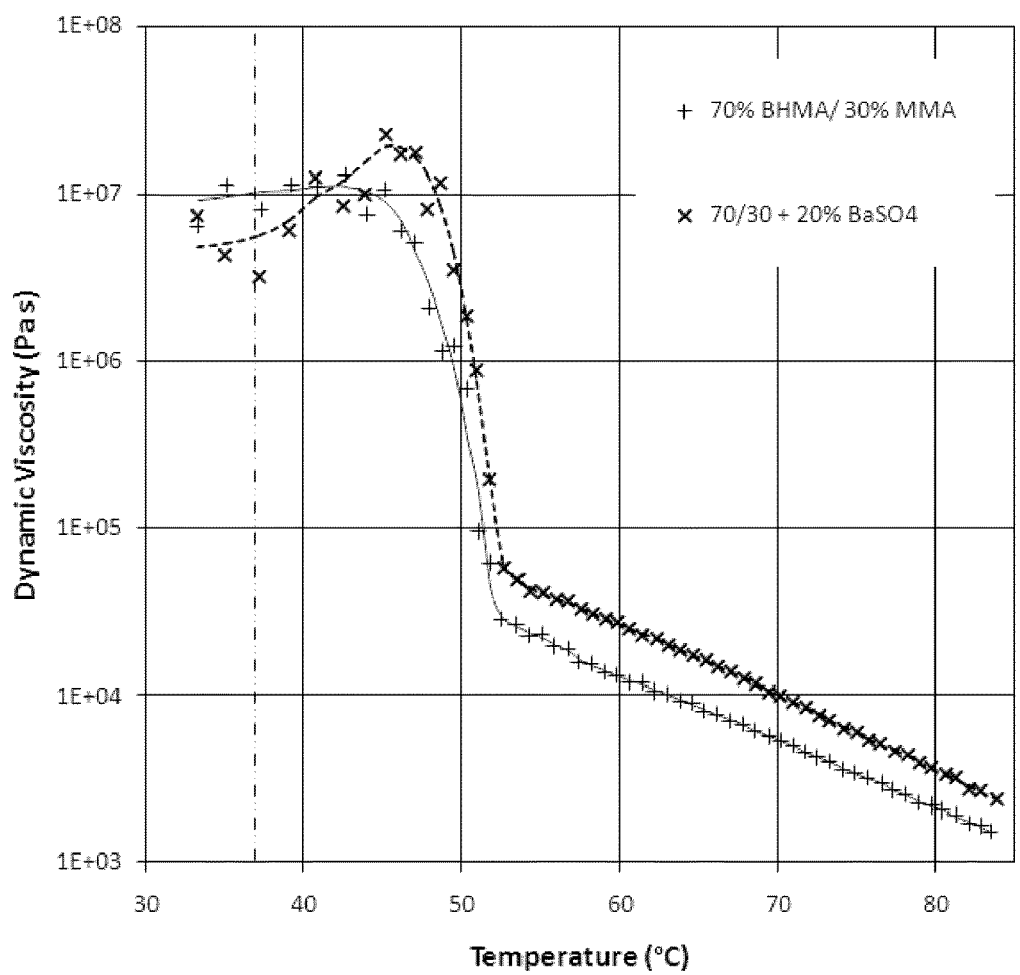
FIG. 28  Effect of Radio-opacity additive
(70/30 w/w% BHMA/MMA copolymer, mixed with 20% w/w% $BaSO_4$)

| Co-polymer Composition<br>MMA = methyl methacrylate<br>HMA = hexyl methacrylate<br>BHMA = behenyl methacrylate | Dynamic viscosity at 60C, Pa.s | Dynamic viscosity at 70C, Pa.s | Dynamic viscosity at 80C, Pa.s |
|---|---|---|---|
| 50/50, w/w% MMA/HMA | 6,000,000 | 290,000 | 200,000 |
| 50/50, w/w% BHMA/MMA | 3,360,000 | 450,000 | 206,000 |
| 60/40, w/w% BHMA/MMA | 74,000 | 40,500 | 20,000 |
| 70/30, w/w% BHMA/MMA | 12,000 | 5,300 | 2,000 |
| 80/20, w/w% BHMA/MMA | 635 | 250 | 115 |
| 100 w/w% BHMA | 50 | 5 | 2 |

FIG. 29B  Effect of Copolymer Compositions on Viscosity

| Molecular Weight, kDa (70/30, w/w% BHMA/MMA co-polymer) | Dynamic viscosity at 60C, Pa.s | Dynamic viscosity at 70C, Pa.s | Dynamic viscosity at 80C, Pa.s |
|---|---|---|---|
| 317 | 40,000 | 29,500 | 20,000 |
| 166 | 12,000 | 5,300 | 2,000 |
| 125 | 10,000 | 4,200 | 1,500 |

FIG. 30B  Effect of Molecular Weight on Viscosity
(70/30 w/w% BHMA/MMA copolymer)

FIG. 31A  Effect of Copolymer Composition on Compressive Strength

| Co-polymer Composition | Ult. Load, N | Strength, MPa |
|---|---|---|
| 100 w/w% BHMA | 107 | 3.2 |
| 80/20, w/w% BHMA/MMA | 258 | 9.2 |
| * 70/30, w/w% BHMA/MMA | 387 | 12.5 |
| 70/30 BHMA/MMA + 20%BaSO$_4$ | 493 | 19 |
| *70/15/15, w/w% BHMA/MMA/HMA | 327 | 10.6 |
| 70/25/5, w/w% BHMA/MMA/HMA | 342 | 12.6 |
| 60/40, w/w% BHMA/MMA | 386 | 13.9 |
| Healthy lumbar vertebra | | < 8 |
| Osteoporotic lumbar vertebra | | <<4 |
| Current commercial cements | | 70 – 200 |

Compression testing according to ASTM F451      * see Fig. 31B

FIG. 31B
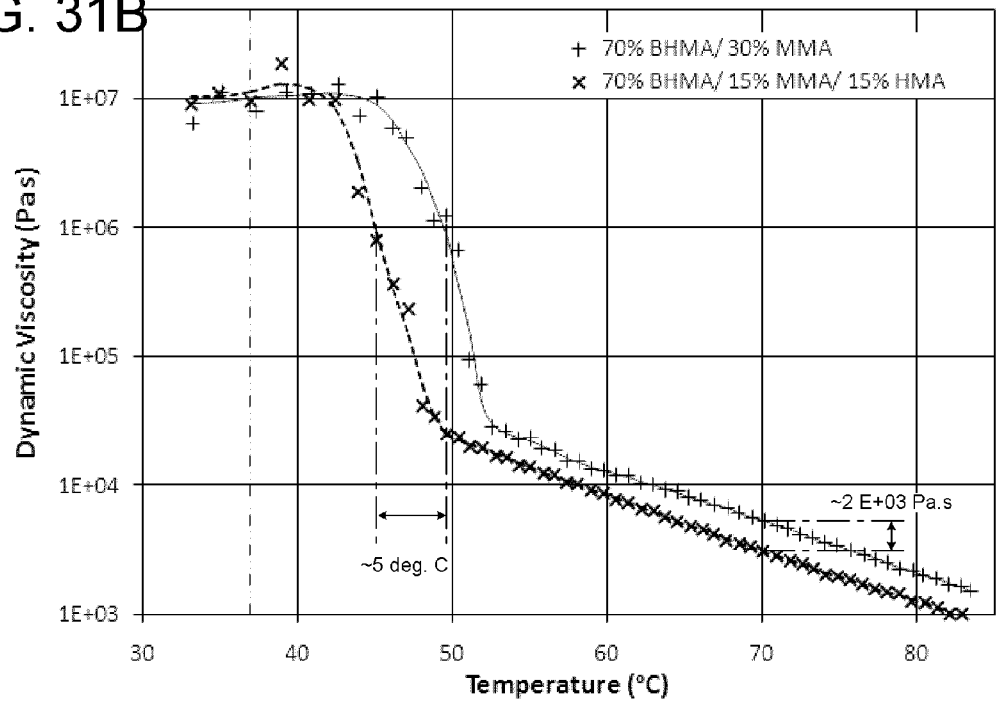

DEVICES, COMPOSITIONS AND METHODS FOR BONE AND TISSUE AUGMENTATION

CROSS-REFERENCE TO RELATED APPLICATIONS

This application is a divisional of U.S. application Ser. No. 14/172,376, filed Feb. 4, 2014, which is a divisional of U.S. application Ser. No. 12/886,465, filed Sep. 20, 2010, now U.S. Pat. No. 8,702,716, which claims the benefit of priority to U.S. Provisional Application No. 61/244,240 filed Sep. 21, 2009, the entireties of which are incorporated herein by reference.

This application relates to certain subject matter of the following co-assigned applications: U.S. application Ser. No. 11/335,771 filed Jan. 18, 2006 (US2006-0182779), which is a continuation-in-part of U.S. application Ser. No. 11/176,638, filed Jul. 7, 2005 (now U.S. Pat. No. 7,939,611), which claims priority to U.S. Ser. No. 60/586,796 filed Jul. 8, 2004; and U.S. application Ser. No. 11/200,656 filed Aug. 10, 2005 (now U.S. Pat. No. 7,473,417), which claims priority to U.S. Ser. No. 60/601,526 filed Aug. 13, 2004. Each of these applications is incorporated by reference herein.

BACKGROUND

Field of the Invention

This invention relates to methods, materials and devices for bone and tissue augmentation, and in particular for the stabilization and/or correction of spinal compression fractures. The present invention also relates to radiopaque and non-radiopaque polymers, and their use in bone augmentation systems. Also described herein are novel vertebroplasty cements and delivery systems. The polymers and systems described herein can be used in methods for treating bone fractures, such as vertebral compression fractures.

Description of the Related Art

Polymeric materials are widely used in numerous applications. For example, therapeutic embolization is the selective blockage of blood vessels or diseased vascular structures. Examples of polymeric embolotherapy devices and reagents include embolic coils, gel foams, glues, and particulate polymeric embolic agents used, for example, to control bleeding, prevent blood loss prior to or during a surgical procedure, restrict or block blood supply to tumors and vascular malformations, e.g., for uterine fibroids, tumors (e.g., chemo-embolization), hemorrhage (e.g., during trauma with bleeding) and arteriovenous malformations, fistulas (e.g., AVF's) and aneurysms.

A number of technological applications involve the use of a polymer that undergoes a transition upon a change in temperature. For example, in the medical field, one way to introduce a solid polymer into a particular body region is to heat the polymer into a flowable state, then inject the polymer into the region and allow it to cool and solidify. U.S. Pat. No. 5,469,867 discloses side-chain crystallizable polymers that are said to be useful for occluding channels in a living mammal. Such polymers are said to be designed such that they can be melted so that they are flowable slightly above body temperature but solidify when cooled to body temperature. See also WO2004-014449, which describes a miscible blend of polymers for medical device applications. Each of these publications U.S. Pat. No. 5,469,867 and WO2004-014449 are incorporated herein by reference.

Vertebral Compression Fractures.

One of the most common types of bone fractures are vertebral compression fractures, with approximately 600,000 fractures diagnosed each year. A vertebral compression fracture comprises a collapse of one or more vertebrae in the spine, which, for example, may be caused by bone diseases such as osteoporosis or direct trauma to the spine. Several treatment options are available for such compression fractures. One non-invasive method of treating a compression fracture is by oral administration to the patient of the polypeptide calcitonin, which may provide an analgesic effect while treating the underlying fracture. However, such a relatively conservative treatment is typically not sufficient for patients with anything more than a modestly compromised vertebra.

Polymeric materials and application devices have also been developed for stabilizing and/or correcting the form of vertebral bodies that have been injured, such as by compression fractures occurring from trauma or as a result of osteoporosis or cancer. Such fractures, which may involve the compression or collapse of one or more vertebrae in the spine, cause pain and deformation of the spine via distortion of the normal approximately rectangular cross-section of the vertebral body.

Two minimally invasive surgical procedures are also available. For example, vertebroplasty is a medical procedure where bone cement is percutaneously injected into a fractured vertebra in order to stabilize it and reduce pain. Prior art minimally invasive vertebroplasty procedures typically use X-ray guidance to: (a) advance a hollow needle or cannula into a central volume of a vertebral body adjacent the fractured bone; (b) inject a precursor cement fluid (bone cement, e.g., polymethylmethacrylate-based cement, which may be referred to herein as PMMA); and (c) react the precursor fluid in situ with a catalyst and/or energy source so as to form a thermoset polymeric support/cement substance. Typically the precursor fluid includes a radio-opaque substance such as barium sulfate to permit X-ray visualization of the fluid as it is administered and/or after it has been cured. See for example, US Patent Application Publication Nos. 2009-0012525 ("Devices and systems for delivering bone fill material"); 2006-0142779 ("Cannula having asymmetrically-shaped threads"); and 2008-0154304 ("System and method for accessing a tissue structure"), each of which applications is incorporated by reference herein.

A variation of this treatment is known as kyphoplasty, a procedure to restore at least some of the height lost in vertebral compression fractures and to reduce spinal distortion. See for example Dublin, et al.; "*The Vertebral Body Fracture in Osteoporosis: Restoration of Height Using Percutaneous Vertebroplasty*"; AJNR Am J Neuroradiol 26:489-492, March 2005, which publication is incorporated by reference herein. In one example of kyphoplasty, a balloon may be first inserted through a needle into the fractured bone to restore the height and shape of the vertebra. Then the balloon is removed and the cement mixture is injected as described above into the cavity created by the balloon.

However, currently available techniques of both vertebroplasty and kyphoplasty have several drawbacks. Bone cements used in vertebroplasty and kyphoplasty that are on the market today are primarily based on PMMA. While PMMA is compatible with human tissue for this purpose, the polymer and its monomer may be non-ideal in many applications. For example, PMMA is not radiopaque and thus, for situations in which radiopacity is desired, e.g. to monitor its application into the human body, a radiopacifying agent is generally added to the polymer. Additionally, PMMA and its monomer are known to have a degree of inherent toxicity. Toxicity concerns limit the number of vertebral fractures that can be treated in a single procedure.

PMMA and other currently available bone cements are also prone to leakage into non-treatment areas due to the inability to accurately control their viscosity. Cement leakage into the spinal column can cause permanent paralysis or other neurological damage to the patient. The generally high viscosity of the currently available bone cements also tends to require that a larger, lower gauge needle be used during the surgical procedure, which may cause additional pain and trauma to the patient. Furthermore, after the bone cement hardens, the final rigidity of the hardened cement is generally about three times harder than that of the natural bone with which it interacts, making future vertebrae fractures more likely.

The currently available bone cements used in vertebroplasty and kyphoplasty systems are often provided as two or more distinct components, which require mixing in the operating room before injection into the fractured vertebra. One common mixture is a combination of PMMA, methyl methacrylate monomer, and a thermal-initiator. The step of mixing separate components can lead to technical problems in about 50% of the minimally invasive surgical procedures. For example, problems can arise with inconsistent mixing and limited working time for surgical application upon mixture. Therefore, there is a need to provide polymers and delivery systems for use in methods of treating compression fractures which overcome one or more of the above-discussed disadvantages.

Structural Alloplastic Bone Grafts and Spinal Fusion.

Another therapeutic application presenting structural challenges is alloplastic bone grafting. Bone grafting is used in repairs for a wide variety of medical conditions presenting the need to provide replacement of damaged, lost or diseased bone. In some applications, structural support during graft healing is provided by adjacent bone. However, in other applications the graft material provides support for tissue and body structure during the healing process. Bone grafts may employ naturally occurring bone materials (autografts, allografts and xenographs), or may employ synthetic materials (alloplatic grafts), or combinations of these.

Alloplastic graft materials are available that are flow-delivered, but typically, these have poor mechanical integrity and thus have generally been limited to non-structural applications. On the other hand, structural implants are available, but they typically require substantially invasive surgical procedures. In the case of spinal fusion procedures (e.g., interbody fusion), a structural support device made of plastic or titanium may be fixed between the vertebra to maintain spine alignment and disc height.

Although malleable or flowable alloplastic graft materials capable of forming in-situ structural elements have been proposed, these materials and methods have limitations due to the requirement for inconvenient in-situ curing or cross-linking steps, or due to the comparatively high temperatures required to render a conventional thermoplastic matrix material malleable or extrudable. See for example, US Patent Application Publication No. 2004-0230309 entitled "In-situ formed intervertebral fusion device and method".

In addition to spinal fusion procedures, in the repair of vertebral compression fractures in youths to middle-age adults, it is desirable to avoid permanent implant or bone cement material in favor of the re-growth of natural bone to heal the fracture. In these patients, a structural alloplastic bone graft material suited to minimally invasive fracture repair is highly desirable.

For further information, see:
(a) Data Book on Mechanical Properties of Living Cells, Tissues, and Organs, Hiroyuki Abe (Editor), Kozaburo Hayashi (Editor), Masaaki Sato (Editor), Springer-Verlag, New York, Tokyo, 1996;
(b) Failure Strains Properties of the Whole Human Vertebral Body, Banse, X; Munting, E; Cornu, O; Van Tomme, J; and Delloye, C, Poster Session—The Spine—46th Annual Meeting, Orthopaedic Research Society, Mar. 12-15, 2000, Orlando, Fla.;
(c) Major bone defect treatment with an osteoconductive bone substitute. Paderni S, Terzi S, Amendola L., Chir Organi Mov. 2009 September; 93(2):89-96. Epub 2009 Jun. 16; and
(d) Cytokine Growth Factor Rev. 2009 October-December; 20(5-6):341-2. Epub 2009 Nov. 8. "Bone morphogenetic proteins (BMPs): from morphogens to metabologens". Reddi A H, Reddi A.; each of these publications being incorporated by reference herein.

SUMMARY OF THE INVENTION

The above incorporated-by-reference co-assigned patent application Ser. Nos. 11/335,771 and 11/176,638, each entitled "Side-chain crystallizable polymers for medical applications" describe examples of polymer compositions which can have tailored thermomechanical properties making them particularly suitable for applications in which the composition undergoes a mechanical property transition upon a change in temperature spanning the temperature of a patient's body.

Embodiments Employing Precursor Compositions for In-Vivo Reaction.

Described herein are materials that can be used as a bone cement to be delivered within a mammalian body cavity/space and subsequently reacted, e.g. cured, via electromagnetic radiation (EM) to change its mechanical and flow properties to a substantially non-absorbable state. In an embodiment, the materials described herein do not require physical admixture immediately prior to the minimally invasive surgical procedure. Rather, the ingredients of the composition can be mixed well in advance of their implantation into a mammalian body. The compositions described herein are thermally stable, and can be heated without becoming permanently rigid. Preferably, the compositions comprise a photo-initiator which, upon exposure to visible or UV light, alters the flow properties of the injectable composition to provide a rigid and permanent shape.

The photo-initiator is preferably thermally stable. In an embodiment, the photo-initiator does not cross-link upon heating up to 80° C. In an embodiment, the photo-initiator does not cross-link upon heating up to 100° C. In an embodiment, the photo-initiator does not cross-link upon heating up to 120° C. In an embodiment, the photo-initiator comprises one or more double bonds. In an embodiment, the double bonds are cross-linkable. Suitable examples of a photo-initiator include, but are not limited to benzoin methyl ether and benzophenone.

In an embodiment, the composition is a pre-cursor bone cement composition. In an embodiment, the pre-cursor bone cement composition comprises a polymer. In an embodiment, the pre-cursor bone cement composition comprises an oligomer. In an embodiment, the pre-cursor bone cement composition comprises a monomer. In an embodiment, the polymer is inherently radiopaque. In an embodiment, the polymer, oligomer, and or monomer comprise crystallizable side chains.

A delivery device can be used to administer the bone cement. In an embodiment, the delivery device comprises a rod capable of holding the bone cement and a delivery cannula. The delivery device can reach a targeted body space and then can be used to inject the bone cement into a treatment area of the vertebra. The cross-section of the delivery device can be circular or polygonal in geometry, such as with conventional cannulas or catheters. Preferably, the delivery device is substantially circular. The bone cement is fed from outside the patient's body through the delivery device into the interior targeted space. In an embodiment, the delivery cannula can be heated.

The precursor bone cement composition can be a homogenous or heterogeneous material comprising photo-sensitive moieties that will act as reactive loci upon exposure to EM or UV radiation. In an embodiment, the precursor bone cement composition is a flowable mass or malleable solid at room temperature. In an embodiment, the precursor bone cement composition comprises a filament. In an embodiment, the filament is placed into a shaft of delivery device, as illustrated, for example, in FIG. 3A. In an embodiment, the filament comprises a polymer. In an embodiment, the filament comprises an oligomer. In an embodiment, the filament comprises monomers, which may be polymerized and cured upon administration into a treated area.

The delivery cannula can be heated or can remain at room temperature. In an embodiment, the delivery cannula is at a temperature in the range of about body temperature to about 80° C. In an embodiment, the delivery cannula is at a temperature in the range of slightly above body temperature to about 70° C. In an embodiment, the delivery cannula is at a temperature in the range of about 40° C. to about 60° C. Once the material has been delivered to the treated area, a solid mass substantially conforming to the shape of the cavity/space can be formed. The solid mass can be formed by curing the material with EM or UV radiation. The solid mass remains with little or no degradation at body temperature. Because the compositions described herein are flowable at temperatures slightly above room temperature, the cannula can be smaller gauge than those used with current systems. In an embodiment, the compositions can be administered with a 16 to 18 gauge cannula or needle.

In an embodiment, the solid mass does not leak after formation in the body. In an embodiment, the rigidity of the solid mass is substantially similar to that of bone. Because the solid mass bone cement described herein has similar mechanics to bone, the implant acts as an improved shock absorber and is less likely to cause further fractures. In an embodiment, the bone cements described herein are uniformly radiopaque. In an embodiment, the bone cements described herein have long or virtually unlimited working time. In an embodiment, the bone cements described herein have minimal or no monomer toxicity.

Embodiments Employing Flowable Thermoplastic Compositions.

The description and drawings herein, including the best modes, alternative embodiments and examples include methods having aspects of the invention of tissue and/or bone augmentation using polymer compositions for extrusion into a patient's body.

An embodiment provides a method of extruding a polymer composition into a patient's body, including augmenting a vertebral body of a patient's spine so as to stabilize and correct the effects of a compression fracture.

An embodiment provides a polymer delivery system for extruding a polymer composition into a patient's body, including a device for delivering a polymeric material to augment tissue (e.g., bone tissue) of a patient, such as a vertebral body.

An embodiment provides an example of a polymeric material suitable for augmenting and stabilizing soft tissue or bone in a patient's body.

In the devices and methods described and shown, a polymeric cement or augmenting composition may be employed configured to be delivered by manipulation of the thermo-mechanical state of the composition, without requiring further chemical alteration of the cement during or after delivery.

Also included are methods of repairing and/or stabilizing vertebral compression factures using polymer compositions for extrusion into a vertebral body.

Also included are methods of restoring vertebral height lost in a compression fracture using polymer compositions for extrusion into a vertebral body.

Also included are prostheses and methods of inserting, encapsulating, filling and/or inflating such prostheses within a body tissue, such as a vertebral body.

In an method embodiment of treating a lesion or fracture bone in bone tissue, the method may comprise the steps of:
  (a) providing a polymer composition comprising a side chain crystallizable polymer, wherein:
    (i) the polymer composition has a solid state when within a first temperature range, the first temperature range selected to substantially correspond to temperatures generally found in anatomical bone structures of living mammals, the solid state having mechanical properties suitable for supporting and/or augmenting a bone lesion or fracture;
    (ii) the polymer composition has a second transition temperature range, the second transition temperature range being above the first temperature range; and
    (iii) the polymer composition has an extrudable fluid state when in a third temperature range, the third temperature range being above the second temperature range; the third temperature range selected to correspond to therapeutically acceptable temperatures for the bone tissue being treated, the extrudable fluid state in the third temperature range having a viscosity sufficiently low to permit injection into the bone tissue being treated;
  (b) providing a polymer delivery system operatively configured to heat a quantity of the polymer composition to the extrudable fluid state within the third temperature range and operatively configured to inject the resulting fluid polymer composition into the bone tissue being treated;
  (c) administering the fluid polymer composition by operating the polymer delivery system so as to inject the fluid polymer composition at least partially into the bone tissue being treated; and
  (d) transforming the resulting injected fluid polymer composition to the polymer composition in the solid state by permitting cooling of the injected fluid polymer composition from within the third temperature range to within the first temperature range so as to configure the resulting solid polymer composition to provide support and/or augmentation to the bone lesion or fracture being treated.

In an embodiment of the method, the lesion or fracture is a compression fracture, and involves administering the fluid polymer composition by operating the polymer delivery system so as to inject the fluid polymer composition at least partially into the bone tissue being treated comprises injecting the fluid polymer composition so as to recover the effective volume of the bone tissue by exerting an expansion force. For example, in an embodiment, the bone tissue comprises at least a portion of a vertebral body and the recovery of the effective volume of the bone tissue comprises recovery of an effective height of the vertebral body. In various embodiments, the method includes the use of one or more prostheses configured for insertion into tissue being treated, and may further comprising: step (e) prior to step (c), inserting a prosthesis at least partially into the bone tissue being treated; and wherein step (c) includes at least partially encapsulating the prosthesis with the fluid polymer composition being injected; and wherein step (d) includes comprises providing at least part of the support and/or augmentation to the bone lesion or fracture being treated by configuring the solid polymer composition to provide at least one of support, fixation and/or isolation of the prosthesis within the bone tissue being treated.

Alternative prosthesis may be configured with voids or inflatable portions. An alternative method may comprise step (e) prior to step (c), inserting a prosthesis at least partially into the bone tissue being treated, wherein the prosthesis has an internal void; and wherein step (c) includes at least partially filing the internal void of the prosthesis with the fluid polymer composition being injected; and wherein step (d) includes providing at least part of the support and/or augmentation to the bone lesion or fracture being treated by configuring the solid polymer composition to provide support in the void of the prosthesis within the bone tissue being treated.

A further alternative method may comprise step (e) prior to step (c), inserting a prosthesis at least partially into the bone tissue being treated, the prosthesis including an internal portion capable of being inflated to create an internal inflation volume; and wherein step (c) includes one or more of: (i) inflating the internal portion by injecting the fluid polymer composition to create the internal inflation volume; (ii) inflating the internal portion to create the inflation volume independently of the injection of the fluid polymer composition, and (iii) at least partially filling the inflation volume with the fluid polymer composition; and wherein step (d) includes providing at least part of the support and/or augmentation to the bone lesion or fracture being treated by configuring the solid polymer composition to provide support in the internal inflation volume of the prosthesis within the bone tissue being treated. In spinal applications, the bone tissue may include at least a portion of a vertebral body and the prosthesis may be inserted at least partially within the vertebral body. Thus where the fracture or lesion is a compression fracture the inflation of the inflatable portion of the prosthesis is carried out so as to recover effective height of the vertebral body by exerting one or more expansion forces.

In a polymer composition embodiment for augmentation and support of anatomic tissue (e.g., bone tissue), the composition may comprise a side chain crystallizable polymer, wherein: (i) the polymer composition has a solid state when within a first temperature range, the temperature range selected to substantially correspond to temperatures generally found in anatomical structures of living mammals (e.g., anatomical bone structures), the solid state having mechanical properties suitable for supporting and/or augmenting anatomic tissue (e.g., bone tissue); (ii) the polymer composition has a second transition temperature range, the second temperature range being above the first temperature range; and (i) the polymer composition has a extrudable fluid state when in a third temperature range, the third temperature range being above the second temperature range; the third temperature range selected to correspond to temperatures known to be therapeutically acceptable for the anatomic tissue (e.g., bone tissue) being treated, the fluid state in the third temperature range having a viscosity sufficiently low to permit injection into the anatomic tissue (e.g., bone tissue) being treated. In an embodiment, the side chain crystallizable polymer comprises an amount of polar groups selected to increase the adhesion of the side chain crystallizable polymer to the bone tissue.

The polymer composition may further comprise a radioopaque additive. For example, the side chain crystallizable polymer may be inherently radiopaque, e.g., as described in U.S. Patent Application Publication Nos. 2006/0024266 and 2006/0182779, both of which are hereby incorporated herein by reference and particularly for the purpose of describing such polymers and methods for making them. The side chain crystallizable polymer of the composition may the include —$(CH_2)n$- groups in a side chain, where n is in the range of about 6 to about 30. In an embodiment, n may in the range of about 20 to about 30. The side chain crystallizable polymer is a copolymer comprising at least one recurring unit having an optional —$(CH_2)m$- group (e.g., side group) where m is in the range of about 0 to about 5; and at least one recurring unit having a —$(CH_2)n$- group (e.g., side group) where n is in the range of about 6 to about 30. In an embodiment, at least one of the recurring units is an alkyl methacrylate.

In further embodiments, a polymer composition having aspects of the invention may comprise a side chain crystallizable polymer that is a copolymer comprising two or more of the recurring units selected from the group consisting essentially of methyl methacrylate; ethyl methacrylate; hexyl methacrylate; and behenyl methacrylate. Note that industrially-available monomer mixtures may be cost effectively used in substitution without departing from the spirit of the invention, where the properties of the resulting copolymer are suitable, such as where the mixture is predominately of a selected monomer alkyl chain length. For example alkyl methacrylates may be supplied as a mixture within a specified range of alkyl chain lengths (e.g., alkyl ($C_{22}$-$C_{24}$)methacrylate monomer mixture, and the like).

In embodiments of the polymer composition the first temperature range (solid state) may between about 37° C. and about 41° C. In embodiments, the third temperature range may be between about 45° C. and about 100° C.; and in other embodiments, the third temperature range may be between about 50° C. and about 80° C.

In an method embodiment of performing a kyphoplasty procedure on a vertebral body, the method may comprise the steps of:

(a) inserting an inflatable balloon kyphoplasty device into the vertebral body;

(b) inflating the balloon kyphoplasty device so as to create an expansion void within the vertebral body and/or so as to recover effective height of the vertebral body by exerting expansion forces;

(c) providing a polymer composition comprising a side chain crystallizable polymeras described herein;

(d) providing a polymer delivery system operatively configured to heat a quantity of the polymer composition to the extrudable fluid state within the third temperature range and operatively configured to inject the resulting fluid polymer composition into the expansion void in the vertebral body;

(e) administering the polymer composition by operating the polymer delivery system so as to inject the fluid polymer composition into at least a portion of the expansion void in the vertebral body; and (f) transforming the resulting injected fluid polymer composition to the polymer composition in the solid state by permitting cooling of the injected fluid polymer composition from within the third temperature range to within the first temperature range so as to configure the resulting solid polymer composition to provide support to prevent collapse of the all or a portion of the expansion void in the vertebral body.

Embodiments Employing Biodegradable Osteoconductive and Osteoinductive Compositions.

Embodiments having aspects of the invention include structural alloplastic bone graft (SABG) materials comprising bioresorbable side chain crystallizable polymer compositions. The embodiments provide treatment that is exceptionally minimally invasive due to simple flow delivery, yet it provides a superior structural implant. Additionally, the SABG material may include osteoconductive and/or osteoinductive components of SABG which promote natural bone growth as the material degrades.

An embodiment of the SABG composition for augmentation, repair or fusion of bone, comprises (i) a biodegradable side chain crystallizable polymer having a first order transition above the body temperature of a patient, the polymer composition having a flowable property at a delivery temperature above the transition temperature, the delivery temperature sufficiently low to avoid damage to tissue adjacent a delivery site with the patient's body; (ii) an osteoconductive material; and/or (iii) an osteoinductive material.

BRIEF DESCRIPTION OF THE DRAWINGS

The following drawings are descriptive of aspects of the inventions herein:

FIGS. 16A through 16D show schematically an exemplary polymer cement delivery needle assembly having aspects of the invention, shown in both exploded and assembled configuration.

FIGS. 17A through 17C show schematically a method of inserting a delivery needle assembly having aspects of the invention, employing a cannula and trocar.

FIGS. 20 through 22A-B shows schematically several alternative exemplary embodiments of a polymer delivery needle assembly having aspects of the invention, further illustrating examples of polymer heat and transition profiles.

FIGS. 24A-C illustrate an example of copolymerization of monomers BHMA and MMA in selected proportions y:x w/w %.

FIG. 26 is a plot illustrating the rapid solidification characteristic of the polymer compositions of these examples.

FIG. 27 is a plot illustrating the ductility that can be achieved in the polymer compositions of these examples.

FIG. 28 is a plot illustrating the effect of a radio-opacity additive on the rheological properties of polymer compositions having aspects of the invention. FIG. 29A and FIG. 29B show the viscosity-to-temperature relationship of a series of example copolymer compositions at 60° C., 70° C., and 80° C.

FIG. 30A and FIG. 30B show the effect of molecular weight on viscosity over the temperature range of 60-80° C., for polymer compositions having aspects of the invention, using for an illustrative example a 70/30 w/w % BHMA/MMA copolymer.

FIG. 31A shows the effect of polymer composition on compressive strength, as contrasted with the strength of commercial bone cements and anatomic vertebra.

FIG. 31B compares two of the compositions in FIG. 31A (marked with asterisks *) with respect to the effect of substitution of a different monomer (HMA) for a portion of the MMA in two copolymer compositions which both comprise 70 w/w % BHMA.

DETAILED DESCRIPTION OF THE EMBODIMENTS

Side-Chain Crystallizable Polymers

Figure 1:
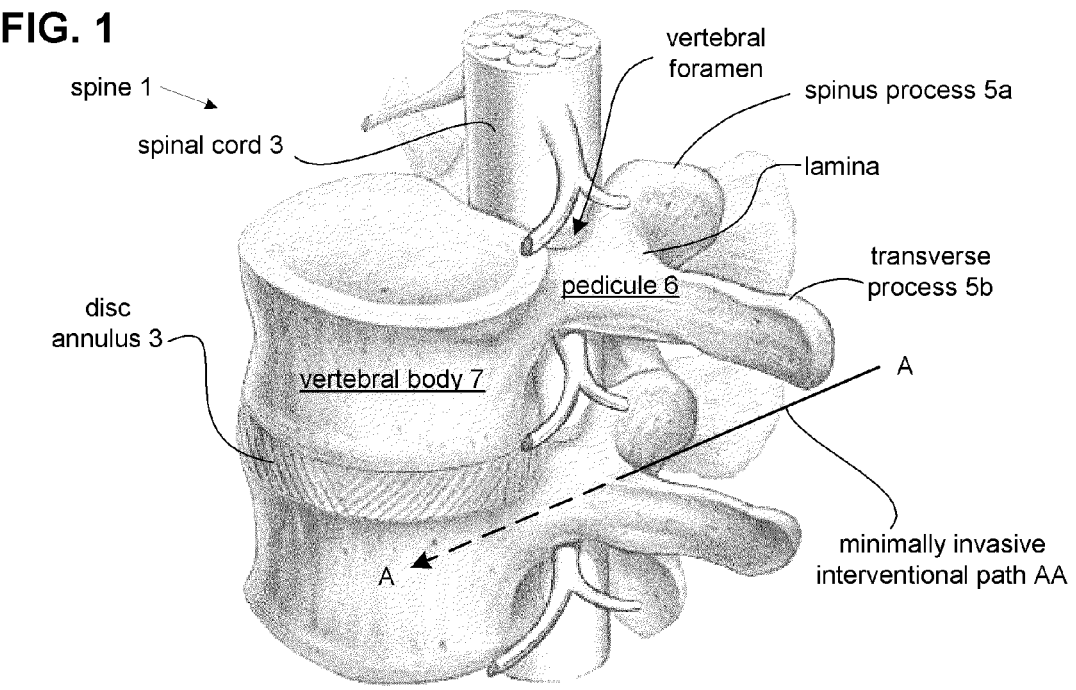
FIG. 1 shows a perspective view of the anatomy of a portion of a normal human spine.

Several types of monomers, oligomers, and polymers can be used in the methods described herein, including compounds and oligomers/polymers comprising recurring units described in U.S. Patent Application Publication Nos. 2006/0024266 and 2006/0182779, both entitled "Side-Chain Crystallizable Polymers for Medical Applications," both of which are hereby incorporated by reference in their entirety, but particularly for their disclosure of monomers, polymers, and methods of making thereof.

In an embodiment, the polymers, oligomers, and monomers described herein have crystallizable groups or side chains. The type, size, spacing and configuration of the groups or side chains (which may be referred to generally as crystallizable side chains herein) along the polymer backbone are preferably selected so that the polymer forms crystalline regions at selected temperatures. Those skilled in the art understand that any particular isolated side chain group is not considered to be crystallizable per se because side chain crystallization is a bulk characteristic of the polymer to which the side chains are attached. Thus, the extent to which side chains exhibit crystallinity when attached to a side chain crystallizable (SCC) polymer depends on the molecular configuration of the polymer as a whole. Various aspects of polymer side chain crystallization are discussed in greater detail in U.S. Patent Application Publication Nos. 2006/0024266 and 2006/0182779. Crystallizable side chains may comprise, for example, —(CH$_2$)n- and/or —((CH$_2$)n-O—), groups. The side chains are preferably linear to facilitate crystallization of the polymer. For polymers, oligomers, and monomers that contain —(CH$_2$)n- groups, n is preferably in the range of about 6 to about 30, more preferably in the range of about 20 to about 30. For polymers, oligomers, and monomers that contain —((CH$_2$)m-O—)n groups, n is preferably in the range of about 6 to about 30 and m is preferably in the range of about 1 to about 8. More preferably, m and n are selected so that the ((CH$_2$)m-O—)n groups contain from about 6 to about 30 carbon atoms, even more preferably from about 20 to about 30 carbon atoms.

The spacing between side chains and the length and type of side chain are preferably selected to provide the resulting polymer with a desired crystalline melting point. For example, for medical applications (e.g., embolotherapy), the spacing between side chains and the length and type of the side chains are preferably selected to provide the side chain crystallizable (SCC) polymer (and/or the material into which it is incorporated) with a melting point in the range of about 30° C. to about 80° C., more preferably in the range of about 40° C. to about 70° C. As the spacing between side chains increases, the tendency for the side chains to be crystallizable tends to decrease. Likewise, as the flexibility of the side chains increases, the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains.

Some examples of such polymers include versions of the following polymers that are selected so that the alkyl group is sufficiently long (e.g., greater than about 6 carbons) to provide the desired melting point and, for polymers modified to include heavy atoms, e.g., sufficient heavy atoms to render them radiopaque: poly(l-alkene)s, poly(alkyl acrylate)s, poly(alkyl methacrylate)s, poly(alkyl vinyl ether)s, and poly(alkyl styrene)s. Examples of side chain crystallizable polymers further include versions of the polymers disclosed in the following references that include (or have been modified to include) crystallizable side chains and, for polymers comprising heavy atoms, e.g., sufficient heavy atoms to render them radiopaque: U.S. Pat. Nos. 4,638,045; 4,863,735; 5,198,507; 5,469,867; 5,912,225; and 6,238,687; as well as U.S. Pat. No. 7,473,417, all of which are incorporated by reference in their entireties, and particularly for the purpose of describing side chain crystallizable polymers and methods for making them.

The polymers, oligomers, and monomers are not limited to those described above, and further include versions of known polymers that have been modified to include side-chain crystallizable groups and/or sufficient heavy atoms to render the resulting polymer radiopaque. Those skilled in the art will understand that such polymers may be prepared in various ways, e.g., by employing routine experimentation to modify known methods for making SCC polymers to thereby incorporate heavy atoms into the resulting polymers. For example, inherently radiopaque versions of the side chain crystallizable polymers described in U.S. Pat. No. 5,469,867 may be prepared by copolymerizing the corresponding monomers with monomers that contain heavy atoms. U.S. Pat. No. 5,469,867 is incorporated by reference and particularly for the purpose of describing monomers, polymers and methods of polymerization. See also in this regard the polymers, monomers, methods and examples described in PCT Publication Nos. WO2010/033640; WO2010-042918; and WO2010-042917, each incorporated herein by this reference.

Examples of suitable monomers that contain heavy atoms are disclosed in Kruft, et al., "Studies On Radio-opaque Polymeric Biomaterials With Potential Applications To Endovascular Prostheses," Biomaterials 17 (1996) 1803-1812; and Jayakrishnan et al., "Synthesis and Polymerization of Some Iodine-Containing Monomers for Biomedical Applications," J. Appl. Polm. Sci., 44 (1992) 743-748.

Heavy Atom Containing Side-Chain Crystallizable Polymers (HACSCCP's) may also be prepared by post-reaction, e.g., by attaching heavy atoms to the polymers described in U.S. Pat. No. 5,469,867.

Specific examples of SCC polymers that may be modified with heavy atoms to make HACSCCP's include:
(a) the acrylate, fluoroacrylate, methacrylate and vinyl ester polymers described in J. Poly. Sci, 10:3347 (1972); J. Poly. Sci. 10:1657 (1972); J. Poly. Sci. 9:3367 (1971); J. Poly. Sci. 9:3349 (1971); J. Poly. Sci. 9:1835 (1971); J.A.C.S. 76:6280 (1954); J. Poly. Sci. 7:3053 (1969); Polymer J. 17:991 (1985);
(b) corresponding acrylamides, substituted acrylamide and maleimide polymers (J. Poly. Sci.: Poly. Physics Ed. 11:2197 (1980);
(c) polyolefin polymers such as those described in J. Poly. Sci.: Macromol. Rev. 8:117-253 (1974) and Macromolecules 13:12 (1980);
(d) polyalkyl vinylethers, polyalkylethylene oxides such as those described in Macromolecules 13:15 (1980);
(e) alkylphosphazene polymers, polyamino acids such as those described in Poly. Sci. USSR 21:241, Macromolecules 18:2141;
(f) polyisocyanates such as those described in Macromolecules 12:94 (1979),
(g) polyurethanes made by reacting amine- or alcohol-containing monomers with long-chain alkyl isocyanates, polyesters and polyethers, polysiloxanes and polysilanes such as those described in Macromolecules 19:611 (1986); and
(h) p-alkylstyrene polymers such as those described in J.A.C.S. 75:3326 (1953) and J. Poly. Sci. 60:19 (1962).

The molecular weight of polymers and oligomers may be selected in view of the intended application for the polymer. For example, in some medical applications, e.g., for certain bone augmentation applications, it is desirable for the polymer or oligomer to flow easily at temperatures higher than the melting point and to form a solid at temperatures below the melting point. The viscosity of a molten material generally increases as the molecular weight of the material increases, and thus the molecular weight of a polymer or oligomer is preferably selected to provide the desired molten polymer viscosity. For example, a suitable molecular weight range for oligomers may be in the range of from about 200 to about 5,000. A suitable molecular weight range for the polymers may be in the range of from about 5,000 to about 250,000. Molecular weights are weight average as determined by high pressure size exclusion chromatography using light scattering detection.

Spinal Compression Fractures and/or Bone Treatment Devices and Methods

It should be understood that the devices, compositions and methods described herein are generally applicable to the repair, treatment and/or augmentation of anatomical bone structures in which lesions, fractures or defects exist. The examples described and shown in the present application and in the applications incorporated by reference with respect to vertebral fractures may be adapted to these other treatment objectives without departing from the spirit of the invention.

FIG. 1 shows a perspective view of the anatomy of a portion of a normal human spine, and depicts an adjacent pair of vertebrae, such as thoracic vertebrae, in relation to the adjacent spinal discs and spinal cord anatomy. Several bony processes extend in the dorsal direction to form a vertebral foramen encircling the spinal cord. The portion of the process structure comprising the pedicle and adjacent lamina between the transverse and spinal process provides a conventionally-used minimally invasive path for insertion of biopsy or treatment probes into the internal volume of the vertebral body without compromising the spinal cord.

Figure 2A:
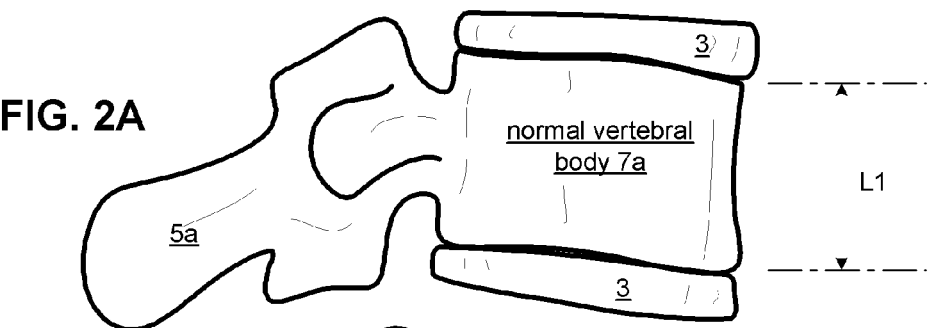
FIGS. 2A and 2B show in side view a pair of human vertebral bodies, in FIG. 2A a normal vertebral body and in FIG. 2B a vertebral body injured by compression fracture.
Figure 2B:
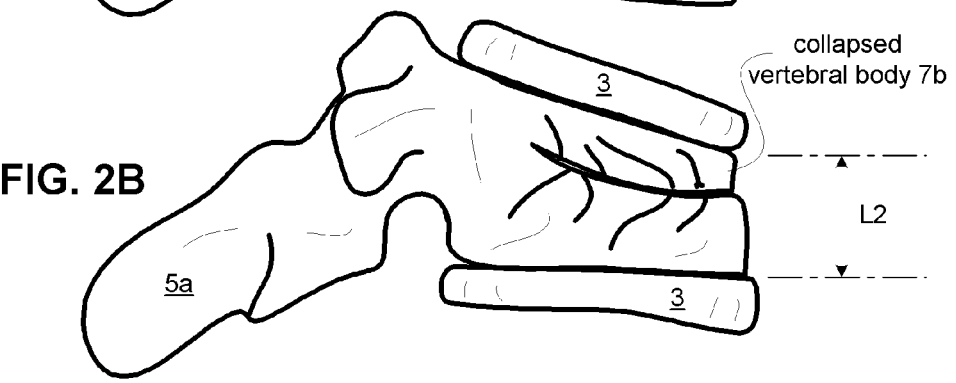

FIGS. 2A and 2B show in side view a pair of human vertebral bodies, in FIG. 2A a normal vertebral body and in FIG. 2B a vertebral body injured by compression fracture. Note that typically the fracture produces a distortion of the body to a wedge shape, with a reduced height on the ventral side (L2 vs L1).

Compositions Examples with Precursor for In-Vivo Reaction.

The mixtures described herein have improved properties upon curing with visible light or UV radiation. Embodiments of the bone cements described herein have structural stability substantially equal to commercial bone cements, as preferred embodiments of the bone cements described herein do not deform or exhibit less deformation upon the influences of long term exposure to stresses. Low molecular weight species can be included in the compositions described herein. Some latent photo cross-linkable adaptations of the non-resorbable polymers from U.S. Patent Application Publication Nos. 2006/0024266 and 2006/0182779 are as follows:

Example 1

SCC acrylic/methacrylic ester copolymers w/an inherently radiopaque moiety (e.g., iodostyrene) plus a copolymerized UV crosslinkable monomer such as acryloyl benzophenone (ABP). The polymer undergoes a melting phase change as it exits the heated delivery tip. Once the heated material has cooled and recrystallized in place, UV radiation initiates a cross-linking reaction in the photo-initiator to form a non-flowable mass. The polymer is poly(octadecyl methacrylate-co-4-iodostyrene-co-acryloyl benzophenone).

Example 2

Reactive oligomeric mass comprised of the same composition as in Example 1, but only of oligomeric molecular weight. The oligomer undergoes a melting phase change as it exits the heated delivery tip. However, the oligomer flows at a much lower viscosity because of the lower molecular weight.

Example 3

The monomers used to make the polymer in Example 1 or the oligomer in Example 2 can also be used in place of those materials but in the form of as a reactive, non pre-polymerized, paste.

Each of these mixtures is stable and may be pre-mixed long before the surgical treatment begins. In an embodiment, the compositions are stable for weeks, months, and even about 20 years or more.

Administration into a Compression Fracture.

Figure 3A:
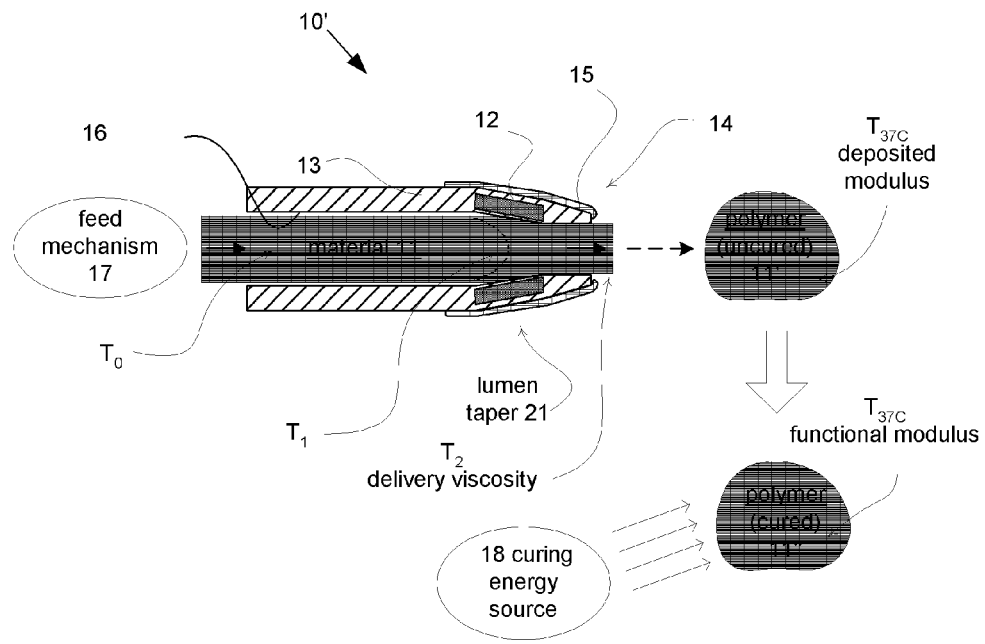
FIG. 3A shows a schematic cross-section of an exemplary device having aspects of the invention for delivering an augmentation material to a portion of a human body, wherein the material is cured by an energy source subsequent to deposition within the body.

As illustrated in FIG. 3A, a rod-shaped material 11 (e.g., a rod of generally circular cross-section) at an initial temperature T0 is pushed by feed mechanism 17 through the delivery lumen of a trocar 10' into an internal body space (such as vertebral body space). The distal end or tip of the trocar 10' is adapted to provide thermal input to the material by heating source 12 (e.g., a resistive heater), the tip being optionally covered by a heat shield 15 (e.g., ceramic molding). The heat source 12 raises the temperature of material 11 to a transition temperature T1 as the material passes towards the distal tip 14, reducing the viscosity or modulus to enhance flowability. The trocar 10' may have a tapered tip 21 to assist in delivery control.

Figure 5A:
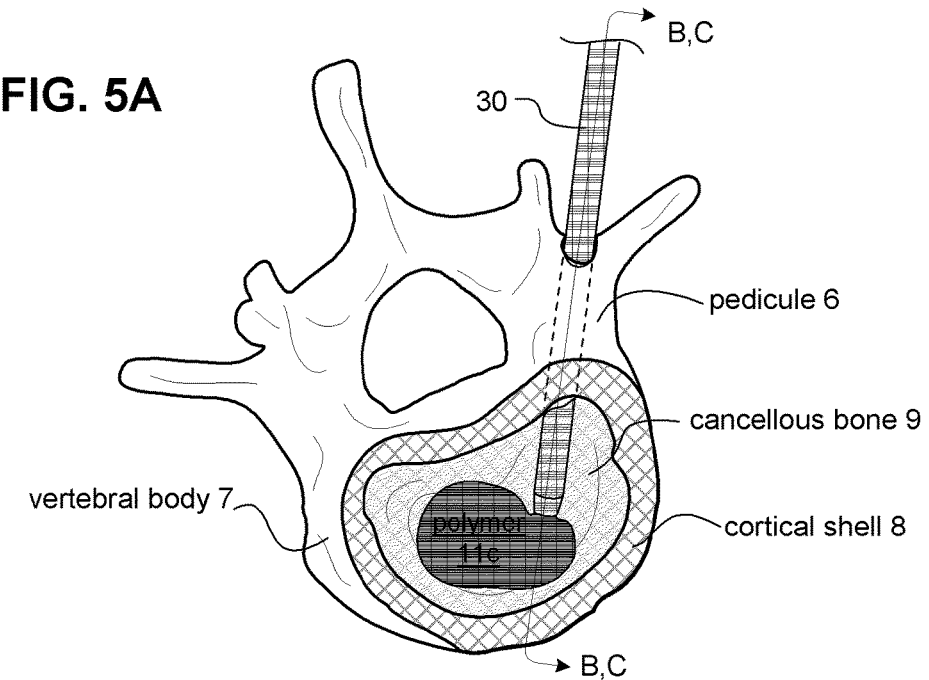
FIGS. 5A-5C illustrate schematically an exemplary method of stabilizing and/or correcting a spinal compression fracture.
Figure 5B:
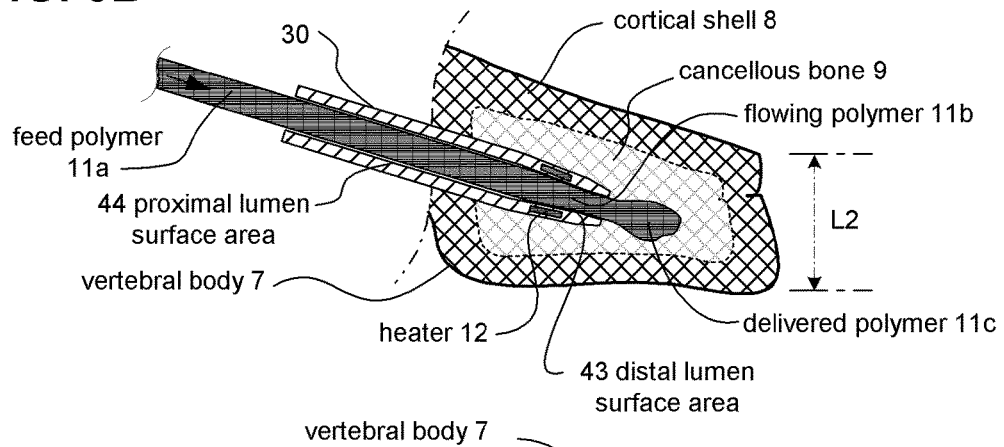
Figure 5C:
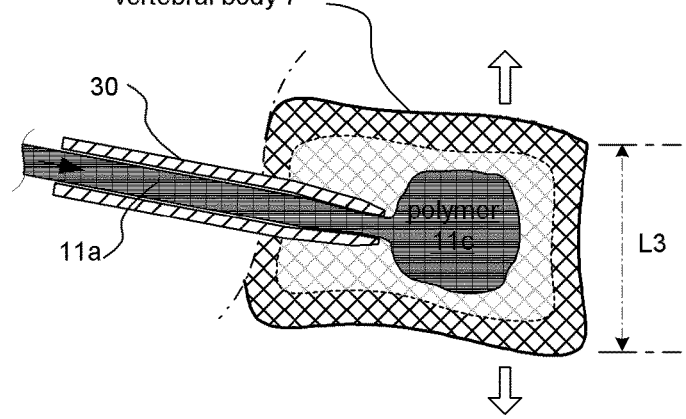

FIGS. 5A-5C show schematically a delivery trocar or cannula as inserted into a vertebral body of a patient, depicting the delivery route of a fracture repair composition having aspects of the invention. See further description of FIGS. 5A-C, below.

In a self-contained hand-held unit, for example, the feed mechanism may include a trocar mounting handle which includes a feed lever/ratchet mechanism applying manual force to the rod 11 at the proximal end of trocar 10'. Optionally, the delivery temperature of the material can be read at an output display at the handle for user feedback.

The material rod may be delivered to the body space as a molten mass 11c which then resolidifies at body temperature T3 to have a deposited modulus or viscosity. In an embodiment, the material 11 is a curable polymer, such that after the material 11c has been delivered into the delivery space, the portion of non-delivered material rod 11 is removed and curing energy source is inserted into the trocar to expose the deposited material to curing energy (see curing energy source 18 in FIG. 3A). For example, a fiber-optic rod may be inserted to or beyond the trocar tip, so as to delivery UV radiation to the deposited material. The curing energy changes the material 11c to a final functional or structural modulus. An example material for this would be a preformed SCC-based polymer with latent reactive olefinic moieties blended with ethylene glycol dimethacrylate and a standard photo-initiator. Alternatively, (meth)acrylate monomers having various alkyl chain lengths can be used, including carbon chain lengths in the range of about 6 to about 30.

An example method having aspects of the invention for treating a compression fracture, may comprise: (a) providing a stable composition including (i) a polymer, oligomer, and/or monomer that comprises a crystallizable side chain, (ii) a polymer, oligomer, and/or monomer that is inherently radiopaque, and (iii) a polymer, oligomer, and/or monomer that comprises a latent photo-initiated free-radical cross-linking moiety; (b) administering the composition to a patient at a treatment space (e.g., within a vertebral body); and (c) subsequently initiating the free-radical cross-linking reaction.

In an alternative method example, the method may comprise (a) providing a stable composition including (i) a polymer, oligomer, and/or monomer that comprises a crystallizable side chain, (ii) a polymer, oligomer, and/or monomer that is inherently radiopaque, and (iii) a polymer, oligomer, and/or monomer that comprises a free radical initiation moiety; (b) administering the composition to a patient at a treatment space (e.g., within a vertebral body); and (c) subsequently initiating a free-radical linking and/or cross-linking reaction.

Additional exemplary embodiments may include a radio-opaque additive substance, such as barium sulfate or the like. In addition, additional additive materials may be included to modify physical characteristics such as plasticizers, fillers, and the like. In addition, additional bioactive materials may be included such as pharmaceutical agents, and the like.

Treatment Devices, Methods and Examples Employing Thermoplastic Compositions.

Figure 3B:
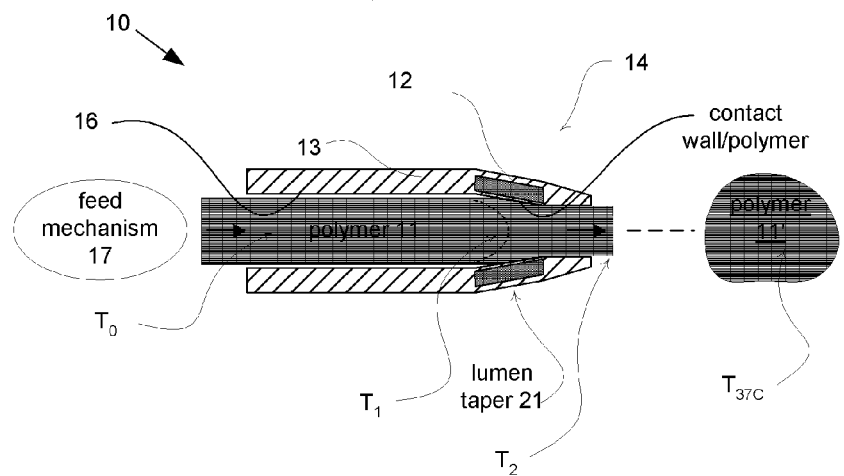
FIG. 3B shows a schematic cross-section of an exemplary device having aspects of the invention for delivering a thermoplastic augmentation material to a portion of a human body, including a heat source in a distal portion of the device.

FIG. 3 shows a schematic cross-section of an exemplary device (delivery probe or needle 10) having aspects of the invention for delivering a augmentation material to a portion of a human body, including at least one heat source 12 in a distal portion of the device. Those skilled in the art will understand that in this embodiment, the polymer 11 is a thermoplastic.

In longitudinal order, the proximal end of needle 10 communicates with a feed mechanism 17 for polymer line 11. Feed mechanism 17 advances the thermoplastic polymer line or column through a lumen formed by needle wall 13, having sufficient clearance for sliding motion, but which preferably provides support against polymer column buckling. As fed into the needle 10, the polymer 11 is at state $T_0$, which has a sufficient modulus to support substantial compression forces, (e.g. glassy, semi-crystalline, etc.).

As the polymer column 11 is advanced near the distal tip, the central lumen is tapered so as to bring the polymer in contact with the needle wall 13, generating resistive force. Heat source 12 (e.g., resistance, RF, US, fiber-optic laser, etc.) heats the polymer adjacent the point of contact to approach a temperature $T_1$. As is more particularly shown in FIGS. 6-9, the heating induces a heat-triggered transition (1st or 2nd order) which substantially reduces the polymer storage modulus or viscosity, so as to permit plastic or fluid flow distally through the needle tip. In effect, where the lumen taper is sized to prevent polymer advancement at the polymer modulus or compressive strength corresponding to the feed temperature $T_0$ (e.g., about 20° C.), further polymer advancement is dependent upon a heat-triggered transition in response to the action of the heater 12 (e.g., as the polymer approaches a temperature of T1, such as from about 45° C. to about 100° C.).

Note that device 10 may include multiple heat sources providing more than one discrete longitudinal temperature zones, which may be separately controllable or adjustable. Note that the terms "extruded" and "injected" may be used interchangeably in this application in reference to polymer material delivered on or into a patient's body, without implication as to a particular physical state (e.g., solid, semi-solid, plastic, rubbery, liquid or the like).

The heated polymer 11 is extruded from the distal tip at a temperature $T_2$ and a corresponding delivery viscosity. After extrusion to a location within a patient's body, such as within a vertebral body, the polymer 11' cools to body temperature, indicated as $T_{37C}$-functional state, having support modulus.

As is more particularly shown in FIGS. 6-9, the polymer 11 may have a composition providing selected thermomechanical properties permitting the mechanical state to be determined by a combination of temperature and transition time. In an exemplary mode of operation, the device 10 may be controlled by a manual or automatic controller including regulation of one or more of the following functionally interrelated parameters: polymer feed force; polymer feed velocity; heater wall temperature; and/or heater output power.

Thus, for example, for a given heater wall temperature, a increased polymer feed force will tend to overcome flow resistance when the heated polymer is at a relatively lower temperature, thus allowing extrusion (T2) of a cooler and consequently more viscous polymer state.

Conversely, a lower feed force will tend to keep a given incremental volume of polymer in contact with heater 12 for a longer period (slower extrusion rate) so as to overcome flow resistance when the polymer is at a relatively higher temperature, thus allowing extrusion (T2) of a hotter and consequently less viscous polymer state.

Similarly, it will be seen that, for a constant polymer feed velocity, regulation of the heater energy output will tend to regulate the extrusion temperature T2, so as to adjust delivery viscosity. Thus, the delivery parameters may be adjusted relative to a given composition of polymer 11 to produce a selected extrusion temperature, viscosity and/or volume flow rate.

Note that the inner wall of the proximal portion of needle 10 may be coated with an agent such as a fluorocarbon resin, if desired, to minimize friction with polymer 11 in the feed state temperature $T_0$. The polymer-to-wall clearance selected to provide low-friction sliding without binding, while providing the relatively thin column of polymer 11 with effective support against bucking compression failure.

Figure 11:
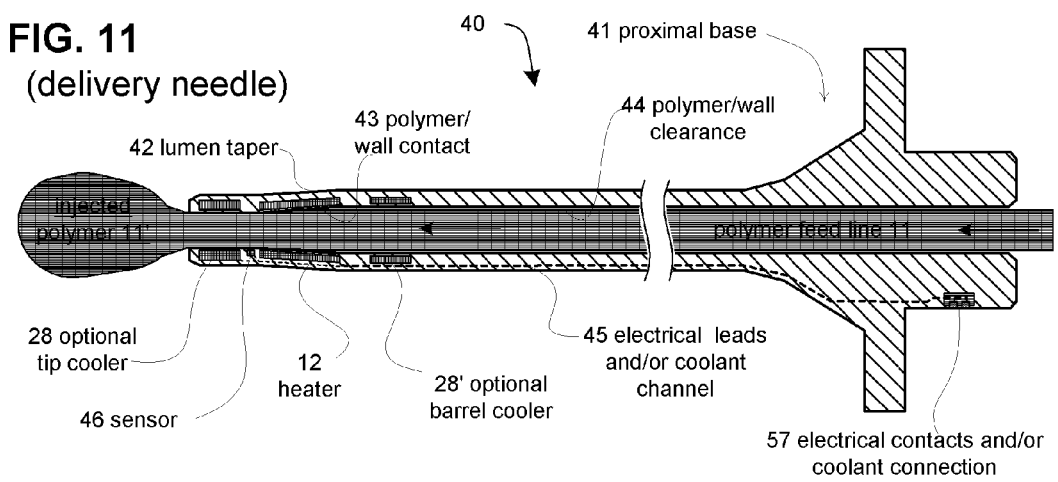
FIG. 11 is a detail schematic drawing further showing both proximal and distal ends of the delivery needle of FIG. 10.

It may be seen that a polymer composition may be selected so that in a high-modulus state (e.g., glassy amorphous above Tg, semi-crystalline, or a combination of those), substantial compressive forces may be generated by a suitably configured feed mechanism acting on the polymer column (see, for example, FIG. 11). The polymer column or line compressive forces may be adjusted as described so as to provide a selected extrusion pressure at the anatomic point of polymer deposition, such as within a vertebral body.

Figure 4A:
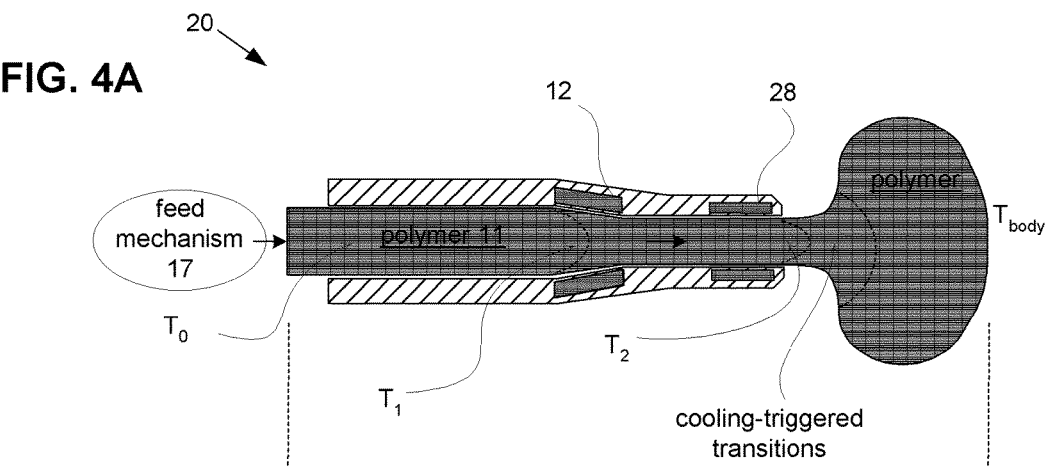
FIG. 4A shows a schematic cross-section of an exemplary device having aspects of the invention for delivering an augmentation material to a portion of a human body, including both a heat source and a cooling source in a distal portion of the device.
Figure 4B:
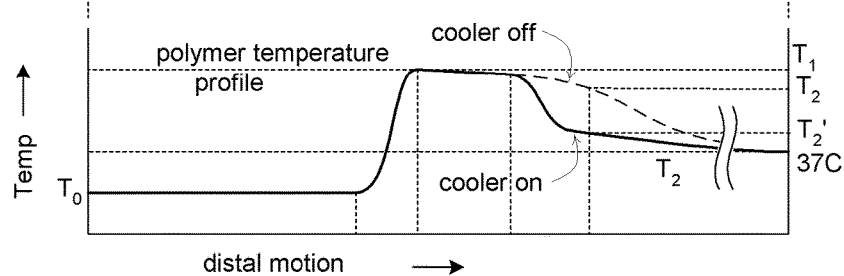
FIG. 4B is a plot depicting an exemplary longitudinal temperature profile along the central axis of the device of FIG. 4A.

FIG. 4A shows a schematic cross-section of an exemplary device (delivery needle 20) having aspects of the invention for delivering a augmentation material (e.g., polymer 11) to a portion of a human body, including both a heat source 12 and a cooling source 28 in a distal portion of the device. FIG. 4B is a plot depicting an exemplary longitudinal temperature profile along the central axis of the device of FIG. 4A. The configuration of device 20 is substantially similar to device 10 of FIG. 3B, and further includes at least one cooling source or cooler 28 (e.g., fluid cooling, miniature Peltier stack, etc.) mounted to chill the needle wall. In the case shown, the cooler 28 is adjacent the distal tip opening of the needle lumen, although alternatively or additionally coolers may be in a central or proximal portion of needle 20.

The plot of FIG. 4B shows the longitudinal temperature profile along device 20 and within treated tissue, showing a dashed line in the case of the cooler being off. The polymer temperature may be seen to increase from feed temperature T0 to T1 as it crosses the heat source 12. As the polymer approaches the distal tip with the cooler 28 in the "off" state (dashed line) the temperature exits the distal tip at temperature T2 (close to T1). As the extruded polymer cools upon deposition within the body, the terminal temperature is indicated as body temperature or T37 C. With the cooler in the "on" state, the polymer is seen to be chilled to a lower exit temperature of T2'. The regulation of cooler 28 permits the exit temperature to be adjusted relatively independently from flow rate or delivery pressure, and permits optimization of cooling-triggered transitions (e.g., nucleated re-crystallization, etc.). A tip cooler may also be used to chill the polymer prior to withdrawing the device 20 from the patient's body, so as to promote a clean "break" of the extruded polymer from the residual polymer within the needle. In another embodiment, a cooler may be used to chill the polymer feed column 11 proximal to the heater 12, so as to maintain a selected feed state modulus or rigidity (T0).

FIGS. 5A-5C illustrate schematically an exemplary method of stabilizing and/or correcting a spinal compression fracture. A device 30 (such as one of devices 10 or 20) is shown inserted into the vertebral body along an intervention path such as path A-A shown in FIG. 1, so as to extrude at least one bolus of polymer into the internal volume of the vertebral body. A typical human vertebral body comprises a hard outer shell of cortical bone (cortex) and a relatively softer, less dense portion of cancellous bone. Cancellous bone is a two-phase material comprising of porous solid material and fluid which fills the voids of the porous solid, the fluid typically occupying a large majority of the cancellous bone volume.

As may be seen in the pair of drawings of FIGS. 5B and 5C, in the methods, polymer compositions and devices described herein and having aspects of the invention, the extruding polymer 11c may exert sufficient force to partially or fully re-expand the collapsed vertebral body structure (see arrows in FIG. 5C), as is indicated by the increase in vertebral body height for L2 to L3. As described herein, the device control parameters and composition may be adjusted to provide a highly viscous bolus of extruded polymer 11c under a high extrusion pressure, thus providing sufficient force to re-expand the fractured vertebral body. The volume of polymer 11c depends on the vertebra size and condition of fracture. Typically a polymer volume of less than one to a few cubic centimeters is sufficient. The patient is preferably treated in a prone position, removing the compressive force of body weight on the vertebra during this procedure. The polymer viscosity as delivered into the vertebral body may be regulated so as to only minimally displace the fluid within the cancellous bone structure, causing the bolus of extruded polymer to effectively push upon the cancellous bone material in the fractured portion of the vertebral body, so as to apply a restoring or re-expanding force.

As described above with respect to FIG. 3B, the thermo-mechanical transition (softening) occurring at the point of contact of the polymer column 11 with the heated needle wall 12 at the entry to tapered portion of lumen acts as a "seal", in effect, to prevent backflow of softened or melted polymer in a proximal direction within the needle lumen. This sealing effect of the lumen taper against the feed polymer column permits a high delivery pressure to be exerted by the extruding polymer. The device 30 may be stabilized with respect to the vertebral body so as to counter extrusion pressure exerted by the polymer. For example, the needle may be anchored by external supports (mechanical or manual), or may be anchored to the vertebral body itself, such as by attachment to a cannula anchored to the vertebral bone. See, for example, the threaded cannula described in the incorporated Patent Application Publication No. US 2006-0142779.

FIGS. 6 through 9 are plots showing the thermo-mechanical properties of several examples of polymers which may be employed with the methods and devices described herein. For each figure, temperature is plotted versus storage modulus. Storage modulus is a modulus of elasticity accounting for frequency-dependent viscoelastic effects (elastic stored energy of deformation in contrast to viscous dissipation of heat). This permits a wide range of mechanical states of a polymer or other material to be usefully compared.

In general, modifications may be made to the chemical composition, method of polymerization or co-polymerization, blending or alloying, additives, manufacturing processing, annealing, quenching and the like which can be used to modify the specific properties of a particular example material within a range of generally similar polymers. For example, the glass transition temperature Tg, an important characteristic of amorphous polymers, is affected by compositional changes, rotational movement along polymer chains, chain flexibility, steric or configurational effects, and molecular weight or chain length. Likewise, the melting temperature of a polymer may be affected by crystallinity, symmetry, intermolecular bonding, tacticity, branching, and molecular weight. For this reason, FIGS. 6 through 9 show generalized properties, it being understood that the particular temperatures of transitions and the particular storage modulus values may vary widely within a class of polymer, as determined by routine experimentation informed by the guidance provided herein.

Figure 6:
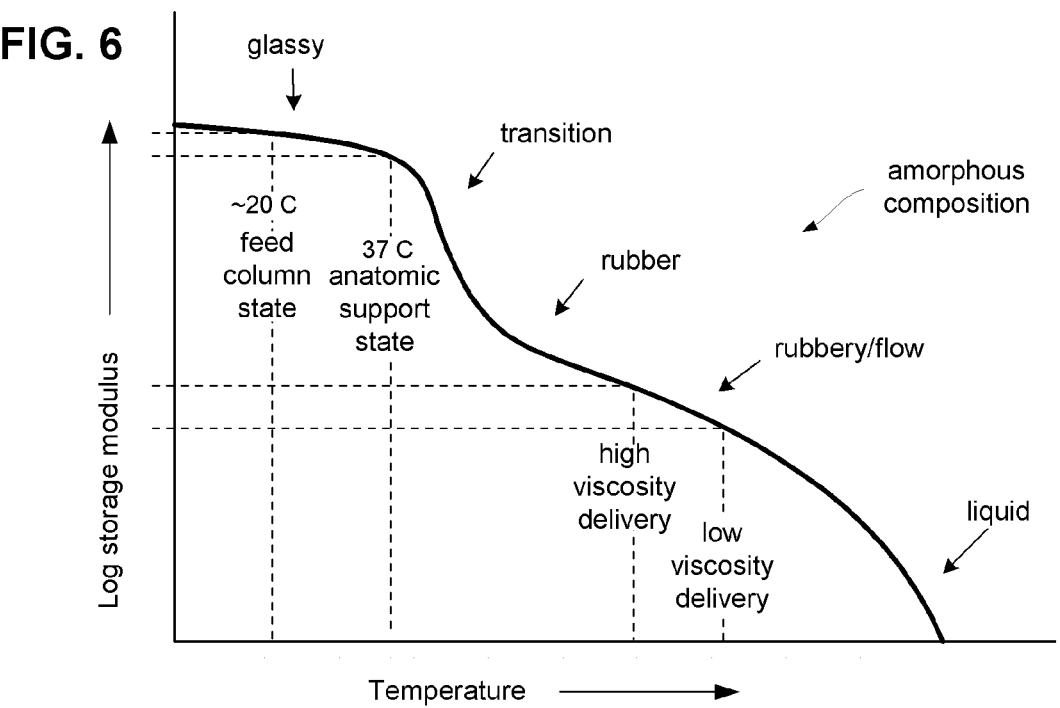
FIG. 6 shows a plot of thermo-mechanical properties of an exemplary composition suitable for treatment methods having aspects of the invention comprising a generally amorphous thermoplastic.

FIG. 6 shows a plot of thermo-mechanical properties of an exemplary composition suitable for treatment methods having aspects of the invention comprising a generally amorphous thermoplastic material. It may be seen that as temperature increased, the storage modulus (shown on a log scale) generally decreases. Beginning in a glassy state at low temperatures, as temperature increased the material passes successively through a glass transition (2nd order transition), a rubber plateau, a region of rubbery/flowable state and finally a melted or liquid state.

In the example shown, the anatomic support state is indicated as the modulus corresponding to a sustained temperature of the human body (~37° C.), which provides the functional state of the bone and tissue augmentation material. From the plot, a column feed temperature may be selected (~20° C.) with a corresponding storage modulus. Note that the feed temperature need not necessarily be the ambient temperature of the clinical location, as the feed polymer may be refrigerated or the like. Similarly, delivery temperatures may be selected at a desired storage modulus corresponding to a desired viscosity or softness as extruded into the treatment location (e.g., vertebral body). In this example, a higher viscosity delivery temperature (e.g., about 60-75° C.) and a lower viscosity delivery temperature (e.g., about 75-85° C.) are indicated by dashed lines.

Figure 7:
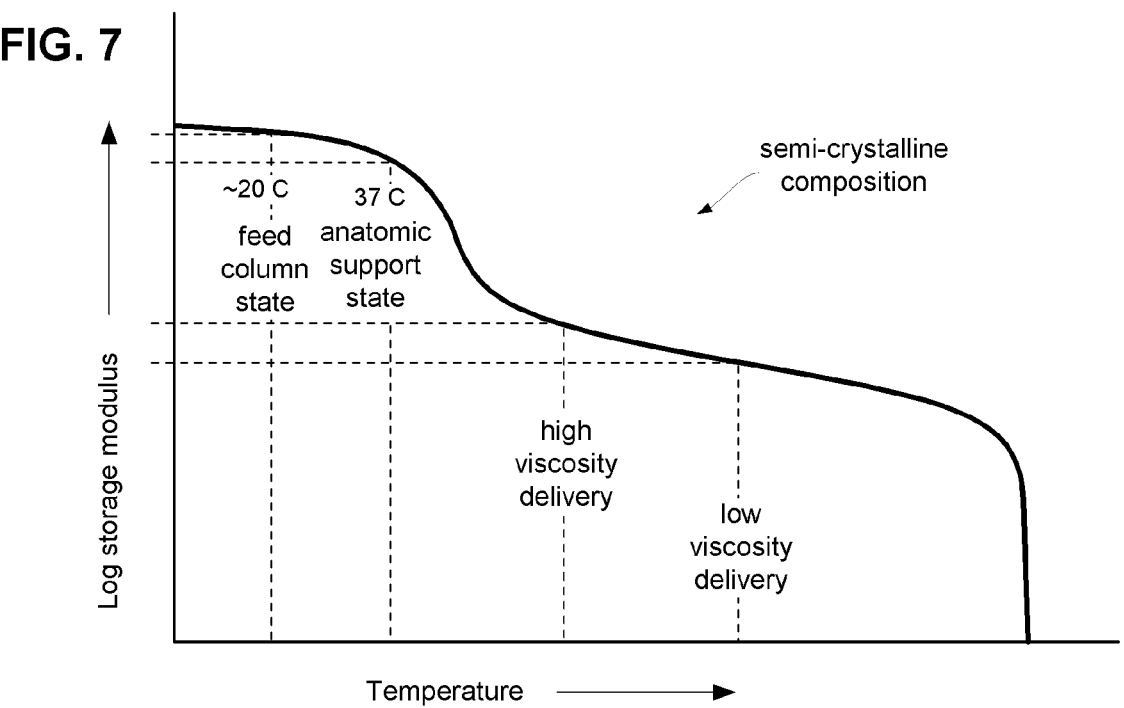
FIG. 7 shows a plot of thermo-mechanical properties of an exemplary composition suitable for treatment methods having aspects of the invention comprising a generally semi-crystalline thermoplastic.

FIG. 7 shows a plot of thermo-mechanical properties of an exemplary composition suitable for treatment methods having aspects of the invention comprising a generally semi-crystalline thermoplastic. A semi-crystalline polymer typically has a more abrupt melting point (first order transition) than an amorphous polymer. Exemplary high and low viscosity temperatures are indicated by dashed lines.

Figure 8:
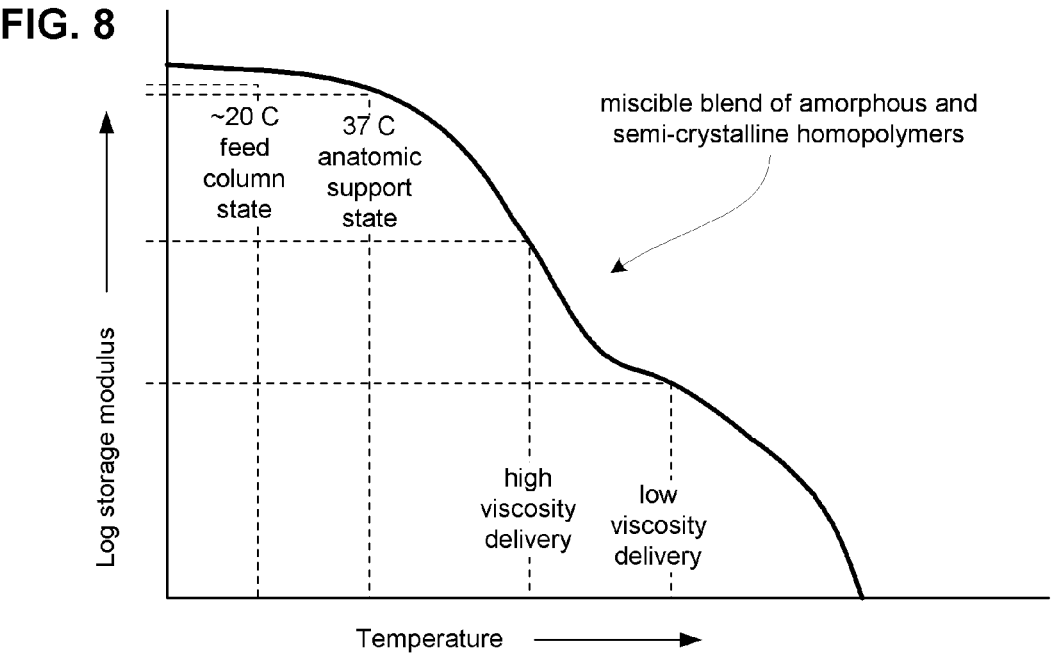
FIG. 8 shows a plot of thermo-mechanical properties of an exemplary composition suitable for treatment methods having aspects of the invention comprising a miscible blend of amorphous and semi-crystalline thermoplastic homopolymers.

FIG. 8 shows a plot of thermo-mechanical properties of an exemplary composition suitable for treatment methods having aspects of the invention comprising a miscible blend of amorphous and semi-crystalline thermoplastic homopolymers. Such polymer systems may be adjusted by variations in the percent composition of the constituent blend. See the incorporated PCT publication WO 2004-014449 for examples of such polymer systems. Exemplary high and low viscosity temperatures are indicated by dashed lines.

Figure 9:
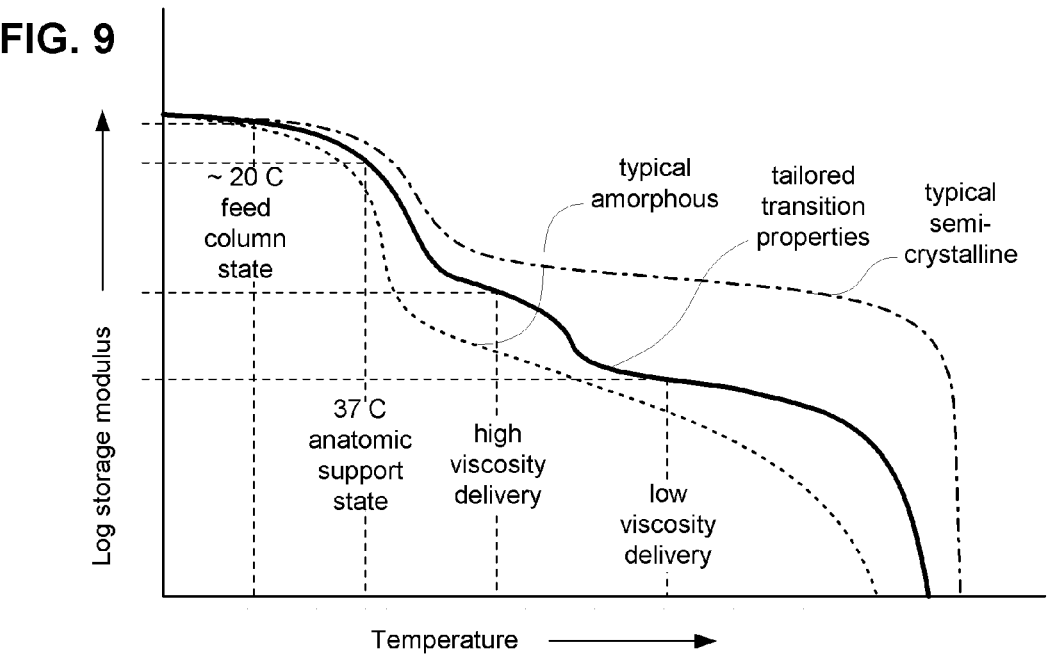
FIG. 9 shows a plot of thermo-mechanical properties of an exemplary composition suitable for treatment methods having aspects of the invention having tailored transition stages and comprising a side-chain crystallizable polymer.

FIG. 9 shows a plot (solid line) of thermo-mechanical properties of an exemplary composition suitable for treatment methods having aspects of the invention having tailored transition stages and comprising a side-chain crystallizable polymer. See the above incorporated co-assigned U.S. Ser. No. 11/335,771 (US 2006-0024266) and Ser. No. 11/176,638 (US 2006-0182779), each entitled "Side-chain crystallizable polymers for medical applications" for examples and methods of making such polymer compositions. Such polymers may have multiple transition points, influenced by the crystallinity of the side chain portions of the polymer chains as well as by the properties of the primary polymer chain (as well as by blended or added materials in the composition). This permits a polymer to have tailored thermo-mechanical properties making them particularly suitable for applications in which the composition that undergoes a transition upon a change in temperature spanning the temperature of a patient's body, and in which viscosity or softness is desirably adjusted over a range a few tens of degrees above body temperature. In FIG. 9, comparison plots are included shown the properties of typical amorphous (dotted line) and semi-crystalline polymers (dash-dot) having a similar solid modulus.

Figure 10:
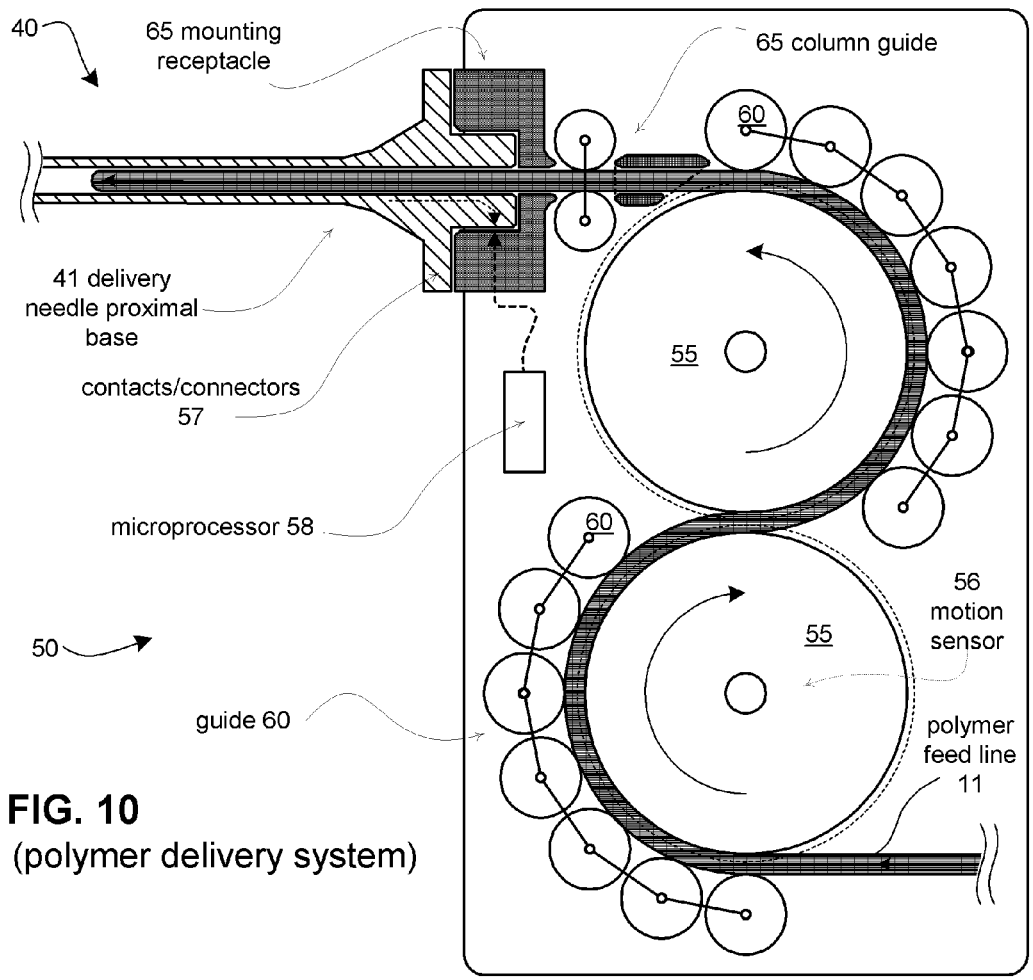
FIG. 10 shows schematically an exemplary polymer delivery system having aspects of the invention comprising a mating delivery needle (a proximal portion of the delivery needle is shown).

FIG. 10 shows schematically an exemplary polymer delivery system 50 having aspects of the invention comprising a mating delivery needle 40 (a proximal portion of the delivery needle is shown). FIG. 11 is a detail schematic drawing further showing both proximal and distal ends of the delivery needle 40 of FIG. 10.

In the example shown, the polymer line 11 is engaged by a pair of grooved friction drive pulleys or wheels 55, the engagement being secured by a series of compression or spring-loaded rollers 60. The drive wheels may be manually driven (e.g., by a physician via a hand grip mechanism) or may be power driven. A motion sensor may be included to acquire rate data and the like. In the example shown, additional rollers and guides are included to provide lateral support to the polymer line as it enters a delivery needle mounting receptacle or column guide 65. The geometry of the drive device may be adjusted to suit particular polymer line properties, such as diameter, stiffness, desired delivery pressure and the like. Note also that a number of alternative polymer line mechanical feed mechanisms may be included other than the device shown in FIG. 11 without departing from the spirit of the invention.

The delivery needle mounting receptacle 65 may be configured to engage and securely support (e.g., by a locking mechanism) the delivery needle 40 at the proximal needle base. The needle 40 may be substantially similar to the examples shown in FIGS. 3B and 4A-B. In the example shown in FIGS. 10 and 11 the needle comprises a heat source or heater 12 adjacent a distal lumen taper 42, and also optionally may include additional heating or cooling elements (a pair of coolers are shown distally and proximally adjacent the heater). Optionally and advantageously, the needle may include one or more temperature and/or pressure sensors (e.g. thermistors) to permit the temperate and/or pressure data to be acquired on a real-time basis. The needle 40 includes a longitudinal channel or conduit for electrical leads and/or coolant lines extending from the distal tip to the proximal base. The receptacle 65 guides the driven polymer line into the lumen of needle 40 and also may include electrical contacts and/or coolant connections configured to communicate with the corresponding electrical leads and/or coolant lines in the needle base. The system 50 advantageously may include a microprocessor and associated power sources, input-output devices, and/or displays. The microprocessor and associated sensors may provide heater/cooler controls, line drive controls and user tactile feedback. The microprocessor and associated devices may provide visual, tactile or audio display to a user of delivery temp, heater power, polymer velocity, pressure, cumulative delivered polymer volume, and the like.

FIGS. 12A through 12I are a series of nine generally similar transverse cross-sectional drawings of a human thoracic vertebral body, depicting related steps of an exemplary method of treatment having aspects of the invention. Common anatomic features are shown in each figure, and the devices or materials shown typically appear in more than one sequential drawing. Although the steps may advantageously be carried out in the sequence in order of the figures, they need not be.

Figure 12A:
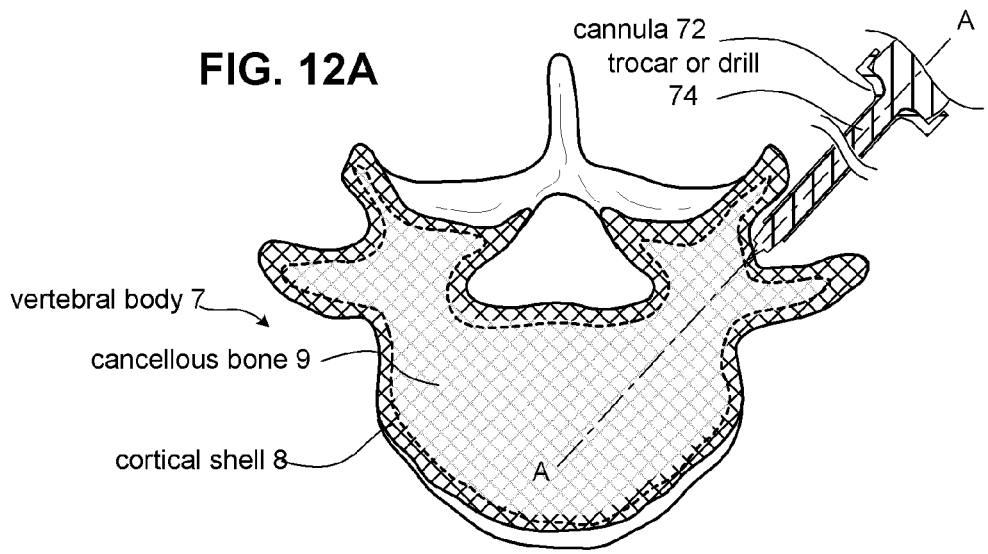
FIGS. 12A through 12I are a series of nine generally similar transverse cross-sectional drawings of a human thoracic vertebral body, depicting steps of an exemplary method of treatment having aspects of the invention.

FIG. 12A shows the vertebra together with a cannula/trocar assembly 72, 74, engaging the bone surface along a minimally invasive path A-A such as that shown in FIG. 1. The trocar 74 may include a drilling or cutting tool, and the cannula/trocar assembly is configured to puncture, cut and/or drill a bore hole along path A-A so as to insert the cannula into the vertebral body.

Figure 12B:
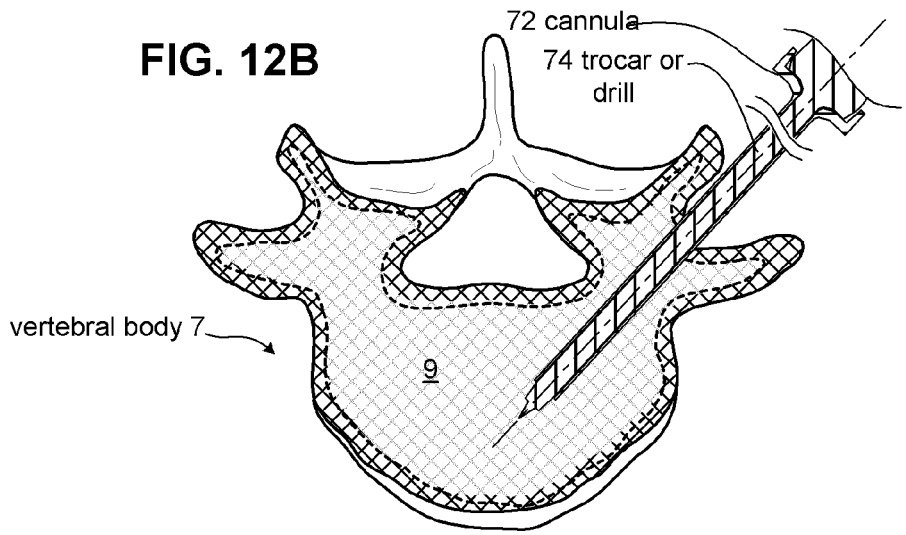

FIG. 12B shows the vertebra of FIG. 12A with the cannula/trocar assembly 72, 74 advanced into the cancellous bone central volume of the vertebral body.

Figure 12C:
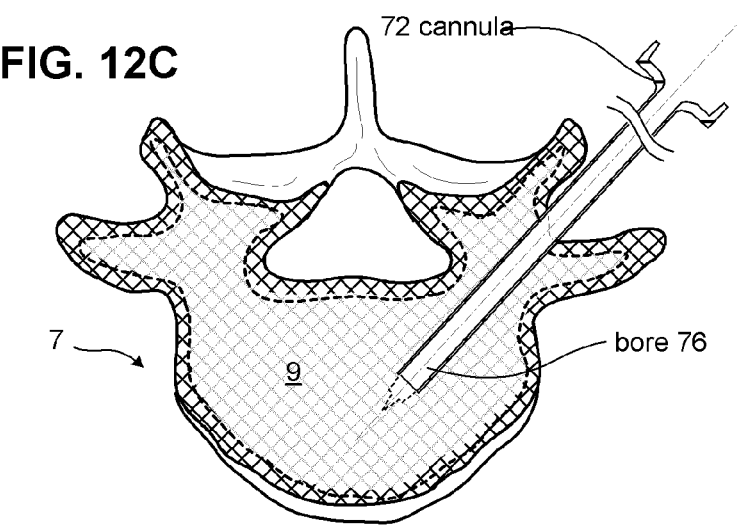

FIG. 12C shows the vertebra of FIG. 12B with the trocar 74 withdrawn leaving the cannula 72 inserted and largely filling the bore cut in the cancellous bone of the vertebral body.

Although not shown in FIGS. 12A through 12I, various alternative tools and devices may be inserted through the cannula to the cancellous bone in the internal volume of the vertebral body. For example, such tools and devices may include tools known in the art for cutting or boring and the like so as to create or shape voids, which voids may subsequently be filled with polymer as using methods described herein and having aspects of the invention.

In an alternative method embodiment (see examples of FIGS. 14-15), such tools and devices may include a solid or elastic prosthesis which may be inserted or positioned into the vertebral body. The prosthesis is preferably subsequently fixed or encapsulated with polymer as using the methods having aspects of the invention. In one example, an elastic prosthesis is inserted into the central volume of the vertebral body, subsequently encapsulated with polymer using the methods and materials described herein and having aspects of the invention. The encapsulated prosthesis may function as a shock absorber, so as to alter the mechanical resiliency of the treated, healed vertebra, and thus reduce impact loads to the spine during activity by the patient.

In a further alternative method embodiment, such tools and devices may include devices for kyphoplasty or vertebral height restoration, such as an extensible balloon or other vertebral re-expansion device. Following a re-expansion procedure, the kyphoplasty device may then be removed and the voids filled with polymer using the methods and materials described herein and having aspects of the invention. Alternatively, the kyphoplasty device may be left in place and encapsulated with polymer using the methods and materials described herein and having aspects of the invention.

Figure 12D:
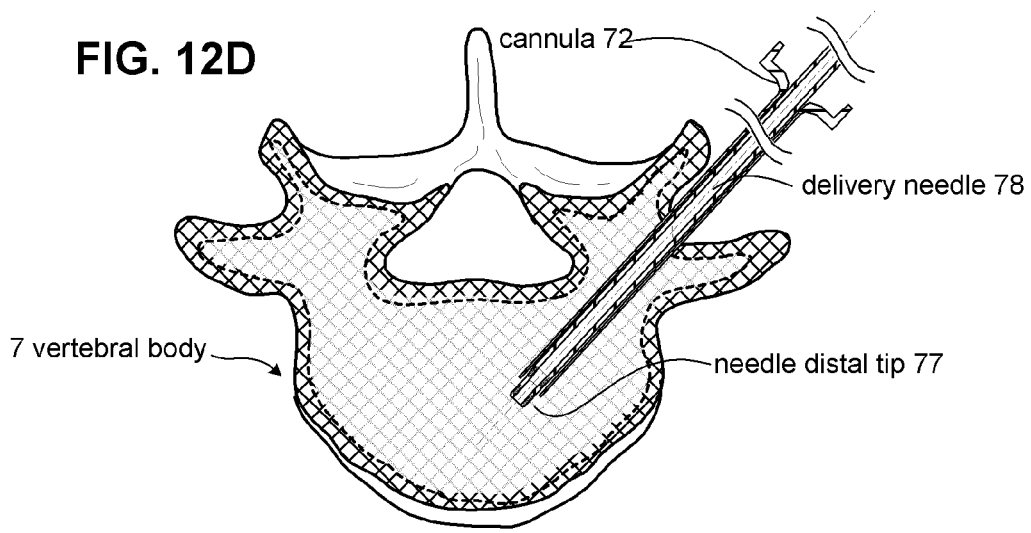

FIG. 12D shows the vertebra of FIG. 12C with a polymer delivery needle 78 such as is described herein (see FIGS. 3B, 4 and 11) inserted into the bore cut in the cancellous bone, and having the needle distal tip 77 positioned adjacent the distal end of the cannula or protruding somewhat.

Figure 12E:
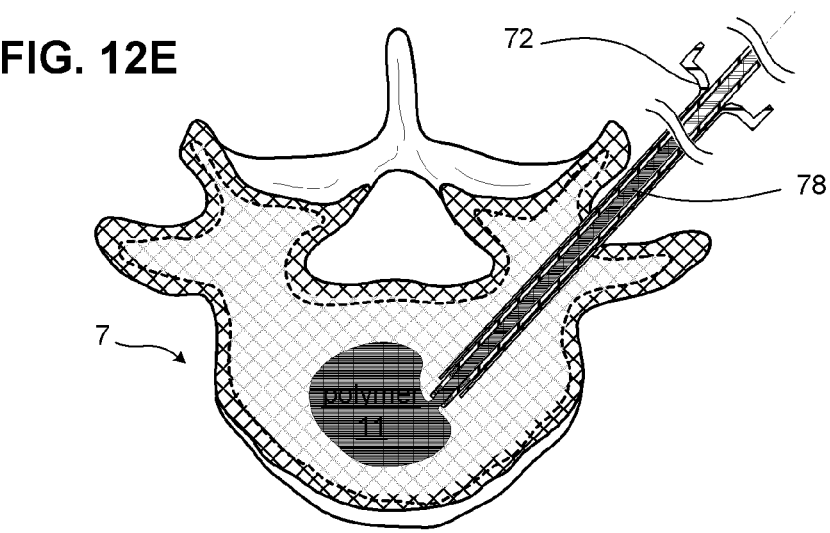

FIG. 12E shows the vertebra and polymer delivery needle of FIG. 12D, and further shows a bolus or portion of polymer material 11 extruded or injected into central volume of the vertebral body. In operation, the delivery needle may be engaged with a polymer delivery system (not shown) such as is shown and described with respect to FIG. 10.

Figure 12F:
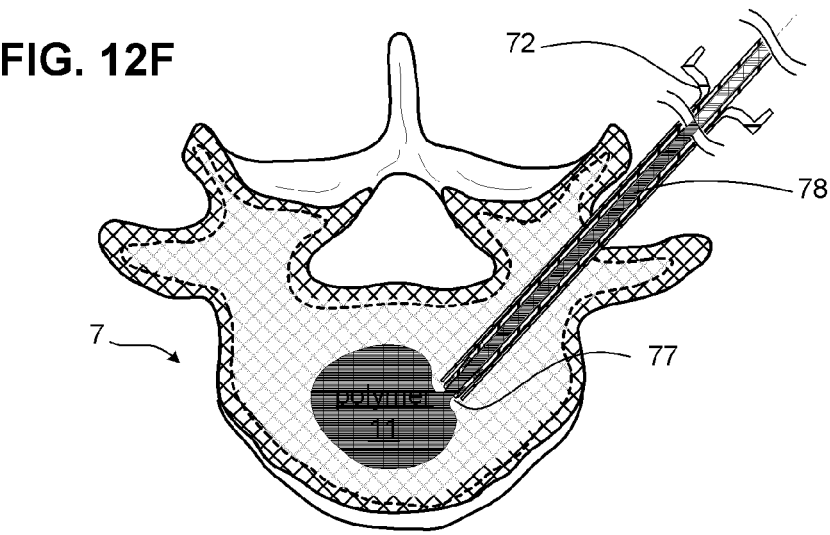

FIG. 12F shows the vertebra and polymer delivery needle of FIG. 12E, in which the needle distal tip has been withdrawn so as to be co-terminus with the cannula, permitting extruded polymer to backfill an addition volume. Note that the cannula also may be withdrawn a selected distance to expose further volume to polymer extrusion.

Both the cases of FIGS. 12D and 12E may represent a step of kyphoplasty, using a viscous bolus of polymer 11 extruded under substantial pressure to re-expand and stabilize the vertebral body as described above with respect to FIGS. 4A-B, so as restore at least some of the height lost in vertebral compression fractures.

Figure 12G:
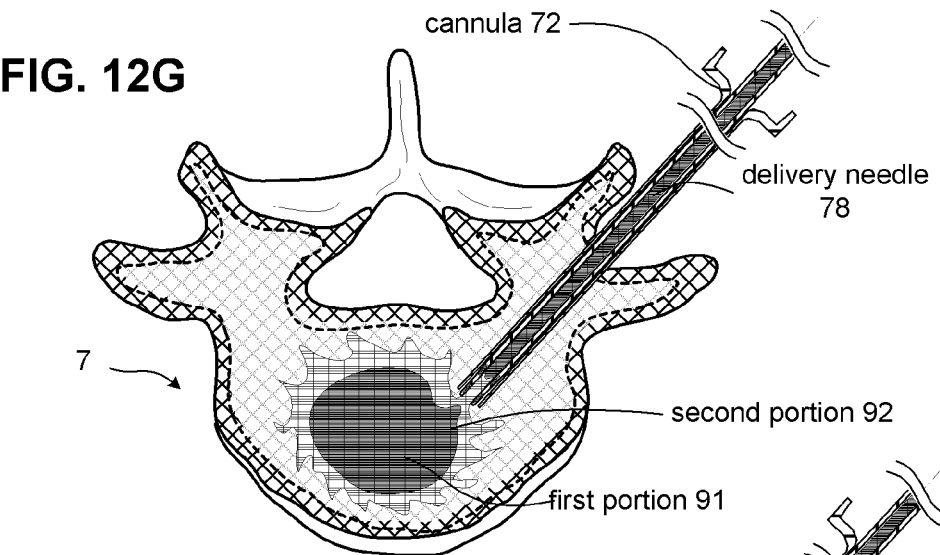

FIG. 12G shows the vertebra and polymer delivery needle of FIG. 12F, in which the delivery needle has been subsequently used to extrude a second extruded polymer portion 92 under different conditions or having a different composition than the first bolus or extruded portion 91 shown as polymer 11 in FIG. 12F. For example, the first portion 91 may be extruded at a lower temperature and higher viscosity; and the second portion 92 may be extruded at a higher temperature (e.g., via heater/feed controls) and consequent lower viscosity, e.g., so as to penetrate smaller voids or fracture cracks in the cancellous bone. In an alternative example, the first and second portions may correspond to different lead and trailing polymer compositions, such as shown in FIG. 13A.

Figure 12H:
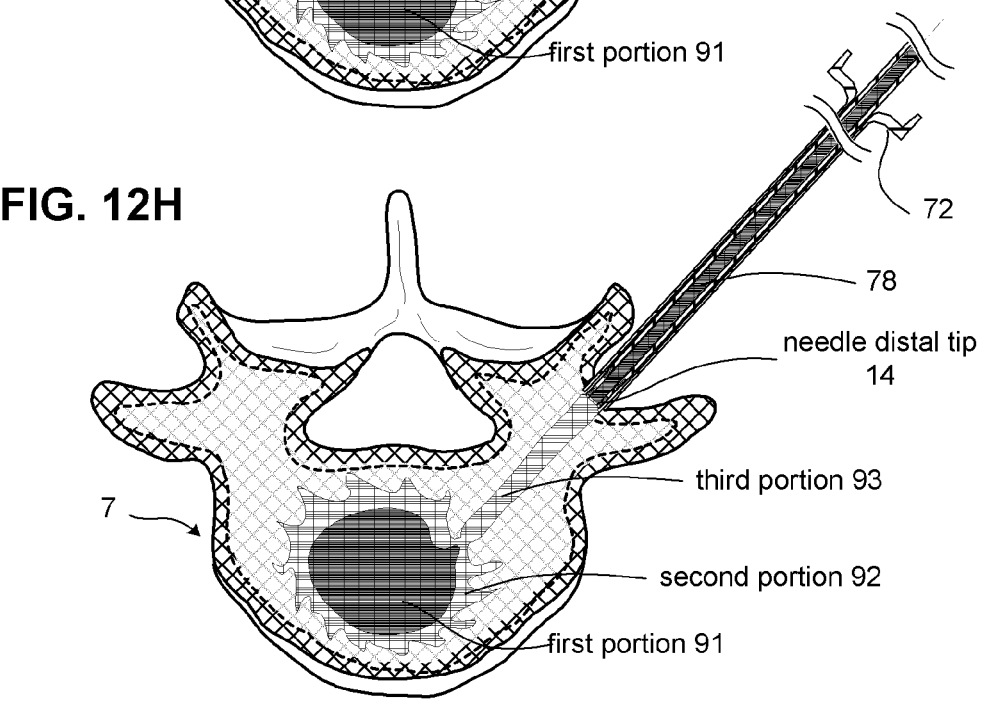

FIG. 12H shows the vertebra of FIG. 12G, in which the delivery needle and cannula have been withdrawn from the internal volume of the vertebral body. In an optional step, the bore formed by the cannula has been filled with a third portion 93 of extruded polymer.

Figure 12I:
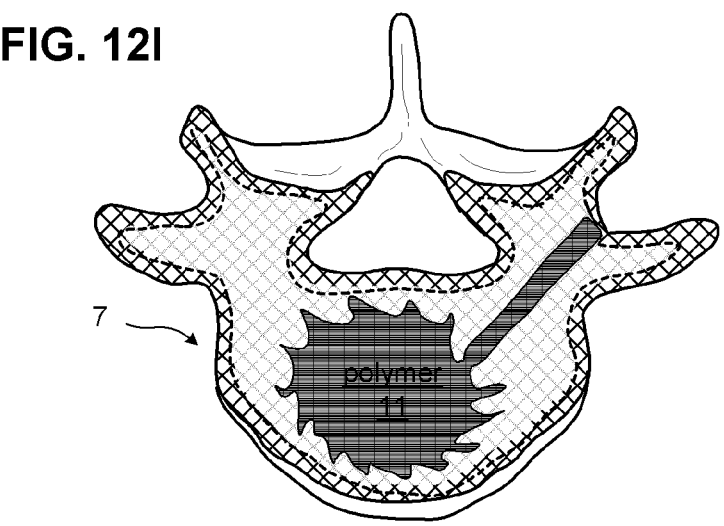

FIG. 12I shows the vertebra of FIG. 12H, in which the delivery needle and cannula have been removed. The case shown depicts the three portion extrusion of FIG. 12H in which each subsequent portion of polymer has the same composition (although perhaps differing in extrusion temperature), and each portion has cooled to body temperature so as to have the same or nearly the same final properties. Note that thermal-chronological history can affect polymer properties independently of composition, such as where re-crystallization is incomplete upon rapid quenching of a polymer melt.

Figure 13A:
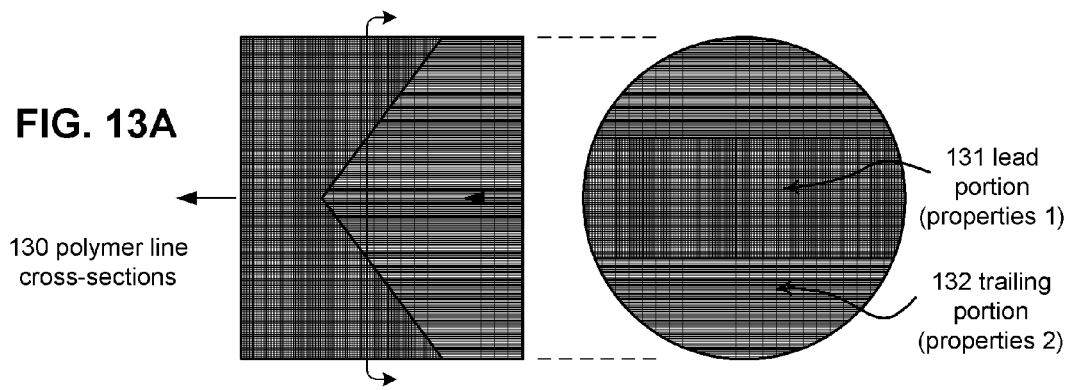
FIGS. 13A to 13C show examples of bulk polymer supply line configurations which provide non-homogeneous compositions.
Figure 13B:
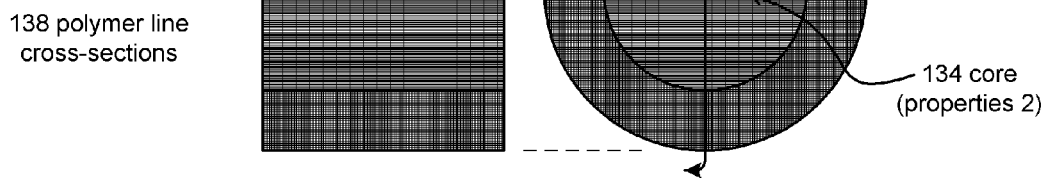
Figure 13C:
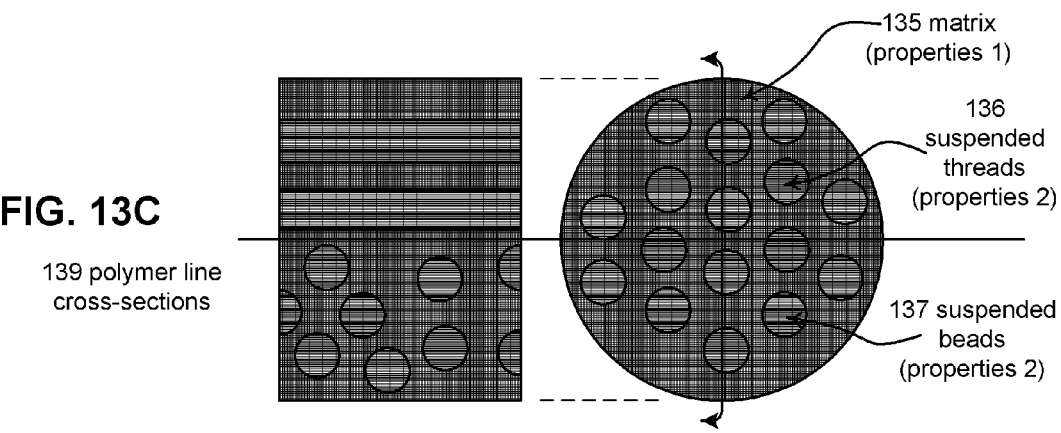

FIGS. 13A to 13C show a cross sections of three examples of bulk polymer supply line configurations providing non-homogeneous compositions.

In FIG. 13A, the polymer line 130 comprises distinct leading and trailing portions 131, 132 having different compositions. These are shown having a sharp boundary, but in the alternative may have a mixing gradient, or multiple linear portions.

In FIG. 13B, the polymer line 138 comprises distinct shell and core portions 133, 134 having different compositions. These are shown having a sharp boundary, but in the alternative may have a mixing gradient or multiple concentric shells.

In FIG. 13C, the polymer line 139 comprises distinct matrix 135 and filler 136, 137 portions having different compositions. In the upper portion the filler 136 comprises approximately parallel suspended threads having a length substantially exceeding the diameter of the line (the threads may be continuous along the length or discontinuous. In the lower portion the filler 137 comprises randomly suspended beads or short fibers having a length or diameter substantially less than the diameter of the line (the beads may be distributed at uniform density along the length of the polymer line 139, or may have variable density. Combinations of the upper and lower case may be employed.

Figure 14A:
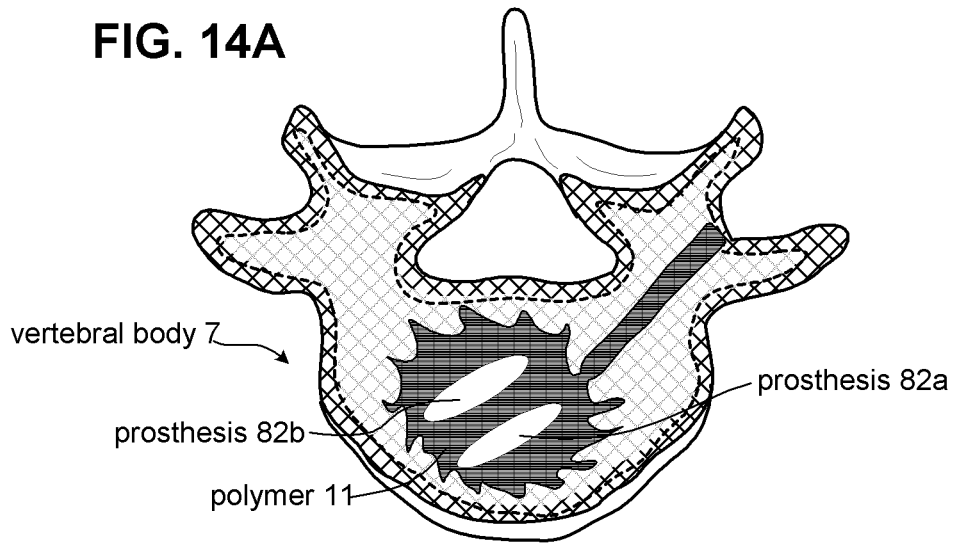
FIGS. 14A and 14B are two views of a treated vertebral body in which one or more prosthesis have been inserted and encapsulated with a polymer as described herein using the methods having aspects of the invention.
Figure 14B:
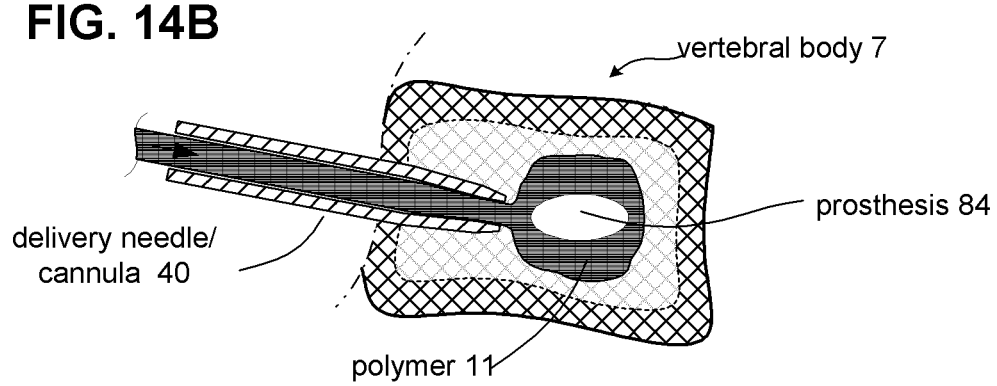

FIGS. 14A and 14B are two views of a treated vertebral body (similar to the views of FIGS. 2B and 12I) in which one or more prosthesis 82*a*, 82*b*, 84 have been inserted and encapsulated with polymer 11 using the methods having aspects of the invention, as described further above.

Figure 15:
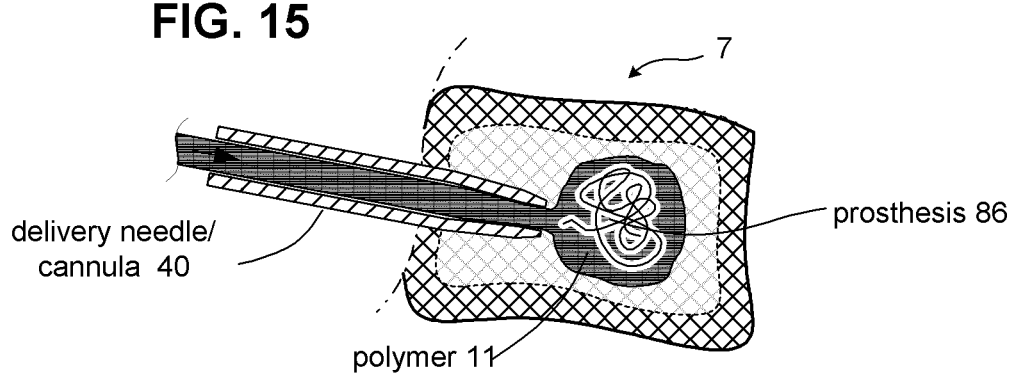
FIG. 15 is substantially similar to FIG. 14B, except that the prosthesis is a thread-like or substantially elongated flexible member inserted so as to be coiled or folded in a void within the vertebral body prior to encapsulation using the methods having aspects of the invention.

FIG. 15 is substantially similar to FIG. 14B, except that the prosthesis 86 is a thread-like or substantially elongated flexible member inserted so as to be coiled or folded in a void within the vertebral body prior to encapsulation using the methods having aspects of the invention.

FIGS. 16A through 16D show schematically an exemplary polymer cement delivery needle assembly having aspects of the invention, shown in both exploded and assembled configuration. FIG. 16A shows an example of a needle inner portion, comprising a proximal lumen entrance extending from a needle base configured for needle mounting to a polymer delivery system (many alternative needle base and mounting configurations are possible). The lumen entrance extends distally as a tubular barrel structure to a tapered section positioned adjacent the distal lumen tip. The lumen may be formed in the manner of conventional surgical and orthopedic needles in similar sizes or gages, for example of stainless steel. In an embodiment, a cylindrical needle blank may be machined internally to provide the tapered configuration, optionally machined also to provide for either or both of a mounting to a base, electrical and/or signal contacts, and/or a recessed portion for one or more longitudinal conduits and instrumentation as shown in FIG. 16B (e.g., heating coils, thermal sensors, and the like).

FIG. 16C shows an example of a needle assembly in which an optional mating outer tubular portion is fitted over the lumen inner portion shown in FIG. 16B. For example, the outer needle portion may provide for greater needle strength when combined with the inner portion, may provide different heat conductivity than the inner portion (e.g., insulating), or the like. Alternatively, coatings may be applied to the needle inner portion to provide such properties, e.g. a resilient polymer coating.

FIG. 16D illustrates the operation of the assembled needle, in which a polymer feed rod in a relatively stiff or rigid state enters the proximal needle entrance and is translated distally with wall clearance until it contacts the tapered portion. Heat application adjacent the needle tip causes the polymer to undergo a thermo-mechanical transition to a flowable (e.g., melted) state. The polymer is delivered to a deployment site (e.g., within a vertebral body) where it undergoes a cooling transition to a functional support state (e.g., having a modulus at body temperature suitable for vertebral reinforcement).

FIGS. 17A-17C illustrate schematically a method of inserting one of the embodiments of a delivery needle having aspects of the invention into an internal body volume, such as to access the cancellous bone core of a vertebral body. An annularly nested set of cannula and trocar is first inserted through a body surface into the internal body volume, such as by thrusting force, cutting blade, and/or revolving drilling or the like. The trocar may then be removed to leave an open bore supported by the cannula. A polymer delivery needle may then be inserted into the cannula lumen so as bring the needle distal dip into or adjacent the internal body volume.

Figure 18:
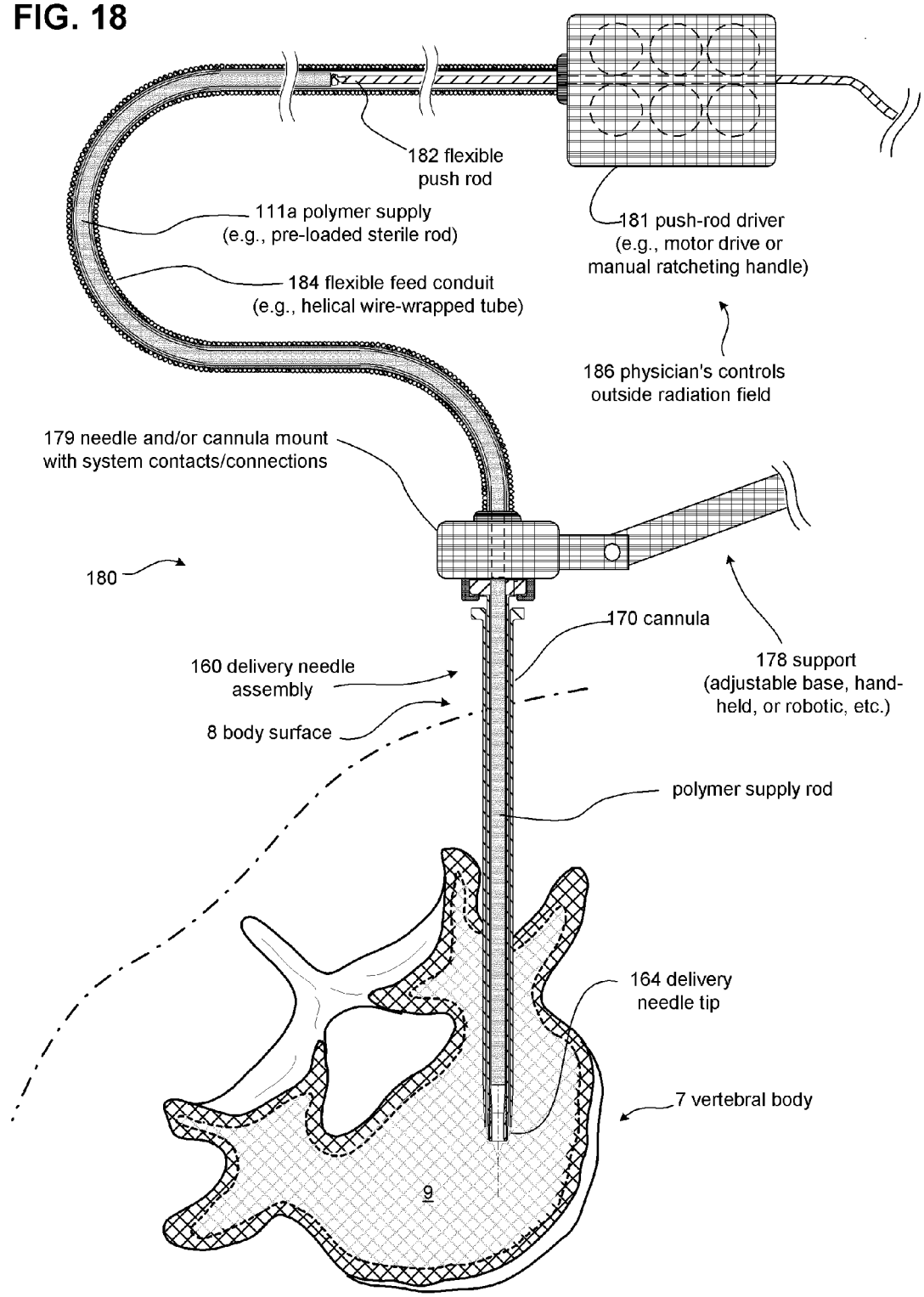
FIG. 18 shows schematically an exemplary polymer delivery system having aspects of the invention comprising a feed conduit housing a polymer rod or filament, driven to a mating delivery needle via a push rod mechanism.

FIG. 18 shows schematically an alternative exemplary polymer delivery system having aspects of the invention differing in respects to the embodiment shown in FIG. 10. In the alternative embodiment, a polymer supply rod is delivered by compressive forces through a conduit. The delivery system comprises a feed conduit housing a polymer rod or filament, the conduit mounted to the delivery needle and to a rod feed mechanism. In the example shown, the conduit is configured to be flexible, such as having a wire-wrapped tube capable of supporting the polymer rod during application of a compressive drive force. In the example shown, a motor-driven push-rod applies a drive force to the polymer rod. Likewise, a manual drive mechanism, such as a ratcheting handle, may be provided. In the example shown, a support mechanism guides the delivery needle to a surgical body opening, such as an adjustable support base, a handheld support handle, a robotic support, or the like. Conveniently, the conduit and polymer supply rod may be provided in a pre-loaded, sterile package ready for mounting to the needle and delivery system.

Figure 19A:
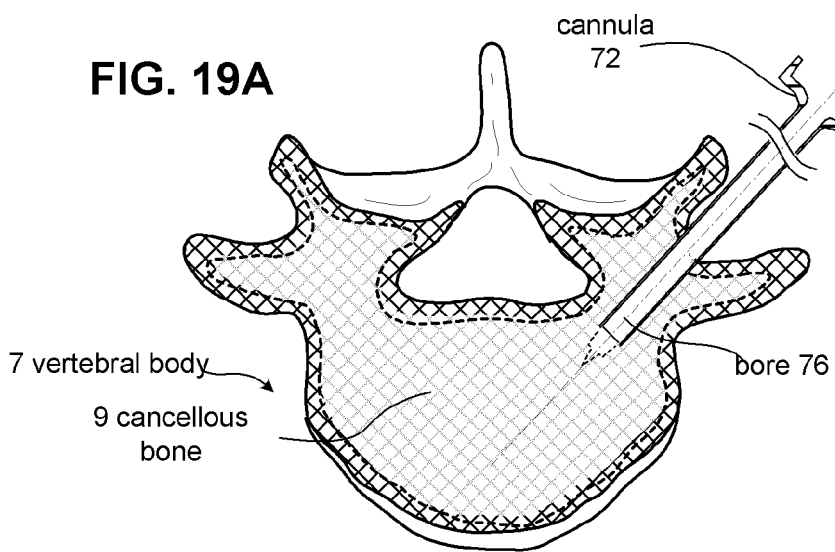
FIGS. 19A through 19F show schematically an exemplary method of performing a kyphoplasty procedure employing a delivery needle assembly and polymer bone cement having aspects of the invention.
Figure 19B:
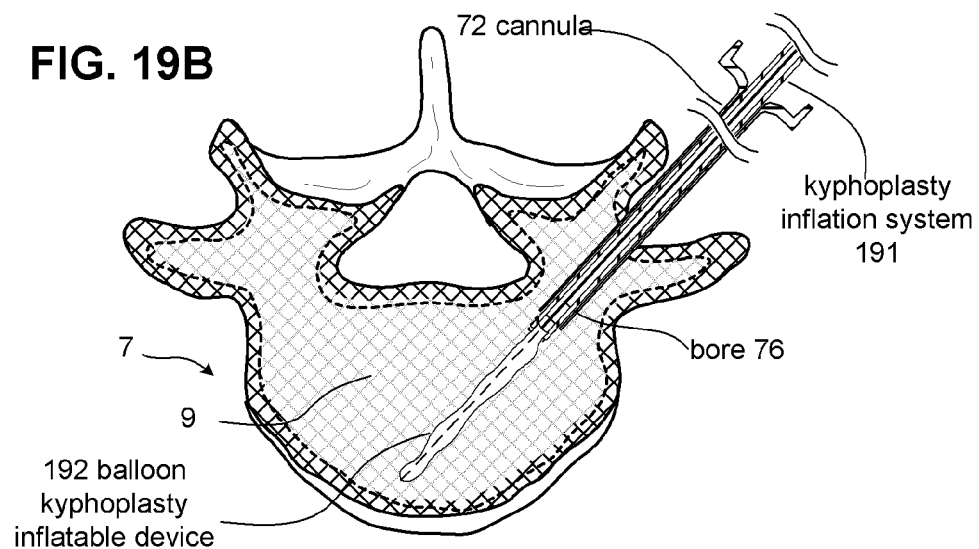
Figure 19C:
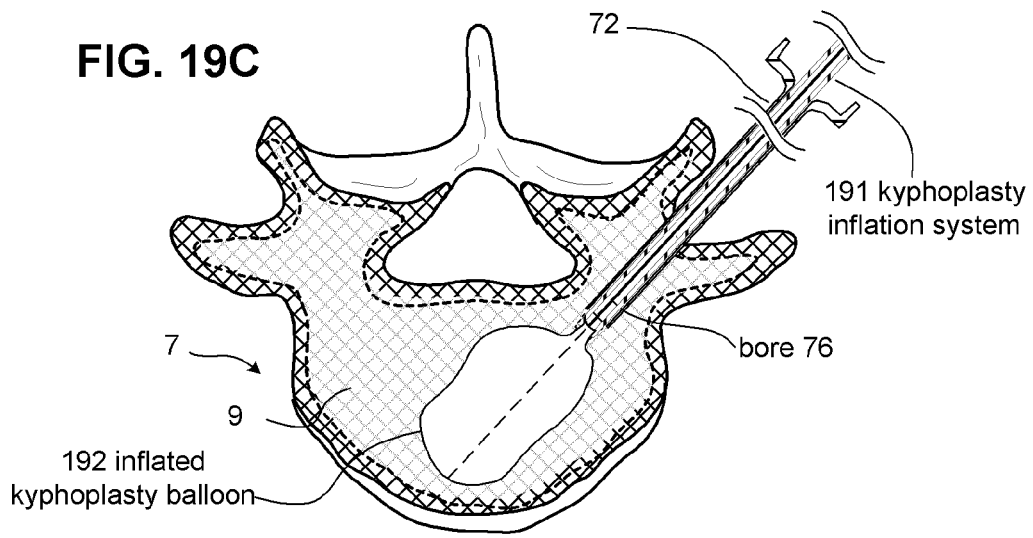
Figure 19D:
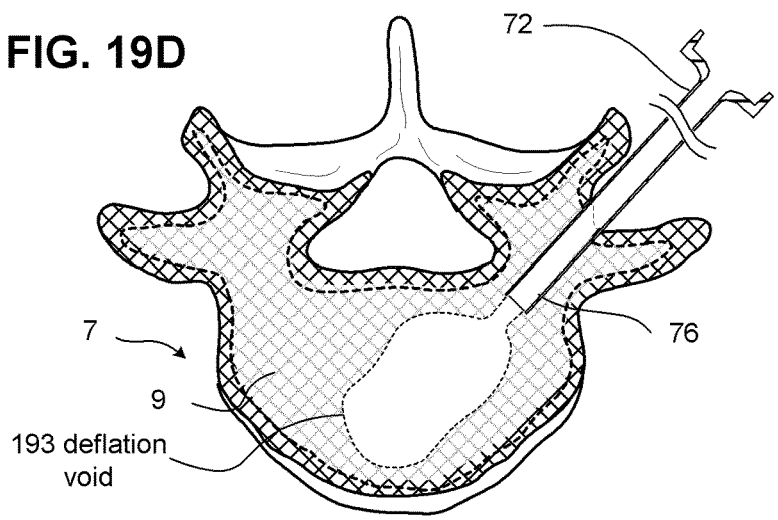
Figure 19E:
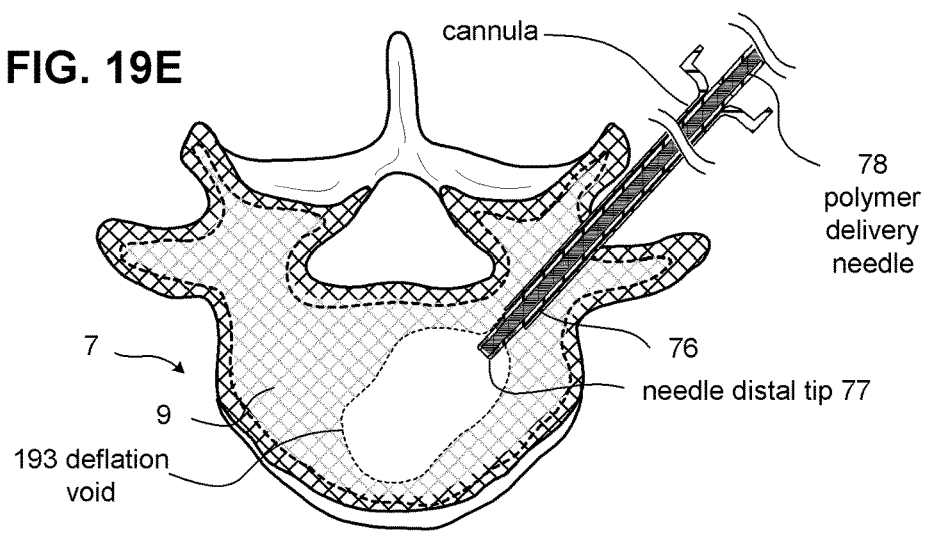
Figure 19F:
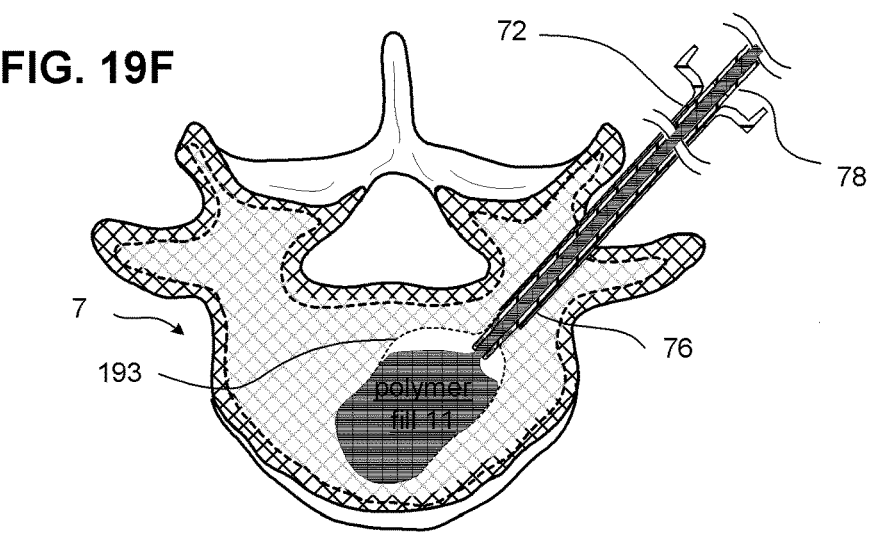

FIGS. 19A through 19F show schematically an exemplary method of performing a kyphoplasty procedure employing a delivery needle assembly and polymer bone cement having aspects of the invention. The method may be generally similar to the method illustrated in FIGS. 12A-12F. However, as shown in FIGS. 19B-19D, an inflatable balloon kyphoplasty device 191 may be inserted and inflated to create a void within the vertebral body and/or to recover effective height of the vertebral body by exerting expansion forces. For example, an orthopedic balloon 192 such as is marketed by Kyphon, Inc. of Sunnyvale, Calif. may be used. In some procedures, more than one balloon may be employed, such as bilaterally within the vertebral body. As shown in FIGS. 19B-19D, the resulting void or voids may be filled by application of a polymer delivery needle and polymer fill 11 having aspects of the invention. The steps indicated in FIGS. 19A-19F are exemplary and may be performed in any useful operational order or in combination with other steps.

FIGS. 20 through 22A-B show several alternative exemplary embodiments of a polymer delivery needle assembly having aspects of the invention. Within the figures are examples of polymer heat profiles illustrating the physical state transition of the composition as it moves through the delivery needle to an internal body volume (these profiles are illustrative of principles of operation only).

Figure 20:
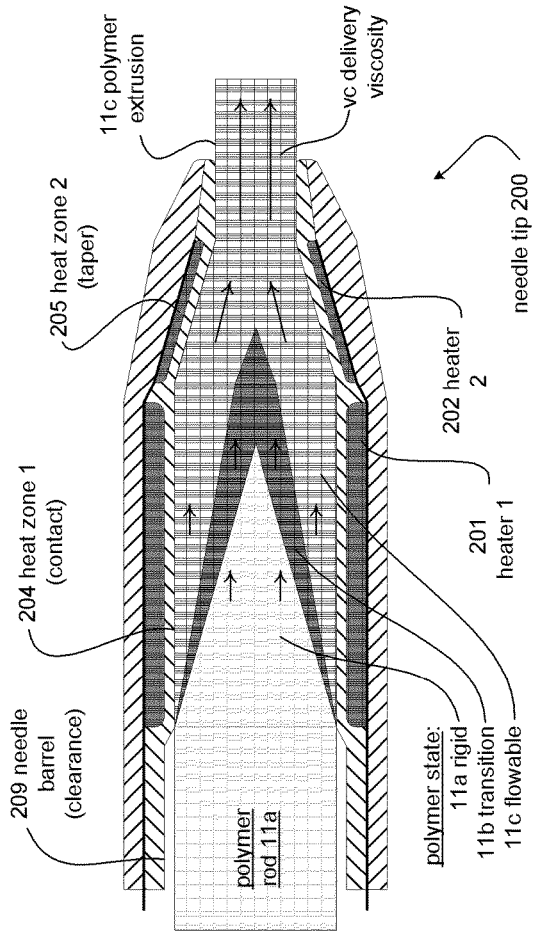

FIG. 20 shows schematically an embodiment of a polymer delivery needle distal tip portion having a relatively short heated zone. In this example, two heated zones are provided with independently controllable heaters. The substantially rigid polymer feed rod (sufficiently stiff to bear compressive drive forces) is feed distally through the lumen with wall clearance to allow sliding through the unheated portion of the lumen. As the rod reaches a first medial heater zone with a narrowed diameter, contact is made with the heated lumen surface. Within the first heat zone a substantial radial portion of the polymer rod passes through a transition state to a flowable state. As the polymer reaches a second more distal heat zone (optionally unheated) the lumen may taper and additional heating brings the rod to a selected delivery viscosity, at which state the polymer is extruded from the distal needle tip. The taper of the lumen may be selected to provide a desired relation of polymer feed rate, pressure, local velocity and tip exit diameter.

Figure 21:
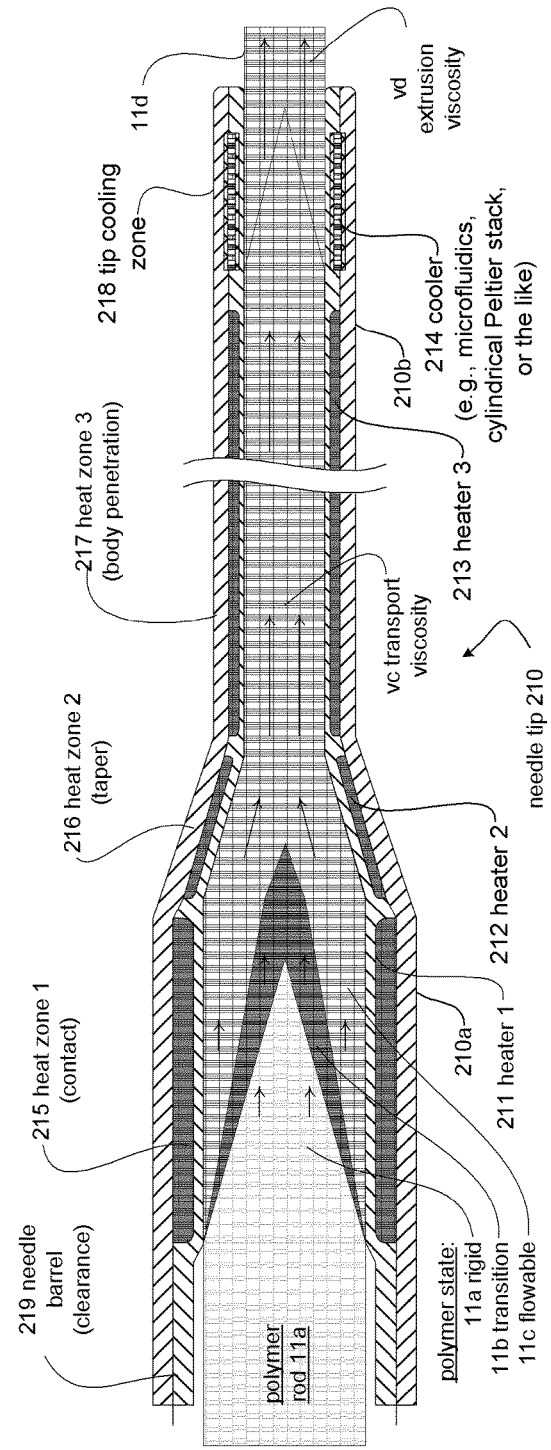

FIG. 21 shows schematically an embodiment of a polymer delivery needle distal tip portion having an elongate distal tip extension for body penetration, having an additional heated zone and an optional cooled tip. The proximal and medial portions of the delivery needle may be generally similar to that shown in FIG. 20. The distal tip portion is elongated and has a generally smaller diameter to facilitate penetration through a reduced incision diameter (e.g., a smaller cannula). A third distal heat zone may be provided, configured to maintain a selected lumen transport viscosity through the elongate distal tip. An optional tip cooling zone (comprising e.g., microfluidics, cylindrical Peltier stack, or the like) may be provided to cool the polymer to an extrusion temperature and viscosity (lower temperature and higher viscosity than the transport state). The lumen diameter, lumen transport temperature, feed rate and polymer properties may be selected to provide a selected pressure drop across the elongate distal tip extension.

FIGS. 22A and 22B show schematically two alternative embodiments of a polymer delivery needle distal tip portion with an elongate distal tip extension for body penetration, each generally similar to that shown in FIG. 21, having particular features. In the embodiment of FIG. 22A, the initial heat zone is subdivided into a relatively high heat rate portion (1a) to provide for rapid softening of the polymer rod with reduced surface viscosity. Additional untapered (1b) and tapered (2) heat zones have heat rates selected to provide for transition and a flowable state through substantial the radial extent of the polymer bolus as it reaches the extended distal tip portion. One or a plurality of separately controlled heaters provide a viscosity management distal heat zone in which the heat rate is balanced against conductive loses to tissue to maintain a selected viscosity range. Thermal sensors may be included configured for sensing of one or both of local polymer temperature and adjacent tissue temperature, permitting feedback control of heaters on a real-time basis during treatment. In the embodiment of FIG. 22B, a portion of the extended tip is provided with a shell having insulating or relatively low-thermal-conductivity properties, while a most distal portion of the extended tip is comprises a high conductivity material, inducing more rapid heat transfer to adjacent tissue close to the extrusion exit.

Figure 23:
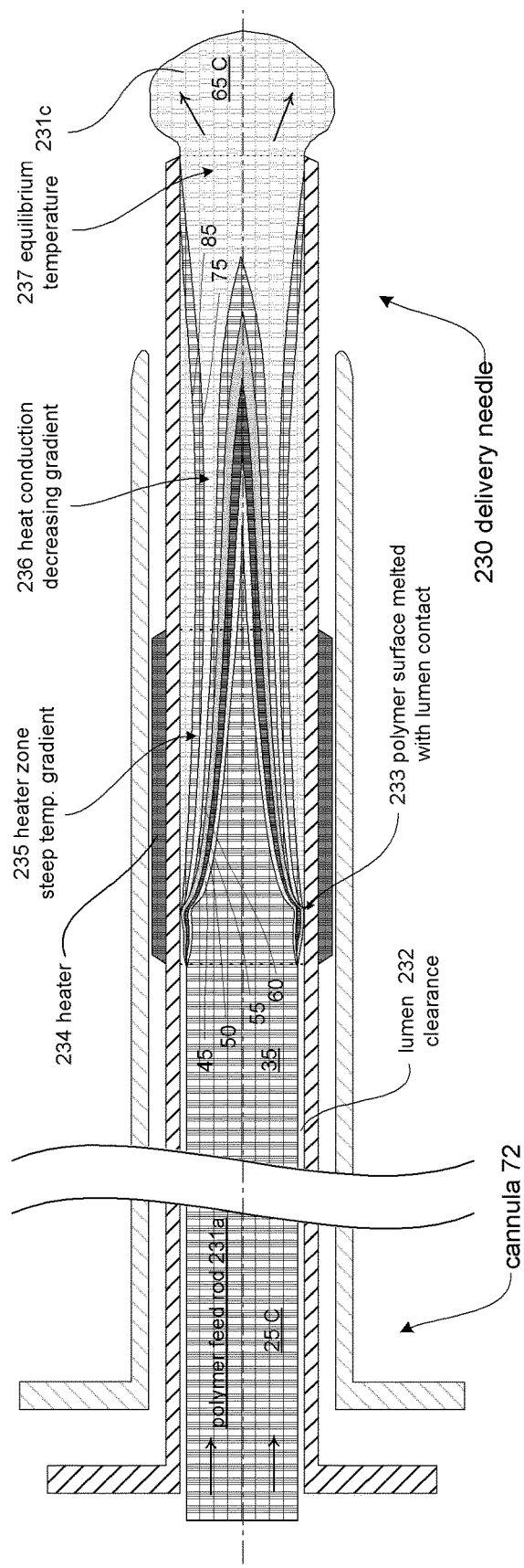
FIG. 23 shows schematically an embodiment of a polymer delivery needle having aspects of the invention having a substantially un-tapered lumen, shown as mounted in an insertion cannula within a patient's body, illustrating a schematic polymer heat and transition profile.

Although a number of the delivery needle embodiments having aspects of the invention include portions of reduced diameter or taper to control polymer rod engagement with the heated lumen inner surface, delivery needle embodiment having aspects of the invention need not have such features. FIG. 23 shows schematically an embodiment of a polymer delivery needle having a substantially un-tapered lumen throughout, shown as mounted in an insertion cannula within a patient's body. It has been demonstrated that in proximity to a heated lumen surface, indicated as heater zone, the selection of heat rate and polymer composition permit rapid surface melting, so as to can provide efficient contact of the polymer with the heated inner needle surface. As the sliding polymer rod enters the heater zone, the melted surface of the polymer rod "wets" the lumen surface and generate viscous resistance forces to effectively stick the polymer bolus to the lumen surface and provide efficient heat transfer. The viscous forces also provide consistent flow resistance. In the example shown the heater zone induces a steep radial temperature gradient as the rod is rapidly heated by conduction. An unheated zone of lumen of selected length may be provided (indicated as "decreasing temperature gradient") to permit equilibration of the polymer heat profile to approach a selected equilibrium temperature as the polymer is extrude into a body volume. The polymer isotherms shown are intended to illustrate the relative gradients, and both heater energy rate and polymer feed rate may be selected to achieve a desired extrusion temperature.

Figure 32A:
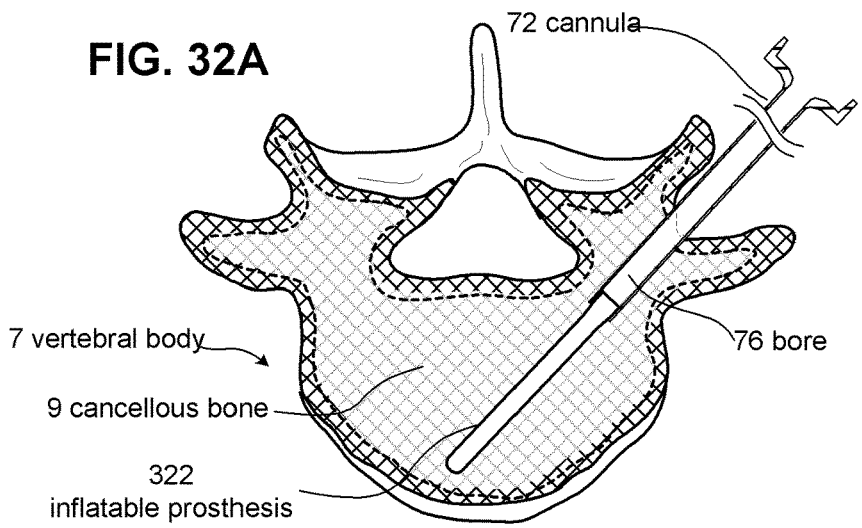
FIGS. 32A through 32C show schematically an exemplary method of performing a vertebroplasty procedure employing an inflatable prosthesis inserted into a vertebral body, and being inflated using a polymer delivery needle assembly and polymer composition having aspects of the invention.
Figure 32B:
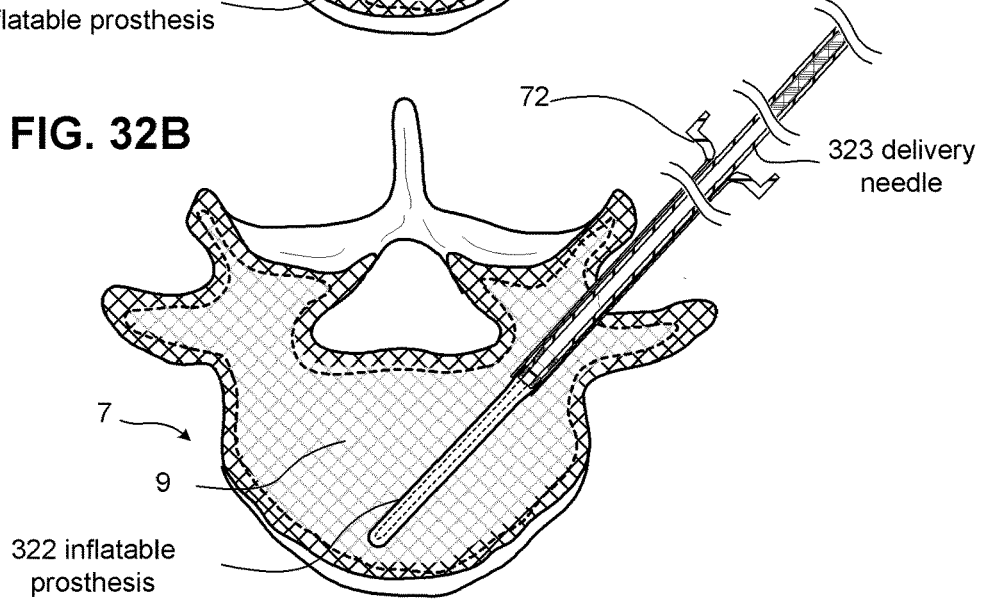
Figure 32C:
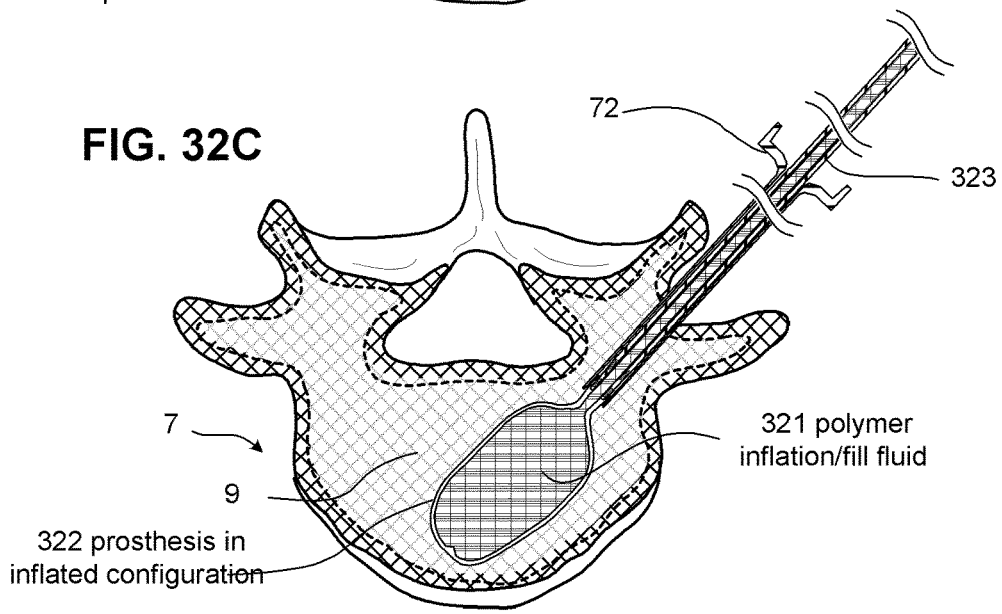

FIGS. 32A through 32C show schematically an exemplary method of performing a vertebroplasty procedure employing a inflatable prosthesis having aspects of the invention, inserted into a vertebral body, and inflated using a polymer delivery needle assembly and polymer composition having aspects of the invention. In FIG. 32A an uninflated prosthesis 322 is shown as inserted though a cannula into the vertebral body, in much the same manner as the kyphoplasty device is shown inserted in FIG. 19B. If needed, a trocar may be used to advance the uninflated prosthesis 322 to a selected position. The uninflated prosthesis 322 may comprise radio-opaque materials to assist in placement (e.g., a tip marker).

FIG. 32B shows a polymer delivery needle 321 having aspects of the invention inserted through the cannula to mate and communicate with the uninflated prosthesis 322. FIG. 32C shows the prosthesis having been inflated by injection of a polymer composition embodiment, heated to a fluid state, and fed with sufficient pressure to inflate the prosthesis.

Due to the small diameter and small cross-section area of the solid state polymer feed rod, very substantial delivery injection pressure in the heated zone of the delivery needle can be developed with only moderate rod feed forces (mechanically driven or manually driven), as described above (see discussion of FIG. 18). Indeed, sufficient pressure can be developed to restore all or a portion of vertebral height lost due to a compression fracture, via expansion forces generated by the polymer fluid injection pressure. Following inflation and filling of the prosthesis with polymer composition in the fluid state, the filled prosthesis may be permitted to cool until the polymer has solidified. The cannula and delivery can be removed, as described above with respect to other treatment methods, with the supported inflated prosthesis remaining in place.

Thermoplastic Polymer Composition Examples

FIGS. 24A through 24C schematically illustrate an example of a polymerization reaction for making one of a range of side chain crystallizable polymer compositions having aspects of the invention. In the particular examples described below, the composition may comprise a polymer that includes monomers selected from alkyl methacrylates, such as methyl methacrylate (MMA), which are copolymerized with and side-chain alkyl methacrylate having a crystallizable side chain, such as behenyl methacrylate (BHMA), having a side chain length of C22. Other side chain monomers may be copolymerized in substitution or in combination, such as hexyl methacrylate (HMA) and other alkyl methacrylates of selected chain size (e.g., the co-polymerization of 2, 3 or more selected monomers). One of ordinary skill in the art will appreciate that alternative or additional monomers and polymerization schemes may be included without departing from the spirit of the invention, such as described in the more general description above under the heading "Side-Chain Crystallizable Polymers".

FIGS. 24A-C illustrates an example of copolymerization of monomers BHMA and MMA in selected proportions y:x w/w %. The following is a specific example corresponding to FIGS. 24A-C for the making of 70/30 w/w % proportion BHMA/MMA copolymer: Preparation: Into a 1 L reaction vessel that was immersed in a 65° C. oil bath 102.90 g of behenyl methacrylate, 44.10 g of methyl methacrylate, and 695 mL of toluene were mixed at 300 RPM for 5 minutes and allowed to dissolve while being purged with nitrogen at 5 ml/min. After solvation of the monomers 0.710 g of AIBN (azobisisobutyronitrile) was added into the reaction vessel using 5 mL of toluene to quantitatively transfer all initiator. Purge was continued for another 20 minutes, then N$_2$ flow rate was reduced to approximately 0.2 ml/min to blanket reaction. Reaction was left overnight to react for 18 hours. 1.20 g of MeHQ (hydroquinone mono methyl ether) was then added to halt reaction and a Dean-Stark trap was placed in line. The oil bath was turned up to 90° C. and 360 mL of toluene was distilled off and discarded. The remaining reaction liquid was allowed to cool for 30 minutes.

Isolation:

After cooling, 40 mL of the reaction liquid was precipitated with 0.5 L of 100% isopropyl alcohol and the product was then vacuum funneled. This process is repeated until all reaction liquid has been precipitated and set to dry.

Figure 25:
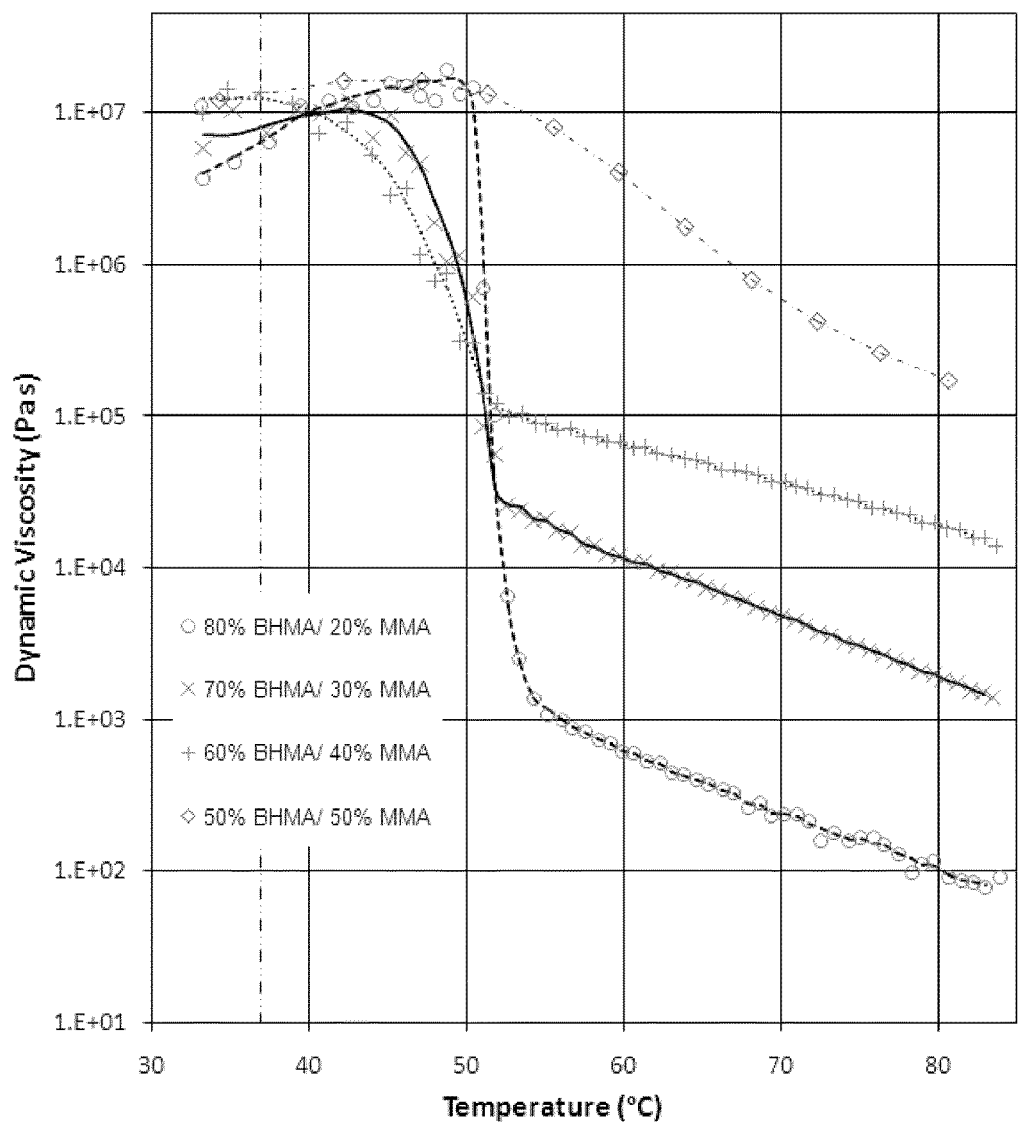
FIG. 25 is a plot illustrating the effect of monomer proportions on the rheological properties of the copolymer compositions having aspects of the invention.

FIG. 25 is a plot illustrating the effect of monomer proportions on the rheological properties of the copolymer compositions having aspects of the invention. The example copolymers are each made as generally described above for the 70/30 w/w % BHMA/MMA copolymer with appropriate adjustments of quantities. The example copolymers plotted in FIG. 25 have a weight proportion of BHMA varying between 50% and 80% (balance proportion being MMA) each example being tested by the same methodology to determine the relation between dynamic viscosity (Pa·s) and temperature (° C.). The data is presented on a log scale of dynamic viscosity, the data points as indicated in the plot legend (the points are overlain by a smoothed trend line for clarity of presentation). It may be seen that as the proportion of BHMA is increased (and the mean distance between side chains decreases), the transition gradient becomes increasingly steeper, and the melt viscosity at a given temperature decreases.

Thus for proportions of BHMA from 60 to 80% w/w %, the melting temperature is between 50-55° C., and the viscosity decreases generally exponentially (appearing linear on the log plot) above the melting temperature. For example, the rheological plot shown in FIG. 25 for the 70/30 w/w % BHMA/MMA copolymer reveals a 3-decade drop in viscosity at the melt transition with a subsequent exponential viscosity decrease above 55° C. that may be represented by the exponential formula $V_{dyn}=3*10^6*e^{-0.09T}$, with $R^2=0.998$. It may also be seen that each copolymer example has a dynamic viscosity of about $10^7$ Pa·s at a normal human body temperature of 37° C. (vertical phantom line). Thus, it may be seen that for the exemplary copolymer compositions, the rheological characteristics may be tailored in a particularly medically useful range from about 37° C. to about 100° C.

FIG. 26 is a plot illustrating the rapid solidification characteristic of the polymer compositions of these examples. The plot shows dynamic viscosity vs. time for a procedure in which an example 70/30 w/w % BHMA/MMA copolymer was quenched from 90° C. to 37° C. in 3 minutes, then annealed at 37° C. for 1 hour. In this example, there is no added crystallization initiator (which optionally may be added). It may be seen that there is no substantial delay in polymer side chain crystallization at human body temperature, indicating that a polymer augmentation or support material applied as described herein would likely reach its functional state quickly.

FIG. 27 is a plot illustrating the ductility that can be achieved in the polymer compositions of these examples. The plot shows the relation between elongation strain and applied stress of a 10 mm long sample. It may be seen that the elongation is well over 100%.

FIG. 28 is a plot illustrating the effect of a radio-opacity additive on the rheological properties of polymer compositions having aspects of the invention. The plot shows a comparison of the 70/30 w/w % BHMA/MMA copolymer as shown in FIG. 25 (same data) with comparable test data of a mixture of 80% of this copolymer with 20% w/w of $BaSO_4$, sufficient in quantity to provide substantial radiopacity of the composition in medical uses. It may be seen neither the viscosity at 37° C. nor the melting transition point are significantly affected. The viscosity above 55° C. is offset slightly upwards, but is of the same general order of magnitude.

FIGS. 29A-B, 30A-B and 31A-B illustrate the manner in with exemplary polymer compositions having aspects of the invention may be selected to have a desired set of functional properties suited to a particular medical application.

Figure 29A:
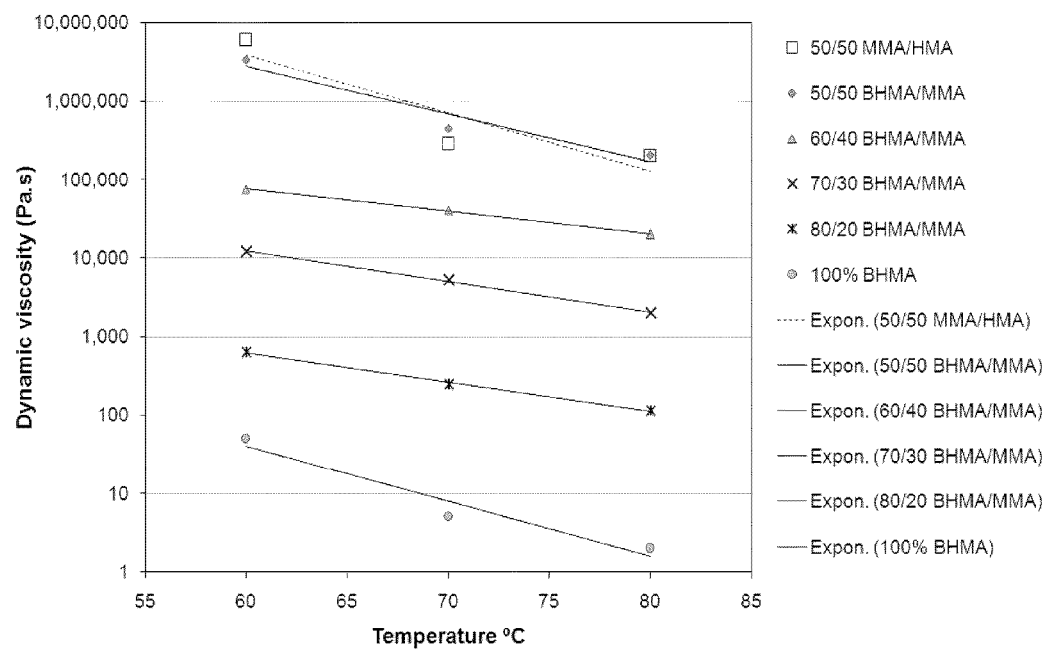

FIG. 29A and FIG. 29B show the viscosity-to-temperature relationship of a series of example copolymer compositions at 60° C., 70° C., and 80° C. The series include the 60 to 80% w/w % range BHMA/MMA copolymers that are plotted in FIG. 25, as well as a 50/50 w/w % copolymer of MMA and hexyl methacrylate (HMA), and a 100% homopolymer of BHMA. FIG. 29B shows both the plotted data of FIG. 29A, and also shows superimposed curve fits (Microsoft Excel exponential trend lines fit to 3 data points). It can be seen that the compositions provide a consistently varying "ladder" of choices of viscosity at approximately order of magnitude intervals in this particularly useful temperature range. Specifically the 60 to 80% w/w % range of BHMA/MMA copolymers provide highly consistent viscosity characteristics spanning 2 orders of magnitude. For these compositions, the close curve fits indicate that the variation within the 60-80° C. temperature range is essentially exponential.

Figure 30A:
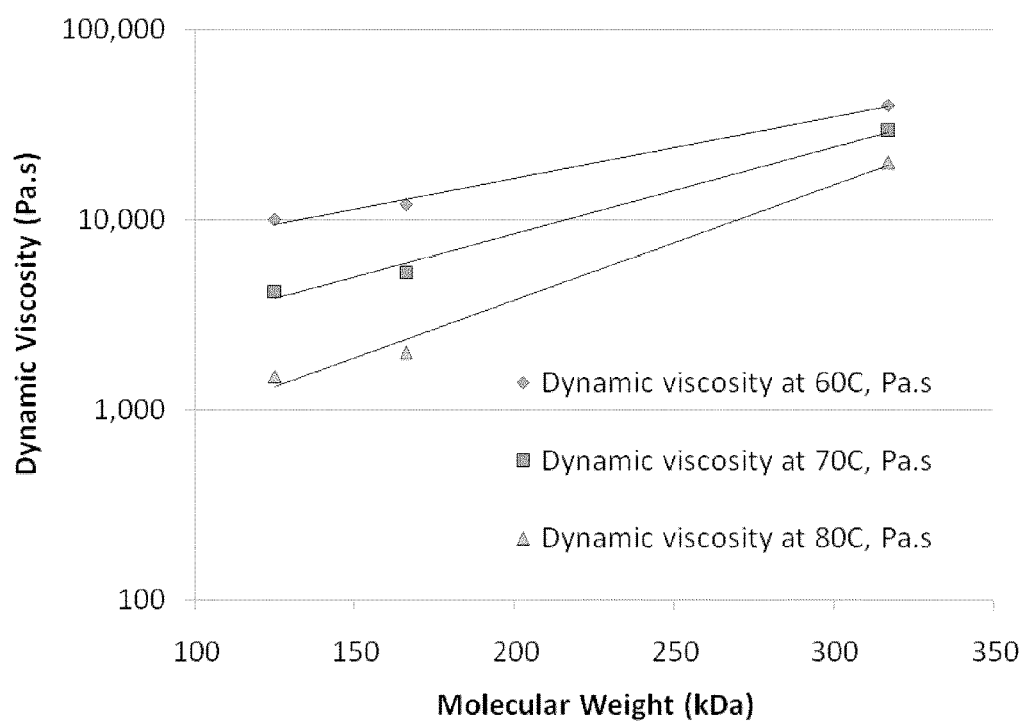

FIG. 30A and FIG. 30B show the effect of molecular weight on viscosity over the temperature range of 60-80° C., for polymer compositions having aspects of the invention, using for an illustrative example a 70/30 w/w % BHMA/MMA copolymer.

Mean copolymer chain length or molecular weight can be controlled by a number of techniques known in the art. For example, molecular weight can be affected by the purity of the monomers employed, by the presence of species (e.g., chain transfer agents) which can terminate a polymerization chain, and the like. It can be seen that, for each temperature, the viscosity increases consistently as molecular weight increases (for clarity of data presentation, second-order polynomial trend lines are plotted). The decrease in melt viscosity with increasing temperature is more dramatic at the lower range of molecular weight. Thus, a composition with greater, or lesser, viscosity dependence upon temperature may be purposely designed via judicial molecular weight selection. These consistent rheological properties of polymer compositions having aspects of the invention, illustrated in FIGS. 29A-B and 30A-B, allow a composition to be selected to have a desired viscosity at a selected temperature.

FIG. 31A shows the effect of polymer composition on compressive strength in the solid state (e.g., at temperatures below the relevant transition point, e.g., Tg or Tm), for polymer compositions having aspects of the invention, as contrasted with the strength of commercial bone cements and anatomic vertebra. The compressive strength of the various copolymer examples are of the same order of magnitude, ranging from about 9 MPa to about 19 MPa. By contrast the current commercial bone cements are generally of an order of magnitude higher. The high modulus and strength of current commercial bone cements is poorly matched with the much lower modulus of both health and osteoporotic vertebral bone, resulting in stress concentrations in augmented or repaired vertebral bodies. Such mismatching of materials may contribute to subsequent bone damage or fracture. The more appropriate match of modulus and strength of polymer compositions having aspects of the invention can provide a more effective bone repair and improved prognosis.

FIG. 31B compares two of the compositions in FIG. 31A (marked with asterisks *) with respect to the effect of substitution of a different monomer (HMA) for a portion of the MMA in two copolymer compositions which both comprise 70 w/w % BHMA. The compositions thus would be expected to have essentially the same average distance between BHMA $C_{22}$ side chains. The effect of substitution of one-half by weight of $C_6$ hexyl methacrylate (HMA) for $C_1$ methyl methacrylate (MMA) is illustrated by the leftward and downward shift of the viscosity curves at elevated temperatures. Note that while the dynamic viscosity is essentially the same at 37° C. (note the similar compressive strengths per FIG. 31A), the transition temperature is lowered by about 5° C. with only a modest change in melt viscosity (a change of about 2250 Pa·s at 70° C.). Thus it may be seen that substitution and/or addition of alternative monomers in the polymerization process of a composition having aspects of the invention provides another means of adjusting rheological characteristics to suit a desired medical application.

It should be understood that the polymer compositions having aspects of the invention may further include fillers, plasticizers, elasticizers, modifiers, energy-activated constituents, preservatives, reinforcing fibers, tougheners, pharmaceutical and biologic agents, and other constituents without departing from the spirit of the invention. Likewise, the polymer compositions may be formed ex-vivo or applied in-vivo to form composite materials, layered structures and the like.

The polymer included in the polymer compositions having aspects of the invention may be a homopolymer, a random copolymer, a block copolymer, and the like. Similarly the polymer composition may be a mixture including more than one polymer, where the polymers are selected from one or more of the following: homopolymers, random copolymers, block copolymers, naturally occurring polymers, and the like.

Treatment Methods and Devices Employing Osteoconductive and Osteoinductive Compositions.

Embodiments having aspects of the invention include structural alloplastic bone graft (SABG) systems based upon bioresorbable engineering polymers with unique rheological (flow) properties for the treatment of orthopedic conditions requiring new load-bearing bone growth. The embodiments provide treatment that is exceptionally minimally invasive due to simple flow delivery, yet it provides a superior structural implant. Additionally, due to its bioresorbable, osteoconductive and osteogenic nature, embodiments of SABG systems promote natural bone growth as it degrades. The SABG material is comprised of high-strength bioresorbable polymer that provides structural support and promotes new bone growth as it resorbs.

Embodiments of a polymer-based SABG material have properties which allow it to be delivered in the general manner described above with respect to vertebroplasty. The SABG material is delivered through an orthopedic cannula (tube) introduced to the bone space via a standard trocar-cannula access. A solid pre-form or rod of polymeric material may be fed into a cannula or trocar having leading to a heated tip. As the material goes through the tip, it melts and forms a pliable paste that flows to fill the intended delivery space. Once the external heat source is removed, the material resolidifies at body temperature to form a cohesive and adhesive mass. No further in-situ curing or cross-linking is required to form a structural material.

The embodiments of SABG materials having aspects of the invention may include an active therapeutic agent specifically designed to stimulate bone growth, such as recombinant human bone morphogenetic protein or platelet-derived growth factor. This osteogenic (growth promoting) addition results in rapid recovery times and a more complete and integrated bone graft.

The minimally invasive aspects of the SABG embodiments allow more versatile and adaptable fusion and augmentation therapies. Difficult to access bones may be fused without need for large autograft, allograft, or metal cage implants, such as anterior, posterior and transforaminal, lumbar interbody fusion spinal implants, fixation of cranial, maxillofacial, small and long bone fractures, and the like. In many cases where the SABG system would be employed it would likely result in a shorter, less complicated procedure. The minimally invasive aspects of the SABG embodiments permit fusion and/or augmentation which will be more complete with less procedural tissue damage and thus reduce post procedure hospitalization and follow-up care.

The SABG materials, devices and methods having aspects of the invention include embodiments of a class of high-strength side-chain crystallizable polymers (SCCPs) that have tunable biodegradation, polarity and thermomechanical transition temperatures. Owing to their first-order thermal transition, these SCCPs can be tuned to undergo significant mechanical changes over a narrow, therapeutically acceptable, temperature range. Delivered in the molten state slightly above body temperature and subsequently resolidified, these polymers can be selected to match the properties of the bone that they are replacing with ultimate compression strength (UCS) values of 10's of MPa (similar to healthy young adult lumbar vertebra with UCS values of less than 10 MPa).

Embodiments of SABG material may include blends or mixtures of SCCPs and polymers without crystallizable side chains. Embodiments of SABG material may include either inherently radio-opaque polymers, non-radio opaque polymers or blends or mixtures of these.

Example of a Biodegradable SCCP.

The following is an example of an SCCP which has a hydrolytically unstable polymer backbone which renders it biodegradable in-vivo, and which may be tuned to have properties suitable to be a constituent of a SABG material. This example according to Formulas I and several other examples are fully described in the above incorporated commonly assigned Patent Application Publication US 2006-0182779. The description and teaching above under the sub-heading "Side-Chain Crystallizable Polymers" should be considered in regard to the following example.

An embodiment is a polymer comprising a main chain, a plurality of crystallizable side chains, and a plurality of heavy atoms attached to the polymer, the heavy atoms being present in an amount that is effective to render the polymer radiopaque. A polymer that comprises a recurring unit of the formula (I) is an example of such polymer:

(I)

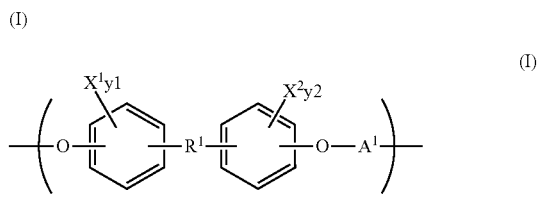

In formula (I), $X^1$ and $X^2$ are each independently selected from the group consisting of Br and I;

y1 and y2 are each independently zero or an integer in the range of 1 to 4; and $A^1$ is selected from the group consisting of:

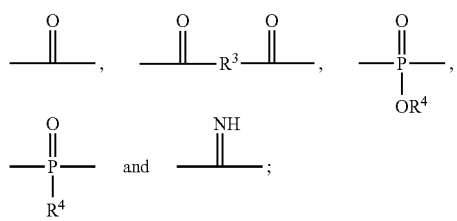

wherein:

$R^3$ is selected from the group consisting of C1-C30 alkyl, C1-C30 heteroalkyl, C5-C30 aryl, C6-C30 alkylaryl, and C2-C30 heteroaryl;

$R^4$ selected from the group consisting of H, C1-C30 alkyl, and C1-C30 heteroalkyl;

$R^1$ is selected from the group consisting of:

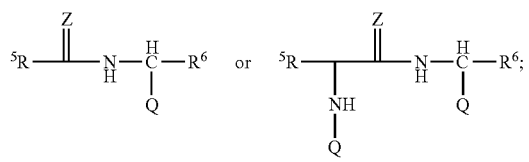

wherein:

$R^5$ and $R^6$ are each independently selected from the group consisting of —CH=CH—, —CHJ$^1$-CHJ$^2$—, and —(CH$_2$)a-; wherein a is zero or an integer in the range of 1 to 8; and $J^1$ and $J^2$ are each independently selected from the group consisting of Br and I;

Z is an O or an S; and

Q is a crystallizable group comprising from about 6 to about 30 carbon atoms, preferably from about 20 to about 30 carbon atoms.

In an embodiment, Q is:

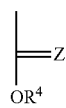

wherein $R^4$ and Z are independently selected from the groups previously defined above.

Polymers of the formula (I) may be prepared by modifying the general methods described in the above incorporated commonly assigned U.S. Pat. No. 7,473,417, to select the appropriate side chain length, side chain spacing and halogen content.

It will be recognized that Q and/or $R^4$ may comprise crystallizable side chains, that each of X, $J^1$ and $J^2$ is a heavy atom, and that y may be adjusted so that the number of heavy atoms in the polymer is sufficient to render the polymer radiopaque. Q and $R^4$ may each independently comprise units selected from the group consisting of —(CH$_2$)$_{n1}$— and —((CH$_2$)$_{m1}$—O—)$_{n1}$; where m1 and n1 are each independently selected so that Q and/or $R^4$ each independently contain from about 1 to about 30 carbon atoms, preferably from about 6 to about 30 carbon atoms, and more preferably from about 20 to 30 carbon atoms. Moreover, Q and $R^4$ may include other functional groups such as ester and amide, and/or heavy atoms such as iodine and bromine. Non-limiting examples of Q and $R^4$ include:

$C_{n1}H_{2n1+1}$, —CO$_2$—C$_{n1}$H$_{2n1+1+1}$, —CONH—C$_{n1}$H$_{2n1+1}$, —(CH$_2$)$_{n1}$—Br, —(CH$_2$)$_{n1}$—I, —CO$_2$—(CH$_2$)$_{n1}$—Br, —CO$_2$—(CH$_2$)$_{n1}$—I, —CONH—CO$_2$—(CH$_2$)$_{n1}$—Br and —CONH—CO$_2$—(CH$_2$)$_{n1}$—I.

In an embodiment:

$R^5$ is —CH=CH— or —(CH$_2$)$_n$—;

$R^6$ is —(CH$_2$)$_a$—; and

Q is an ester group comprising from about 10 to about 30 carbon atoms.

It will be understood that a polymer that comprises a recurring unit of the formula (I) may be a copolymer, e.g., a polymer of the formula (I) that further comprises recurring —$R^2$-$A^2$- units, where $R^2$ is selected from the group consisting of —(CH$_2$)$_{n2}$— and —((CH$_2$)$_{m2}$—O—)$_{n2}$; where m2 and n2 are each independently selected so that $R^2$ contains from about 1 to about 30 carbon atoms; and where $A^2$ is defined in the same manner as $A^1$ above.

Thus, an embodiment provides a polymer comprising recurring units of the formula (Ia):

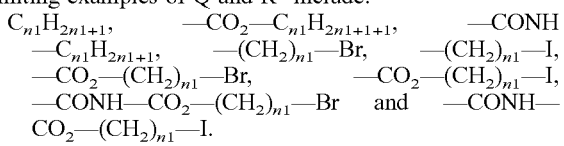

In formula (Ia), $X^1$, $X^2$, y1, y2, $R^1$ and $A^1$ are defined as described above for formula (I); p and q may each be independently varied over a broad range to provide a polymer having the desired properties, e.g., melting point, radiopacity, and viscosity, using routine experimentation. In an embodiment, p and q are each independently an integer in the range of 1 to about 10,000. It will be appreciated that the formula (I) units and —($R^2$-$A^2$)- units in a polymer comprising recurring units of the formula (Ia) may be arranged in various ways, e.g., in the form of a block copolymer, random copolymer, alternating copolymer, or the like.

Polymerization Example.

In an example of synthesis corresponding to polymer of Formula I above, in which an iodinated monomer (I2DT-docosanyl) is employed as shown in Formula VII below.

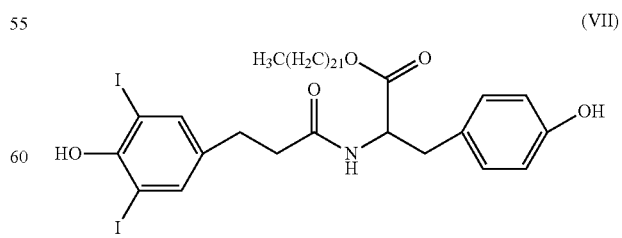

To a 500 mL 2-necked round-bottom flask equipped with a mechanical stirrer and a rubber septum, 30 g of a monomer of the formula VII shown above (I2DT-docosanyl) and 240 ml of methylene chloride are added. The solids are dissolved with stirring. About 4.34 g of triphosgene dissolved in 30 mL of methylene chloride is placed in a airtight syringe and added to the reaction flask with a syringe pump at a constant rate over a period of about 2 to 3 hours. The resulting viscous polymer solution is diluted by adding about 150 mL of tetrahydrofuran and 10 mL of water. The polymer is isolated by precipitating the polymer solution in isopropanol, filtering the resulting solid and drying under vacuum.

The polymer produced is a iodinated SCCP comprising a recurring unit of the formula (I) in which:
$X^1$ is I,
y1 is 2,
y2 is zero,
$A^1$ is —(C═O)—,
$R^5$ is —$CH_2CH_2$—,
$R^6$ is —$CH_2$—, and
Q is a crystallizable ester group containing 23 carbons.

As shown in the examples and methods of FIGS. 21, 22A-B, 23, 24A-C, 25-28, 29A-B, 30A-B, and 31A-B above, the biodegradable side chain crystallizable polymers (SCCP) of the foregoing example has first-order transition thermo-mechanical properties, and may be adapted by control of molecular weight, side chain length, copolymer composition, additives, etc., to have a selected melting point, modulus and the like.

Other SABG Material Constituents.

In addition to a SCCP matrix composition, an embodiment of SABG material having aspects of the invention may comprise one or more of the following:

Osteoconductive Materials.

An osteoconductive component can serve as a scaffold for new bone growth extending from adjacent native bone, permitting osteoblasts to penetrate and generate new bone. These may include ceramics, such as hydroxyapatite, tricalcium phosphate, calcium sulphate, and the like. These may also include bioconductive glasses, including materials such as Bioglass, for example produced commercially as Bioglass 45S5, Biogran, Cerabone, Novabone, PerioGlas or the like, or derivatives, generic equivalents or mixtures thereof.

Osteoinductive Materials.

An osteoinductive component can serve to stimulate osteoprogenitor cells to differentiate into osteoblasts, which in turn can produce new bone. These may include bone morphogenetic proteins or BMPs. Examples include recombinant human bone morphogenetic proteins (rhBMP-2 and rhBMP-7). Other materials, such as demineralized bone matrix (DBM), platelet factors or autologous growth factors, may also be used.

A particulate osteoconductive material and/or an osteoinductive material may be mixed with an SCCP composition in a melted state. The melt mixture may then be formed and solidified into a supply-state material, such as a polymer rod. For example, a supply-state rod may be cast in a mold or extruded. The low melt temperatures permitted by SCCP compositions having aspects of the invention permit a SABG material to be supply with heat labile constituents that would otherwise be destroyed or denatured by higher temperature melts of conventional thermoplastics.

Other Materials.

Optionally, a SABG material having aspects of the invention may comprise additional components providing therapeutic or procedural benefits, such as radiographic or US markers, a radio-opaque additive, an osteogenic component, an antibiotic composition, or the like.

SABG Augmentation and Repair Procedures.

Embodiments of SABG materials having aspects of the invention may be employed in a wide variety of procedures, such as facial fracture repair, periodontal repair, replacement of excised bone tumors, fibular fractures, congenital bone defects, cystic bone loss repair, bone infections, and the like. The flowable application of the material (e.g., from a heating cannula) and rapid hardening to a functional modulus lends the material to minimally invasive procedures. For example, in vertebroplasty, a resorbable SABG material (in contrast to a permanent structural bone cement) may be appropriate for compression fracture repair, particularly in young or middle aged patients.

One example of a bone fusion procedure where the benefits of the structural functionality combined with the in-situ moldablity of the SABG material embodiments is lumbar interbody fusion. In one method embodiment having aspects of the invention, a SABG material embodiments is employed to fill and extend biodegradable balloons inserted into the interbody space following disc removal and surgical site preparation (see, for example, US 2004-0230309). The first order transition of the SCCP component of the composition permits the balloon inflation to be carried out at a temperature low enough to avoid damage to native bone tissue and/or the denaturing of heat-labile components of the graft material. The fluid pressure in the balloon at delivery may be controlled to provide a selected degree of distraction or separation of the vertebral bodies. Following cooling to body temperature, the SABG material rapidly solidifies to have structural stability not depending on further balloon support. Thus the balloon may be made of a rapidly biodegradable composition.

Figure 33:
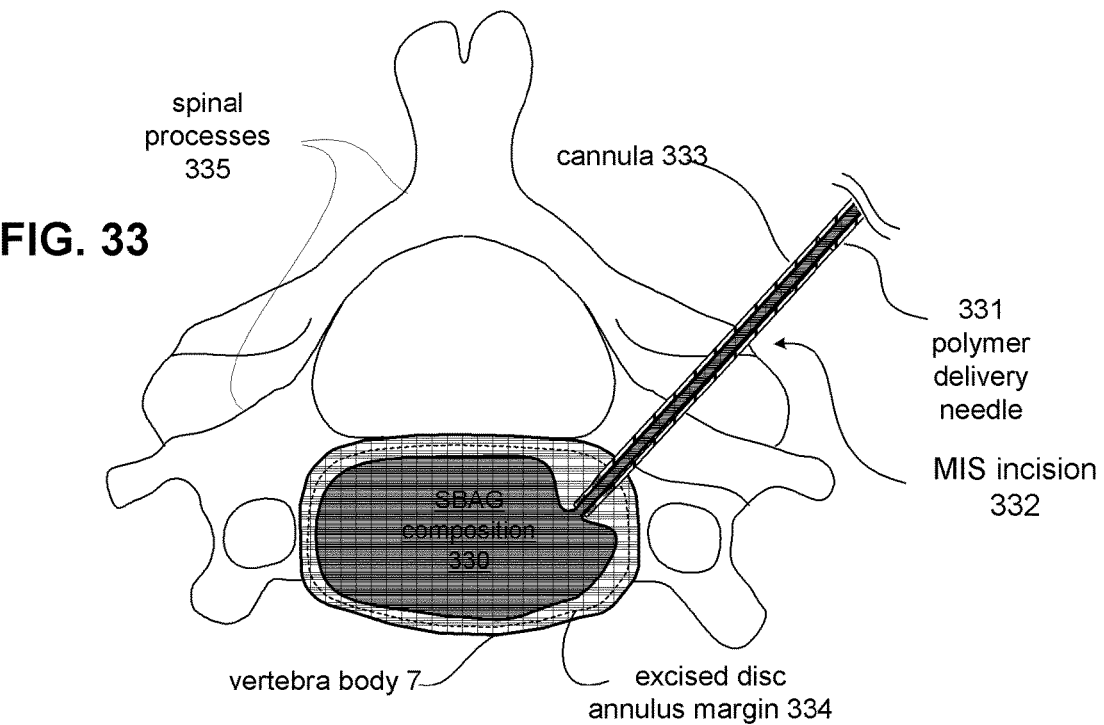
FIG. 33 is a cross-sectional view of a lumbar spine, depicts schematically a structural alloplastic bone graft (SABG) procedure having aspects of the invention to fuse adjacent vertebral bodies.
Figure 34:
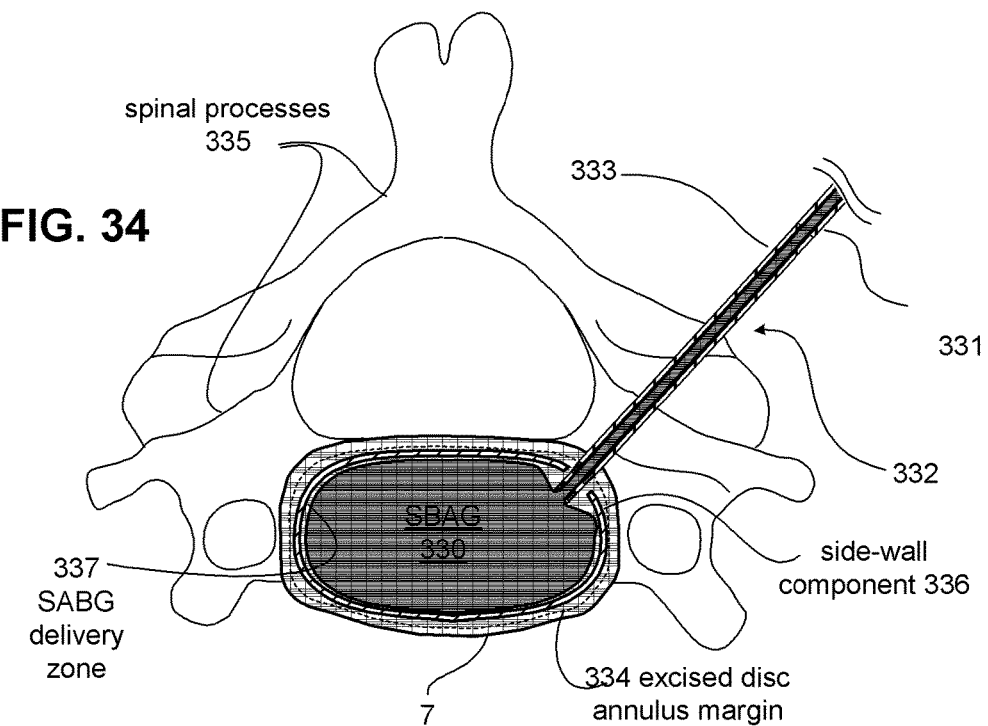
FIG. 34 is a cross-sectional view of a lumbar spine, depicts schematically an alternative SABG procedure to fuse adjacent vertebral bodies.

However, the structural properties of the SABG material embodiments having aspects of the invention permit the materials to be formed in situ as a vertebral structural support having inherent osteo-biological performance, e.g., using either anterior lumbar interbody fusion (ALIF) or Transforaminal lumbar interbody fusion (TLIF). FIGS. 33 and 34 depict schematically such a procedure, in this case a procedure performed by MIS access to the lateral posterior lumbar spine.

FIG. 33, is a cross-sectional view of a lumbar spine, depicts schematically a structural alloplastic bone graft (SABG) procedure having aspects of the invention to fuse adjacent vertebral bodies. The lower vertebral body and associated spinal processes is shown, following surgical removal of all or a part of the spinal disc annulus and nucleus. A cannula is inserted though a small incision to access the intervertebral space.

A heated polymer delivery needle 331 generally similar to those depicted and described with respect to FIGS. 19A though 19F may be inserted to deliver a melted SABG composition 330 having aspects of the invention in to the intervertebral space. It should be understood that the intervertebral spacing and angle may be adjusted by conventional means (not depicted), such as spinal traction, wedges, expandable structures, inflatable structures, and the like. The bolus of SABG material 330 is deposited at a selected delivery temperature to cover all or a portion of the vertebral plate exposed by excision of the disc material, and permitted to cool to body temperature and solidify.

In one alternative method (not depicted in FIG. 33), the SABG material may be delivered in more than one bolus. A spacer or other distraction device or devices may be inserted into a chosen portion of the intervertebral space. The SABG material may then be delivered in a first bolus filling a portion of the intervertebral space not obstructed by a spacer or other distraction device (additional incisions may be made for this purpose, if desired). The first bolus may then be allowed to solidify.

Subsequently the spacer(s) or distraction device(s) may be re-adjusted to expose additional intervertebral space, followed by delivery and solidification of one or more additional boluses SABG material. For example, a central bolus may be delivered first while right and left vertebral body portions are supported by distraction devices, such as wedges. Upon solidification, the central bolus will support the intervertebral spacing as a central pillar-like structure. Subsequent boluses, such as right and left boluses, may be added as desired to provide a broader support and a broader area of osteo-biologic material.

As shown in FIG. 33, the polymer delivery may be performed from a single MIS incision 332. It should be noted that the procedure may alternatively be performed via more than one incision, such as via dual right and left incisions, to permit delivery of SABG material from more than one direction. Alternatively or additionally, a delivery needle may be provided with an extended tip, which may be curved or steerable (not depicted), so as to reach within the intervertebral space to a desired location to deposit melted SABG material.

FIG. 34 is a cross-sectional view of a lumbar spine, depicting schematically an alternative SABG procedure having aspects of the invention to fuse adjacent vertebral bodies. In this alternative, one or more side wall components are inserted into the intervertebral space, following disc removal. side wall components extend in a caudal-cranial dimension through all or a portion of the distracted intervertebral space, to define a SABG delivery zone. For example, a side wall component may comprise a shape memory or spring-like structure which is insertable though a cannula, reshaping to a desired wall shape upon release into the intervertebral space. The side wall component may comprise a metallic material (e.g., nitinol), or may comprise a non-metallic material (e.g., a shape memory polymer), or combinations of these.

As depicted in FIG. 34, the side wall is shaped to cover most of the circumference of the vertebral end plate. However, it may alternative cover only a portion of the perimeter of the SABG delivery zone, e.g., a posterior portion, an anterior portion, a lateral portion, or combinations of these. In other alternatives, more than one side wall components are applied (not depicted), so as to define more than one SABG delivery zones. These may define different portions of the vertebral endplates.

Melted SABG composition 330 is delivered within the side wall in generally the same manner as in the embodiments of FIG. 33. Likewise, where more than one SABG delivery zone, these may be filled sequentially, with solidification between filling boluses, such as in the manner described above with respect the embodiments of FIG. 33, so as to provide interim spinal support while subsequent boluses are applied.

It will be appreciated by those skilled in the art that various omissions, additions and modifications may be made to the materials and methods described above without departing from the scope of the invention, and all such modifications and changes are intended to fall within the scope of the invention, as defined by the appended claims.

Likewise, it should be understood that the methods, device and materials having aspects of the invention shown in the Figures and described above are exemplary only. Alternative methods, device and materials having aspects of the invention may be practices without undue experimentation and without departing from the spirit of the invention. For example, an alternative polymer delivery system having aspects of the invention may feed the polymer composition to a delivery needle in the form of spherical beads, the beads fed under mechanical or fluid pressure, such as by a piston, so as to contact a heated distal portion of the delivery needle. The beads may then be extruded into a patient's body portion such as a vertebral body. The bead composition may be changed during course of a procedure, such as by accessing different bead reservoirs.

The invention claimed is:

1. A polymer composition for augmentation and support of bone tissue, comprising a side chain crystallizable polymer, wherein:
   (i) the polymer composition has a solid state when within a first temperature range, the first temperature range selected to substantially correspond to temperatures generally found in anatomical bone structures of living mammals, the solid state having mechanical properties suitable for supporting and/or augmenting bone tissue;
   (ii) the polymer composition has a second transition temperature range, the second transition temperature range being above the first temperature range;
   (iii) the polymer composition has an extrudable fluid state when in a third temperature range, the third temperature range being above the second temperature range; the third temperature range selected to correspond to therapeutically acceptable temperatures for the bone tissue being treated, the extrudable fluid state in the third temperature range having a viscosity sufficiently low to permit injection into the bone tissue being treated; and
   (iv) the side chain crystallizable polymer comprises an amount of polar groups selected to increase the adhesion of the side chain crystallizable polymer to the bone tissue.

2. The polymer composition of claim 1, further comprising a radio-opaque additive.

3. The polymer composition of claim 1, wherein the side chain crystallizable polymer comprises a —$(CH_2)n$- group in a side chain, where n is an integer in the range of about 6 to about 30.

4. The polymer composition of claim 3, where n is an integer in the range of about 20 to about 30.

5. The polymer composition of claim 1, wherein the side chain crystallizable polymer is a copolymer comprising at least a first recurring unit having an optional —$(CH_2)m$- group where m is an integer in the range of about 0 to about 5; and at least a second recurring unit having a —$(CH_2)n$- group where n is an integer in the range of about 6 to about 30.

6. The polymer composition of claim 5, wherein at least one of the recurring units is an alkyl methacrylate.

7. The polymer composition of claim 1, wherein the first temperature range is from about 37° C. to about 41° C.

8. The polymer composition of claim 1, wherein the third temperature range is from about 45° C. to about 100° C.

9. The polymer composition of claim 1, wherein the third temperature range is from about 50° C. to about 80° C.

10. The polymer composition of claim 1, wherein the side chain crystallizable polymer is a copolymer comprising two or more recurring units selected from the group consisting of methyl methacrylate, ethyl methacrylate, hexyl methacrylate, and behenyl methacrylate.

* * * * *